US012665067B1

(12) United States Patent
Mandlekar et al.

(10) Patent No.: US 12,665,067 B1
(45) Date of Patent: Jun. 23, 2026

(54) SYSTEMS AND METHODS FOR ANALYZING BLOOD GLUCOSE AND CHANGING HUMAN BEHAVIOR

(71) Applicant: LumosFit Inc., San Jose, CA (US)

(72) Inventors: Hemamalini Mandlekar, San Jose, CA (US); Meghana Dipti Gadgil, San Francisco, CA (US); Felicia Lim Sanborn, San Ramon, CA (US)

(73) Assignee: LumosFit Inc., San Jose, CA (US)

( * ) Notice: Subject to any disclaimer, the term of this patent is extended or adjusted under 35 U.S.C. 154(b) by 0 days.

(21) Appl. No.: 19/266,765

(22) Filed: Jul. 11, 2025

Related U.S. Application Data

(60) Provisional application No. 63/670,585, filed on Jul. 12, 2024.

(51) Int. Cl.
　　*G16H 20/60*　　(2018.01)
　　*A61B 5/00*　　(2006.01)
　　*G09B 5/02*　　(2006.01)
　　*A61B 5/145*　　(2006.01)

(52) U.S. Cl.
　　CPC ........... *G16H 20/60* (2018.01); *A61B 5/4866* (2013.01); *G09B 5/02* (2013.01); *A61B 5/14532* (2013.01)

(58) Field of Classification Search
　　CPC ............................ G09B 19/0092; G16H 20/60
　　See application file for complete search history.

(56) References Cited

U.S. PATENT DOCUMENTS

| | | | |
|---|---|---|---|
| 6,990,364 B2 | 1/2006 | Ruchti et al. | |
| 11,250,942 B1 * | 2/2022 | Ahmad | ................. G16H 20/60 |
| 2015/0371553 A1 * | 12/2015 | Vento | ................. G09B 19/0092 |
| | | | 434/127 |
| 2016/0328991 A1 * | 11/2016 | Simpson | ............ G09B 19/0092 |
| 2017/0242975 A1 * | 8/2017 | Kahlbaugh | ............ G16H 50/50 |

(Continued)

FOREIGN PATENT DOCUMENTS

| | | |
|---|---|---|
| WO | 9200513 A1 | 1/1992 |
| WO | 2018214298 A1 | 11/2018 |

OTHER PUBLICATIONS

Javid et al. article titled "Noninvasive Optical Diagnostic Techniques for Mobile Blood Glucose and Bilirubin Monitoring," © 2018 Journal of Medical Signals & Sensors | Published by Wolters Kluwer—Medknow, Website: www.jmss.mui.ac.ir, DOI: 10.4103/jmss.JMSS_8_18 (15 pages).

(Continued)

*Primary Examiner* — Peter R Egloff
(74) *Attorney, Agent, or Firm* — Aurora Consulting LLC; Kristen J. Hansen; Ashley Sloat

(57) ABSTRACT

Methods and systems are described for a computer-implemented method for managing behavior in a subject, the method comprising: monitoring a plurality of behavioral events, each event being correlated to a timestamp within a time period; identifying a pattern in the plurality of behavioral events; generating, based on the identified pattern, personalized content for the subject; generating one or more nudges for the subject based on the personalized content, wherein the one or more nudges comprise prompts or suggestions aimed at encouraging adherence to executing suggested behavior changes provided in the personalized content; and causing presentation of the personalized content and the one or more nudges to the subject.

30 Claims, 26 Drawing Sheets

(56) References Cited

U.S. PATENT DOCUMENTS

| | | | | |
|---|---|---|---|---|
| 2018/0082139 A1* | 3/2018 | Li | ........................ | G06V 30/224 |
| 2020/0205704 A1* | 7/2020 | Vanslyke | ............... | A61B 5/742 |
| 2020/0350052 A1* | 11/2020 | Saint | ..................... | G16H 10/40 |
| 2021/0104173 A1* | 4/2021 | Pauley | .................. | G16H 20/10 |
| 2022/0000399 A1* | 1/2022 | Hayter | .................. | A61B 5/743 |
| 2022/0079477 A1 | 3/2022 | Deng | | |
| 2022/0130276 A1* | 4/2022 | Banavar | ................ | G16H 50/20 |

OTHER PUBLICATIONS

Wang et al. article titled "Modeling on the feasibility of camera-based blood glucose measurement," provided by Computer Vision Foundation (identical to final published version of the proceedings on IEEE Xplore. (8 pages).

* cited by examiner

Glucose Meter reading: 93 mg/dL

Glucose Meter reading: 89 mg/dL 502
504a
506a
508a
500A

Glucose Meter reading: 98 mg/dL 502
504b
506b
508b
500B

Glucose Meter reading: 110 mg/dL

602a

500A1

Glucose Meter reading:  98 mg/dL

602b

500B1

Glucose Meter reading:  110 mg/dL

Glucose Meter reading: 82 mg/dL

Glucose Meter reading: 132 mg/dL

802a

Glucose Meter reading:  96 mg/dL

802b

Glucose Meter reading:  96 mg/dL

904a

902a

Glucose Meter reading: 71 mg/dL

904b

902b

Glucose Meter reading: 121 mg/dL

1002

Glucose Meter reading:  97 mg/dL

1002

Glucose Meter reading:  92 mg/dL

1102

Glucose Meter reading:  91  mg/dL

1102

Glucose Meter reading:  108 mg/dL

1300

1302
Cause an infrared light source
to illuminate a body site of a subject

1304
Capture at least one digital image representing
reflected light from the body site 1306
Programmatically analyze the at least one digital
image to assess blood glucose for the subject 1308
Generate an indication representing a blood glucose
measurement

1550

1560

1558

1552

1556

1570

Sensing the
volar side of the
opposite wrist

Sensors on the
outside of our
band

1550

Smart
watch

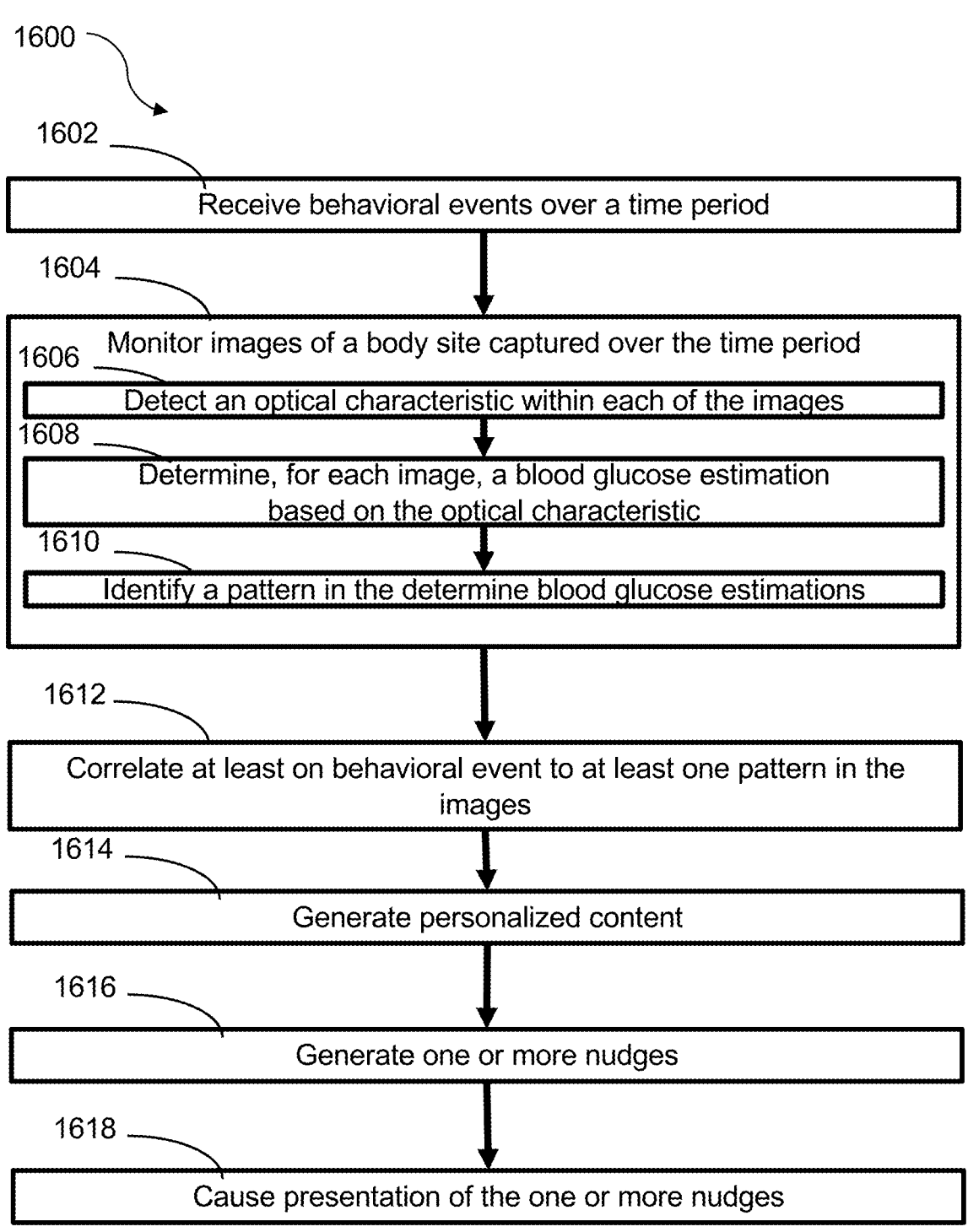

1600

1602
Receive behavioral events over a time period 1604
1606 Monitor images of a body site captured over the time period
Detect an optical characteristic within each of the images
1608
Determine, for each image, a blood glucose estimation based on the optical characteristic
1610
Identify a pattern in the determine blood glucose estimations 1612
Correlate at least on behavioral event to at least one pattern in the images 1614
Generate personalized content 1616
Generate one or more nudges 1618
Cause presentation of the one or more nudges

Figure 17A:
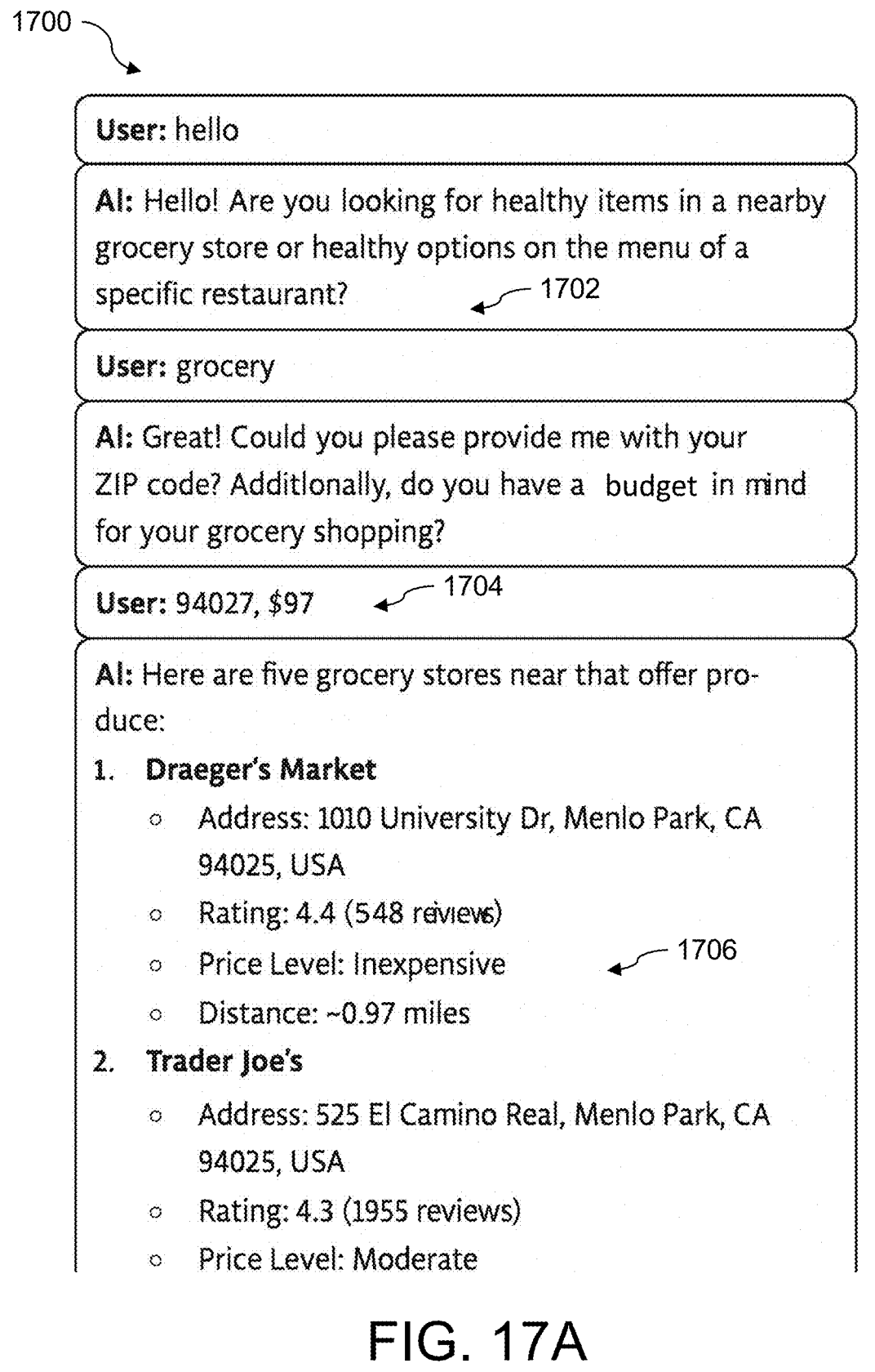

User: hello

AI: Hello! Are you looking for healthy items in a nearby grocery store or healthy options on the menu of a specific restaurant? ← 1702

User: grocery

AI: Great! Could you please provide me with your ZIP code? Additionally, do you have a budget in mind for your grocery shopping?

User: 94027, $97 ← 1704

AI: Here are five grocery stores near that offer produce:

1. Draeger's Market
   - Address: 1010 University Dr, Menlo Park, CA 94025, USA
   - Rating: 4.4 (548 reviews)
   - Price Level: Inexpensive ← 1706
   - Distance: ~0.97 miles
2. Trader Joe's
   - Address: 525 El Camino Real, Menlo Park, CA 94025, USA
   - Rating: 4.3 (1955 reviews)
   - Price Level: Moderate

4.   Sigona's Farmers Market in Palo Alto o   Address: 399 Stanford Shopping Center, Palo Alto, CA 94304, USA o   Rating: 4.5 (286 reviews)

o   Price Level: Moderate o   Distance: ~1.85 miles

5.   Target Grocery o   Address: 2485 El Camino Real, Redwood City, CA 94063, USA o   Rating: 4.5 (112 reviews)

o   Price Level: Unknown o   Distance: ~1.85 miles

Figure 17B:
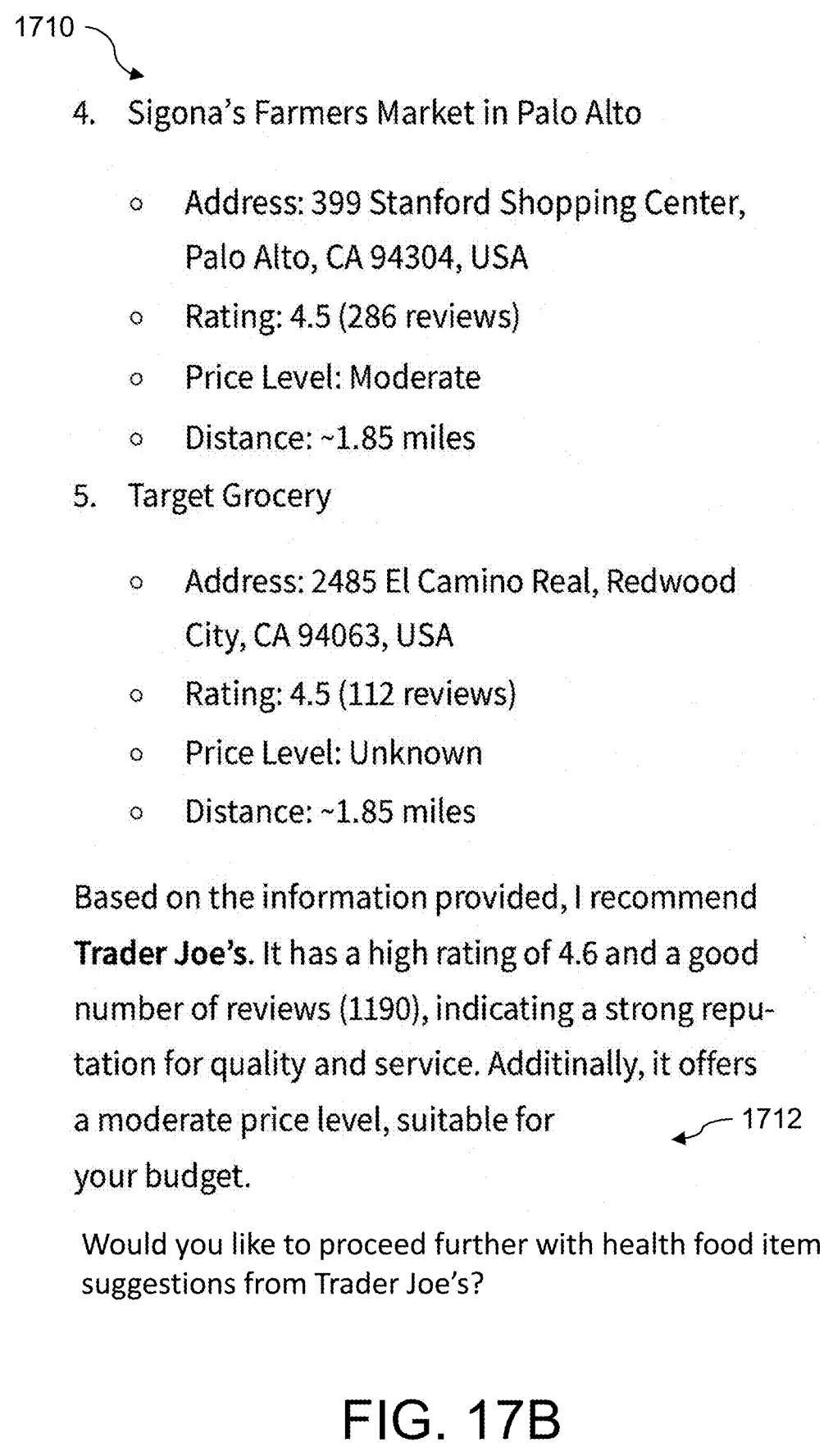

Based on the information provided, I recommend Trader Joe's. It has a high rating of 4.6 and a good number of reviews (1190), indicating a strong reputation for quality and service. Additionally, it offers a moderate price level, suitable for your budget.

1712

Would you like to proceed further with health food item suggestions from Trader Joe's?

Figure 17C:
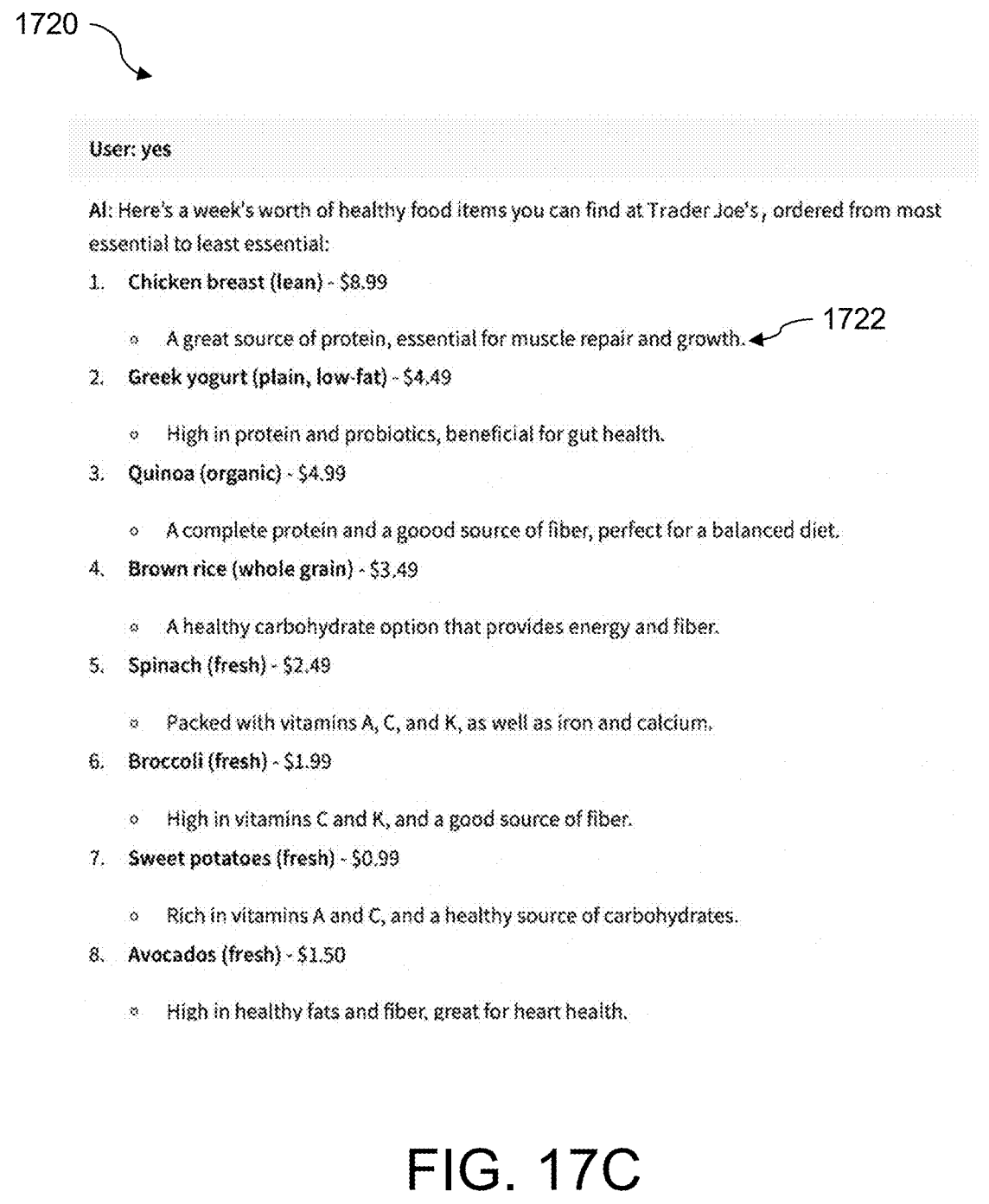

User: yes

AI: Here's a week's worth of healthy food items you can find at Trader Joe's, ordered from most essential to least essential:

1. Chicken breast (lean) - $8.99 o   A great source of protein, essential for muscle repair and growth. ◄— 1722

2. Greek yogurt (plain, low-fat) - $4.49 o   High in protein and probiotics, beneficial for gut health.

3. Quinoa (organic) - $4.99 o   A complete protein and a good source of fiber, perfect for a balanced diet.

4. Brown rice (whole grain) - $3.49 o   A healthy carbohydrate option that provides energy and fiber.

5. Spinach (fresh) - $2.49 o   Packed with vitamins A, C, and K, as well as iron and calcium.

6. Broccoli (fresh) - $1.99 o   High in vitamins C and K, and a good source of fiber.

7. Sweet potatoes (fresh) - $0.99 o   Rich in vitamins A and C, and a healthy source of carbohydrates.

8. Avocados (fresh) - $1.50 o   High in healthy fats and fiber, great for heart health.

Figure 17D:
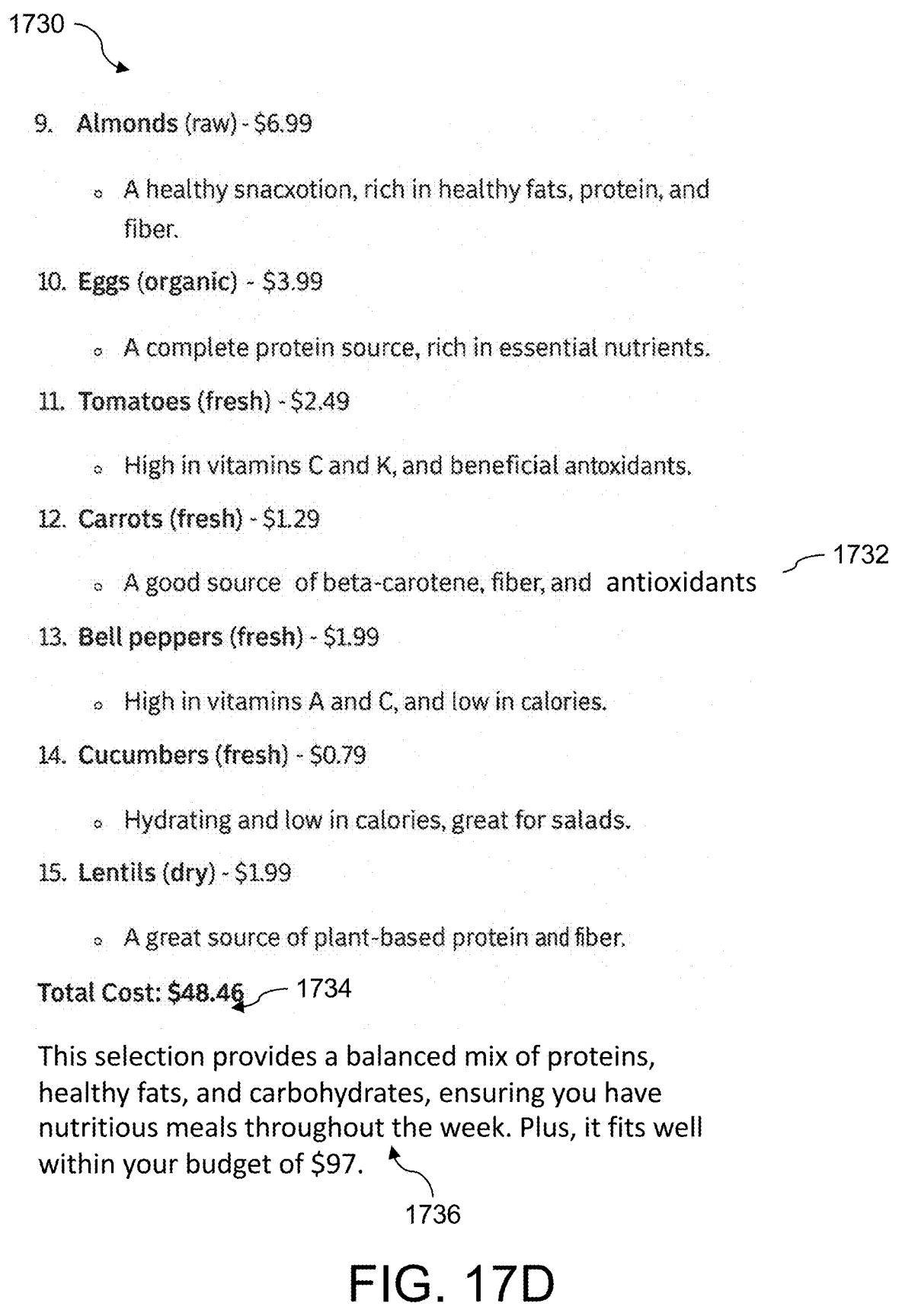

9.   Almonds (raw) - $6.99

○   A healthy snacxotion, rich in healthy fats, protein, and
       fiber.

10.  Eggs (organic) - $3.99

○   A complete protein source, rich in essential nutrients.

11.  Tomatoes (fresh) - $2.49

○   High in vitamins C and K, and beneficial antoxidants.

12.  Carrots (fresh) - $1.29

○   A good source  of beta-carotene, fiber, and  antioxidants   ⟋ 1732

13.  Bell peppers (fresh) - $1.99

○   High in vitamins A and C, and low in calories.

14.  Cucumbers (fresh) - $0.79

○   Hydrating and low in calories, great for salads.

15.  Lentils (dry) - $1.99

○   A great source of plant-based protein and fiber.

Total Cost: $48.46  ⟋ 1734

This selection provides a balanced mix of proteins,
healthy fats, and carbohydrates, ensuring you have
nutritious meals throughout the week. Plus, it fits well
within your budget of $97.

1800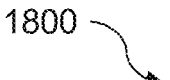

AI: Here are three healthy options from the McDonald's menu:

1.Premium Southwest Salad with Grilled Chicken
1. Calories: 320  ← 1802
2. Sugar: 11g  ← 1804
3. Carbohydrates: 30g  ← 1806
4. Description: This salad is a great source of ← 1808
   protein and includes a variety of vegetables,
   making it a nutritious choice.

2.Premium Bacon Ranch Salad with Grilled Chicken
1. Calories: 260
2. Sugar: 5g
3. Carbohydrates: 12g
4. Description: Another salad option that provides
   lean protein and is lower in calories, making it a
   healthy choice.

3.Egg McMuffin
1. Calories: 300
2. Sugar: 3g
3. Carbohydrates: 30g
4. Description: This breakfast sandwich is a good
   source of protein and has a moderate calorie
   count, making it a balanced option.

These choices are healthy because they are lower in
calories and sugar, while providing essential nutrients.
Would you like more options or information?

Figure 18B:
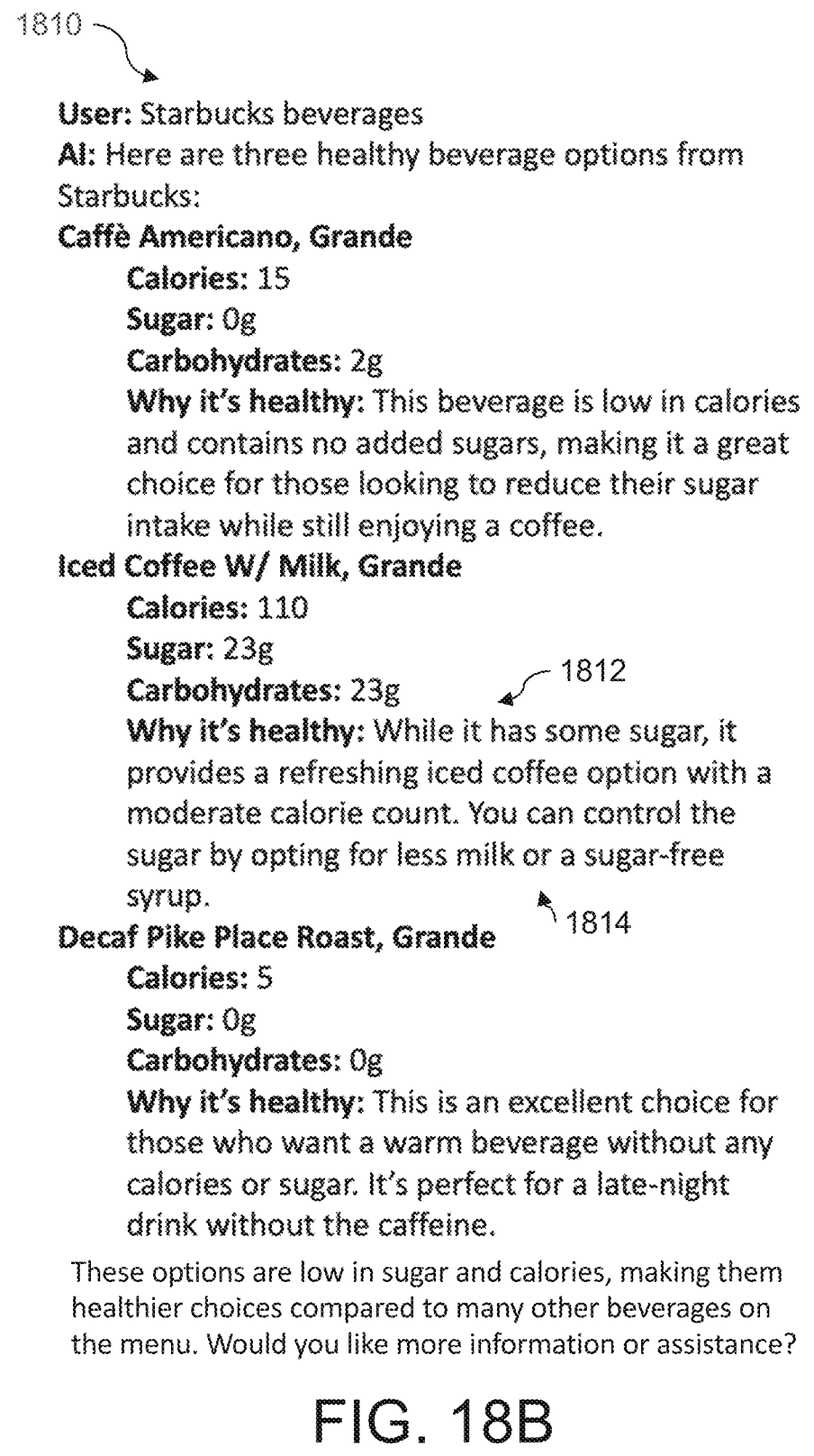

User: Starbucks beverages

AI: Here are three healthy beverage options from Starbucks:

Caffè Americano, Grande

> Calories: 15
>
> Sugar: 0g
>
> Carbohydrates: 2g
>
> Why it's healthy: This beverage is low in calories and contains no added sugars, making it a great choice for those looking to reduce their sugar intake while still enjoying a coffee.

Iced Coffee W/ Milk, Grande

> Calories: 110
>
> Sugar: 23g
>
> Carbohydrates: 23g          _1812_
>
> Why it's healthy: While it has some sugar, it provides a refreshing iced coffee option with a moderate calorie count. You can control the sugar by opting for less milk or a sugar-free syrup.

Decaf Pike Place Roast, Grande          _1814_

> Calories: 5
>
> Sugar: 0g
>
> Carbohydrates: 0g
>
> Why it's healthy: This is an excellent choice for those who want a warm beverage without any calories or sugar. It's perfect for a late-night drink without the caffeine.

These options are low in sugar and calories, making them healthier choices compared to many other beverages on the menu. Would you like more information or assistance?

Monitor a plurality of behavioral events

1904

Identify a pattern in the plurality of behavioral events

1906

Generate personalized content for the subject based on the identified pattern

1908

Generate one or more nudges for the subject based on the personalized content

1910

Cause presentation of the personalized content and the one or more nudges to the subject

SYSTEMS AND METHODS FOR ANALYZING BLOOD GLUCOSE AND CHANGING HUMAN BEHAVIOR

CROSS-REFERENCE TO RELATED APPLICATION

This application claims the priority benefit of U.S. Provisional Patent Application Ser. No. 63/670,585, filed Jul. 12, 2024, which is herein incorporated by reference in its entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates generally to the field of general wellness, and more specifically to the field of diabetes management and related human behavior. Described herein are systems and methods that utilize large language models and/or generative artificial intelligence to change human behavior associated with managing health and diabetes.

BACKGROUND

The prevalence of diabetes, including type 2 diabetes (T2D), type 1 diabetes (TID), and prediabetes will increase to more than 54.9 million Americans by 2030 and is projected to cross half a billion people worldwide by 2040. Before developing T2D, most people have prediabetes where blood sugar values are higher than a predefined normal, but not high enough yet for a diabetes diagnosis. While the prevalence of such conditions is predicted to increase substantially in the near future, proper blood glucose management can effectively reverse this condition, thus improving the health outcomes of these individuals. Several aspects of the etiology of T2D suggest that both high-risk and whole-population approaches are helpful to make a major impact on trends in the diabetes epidemic.

Self-monitoring of blood glucose (SMBG) is a helpful disease management component for improving patient/device user self-management and guiding clinicians in adjusting medications. SMBG data is used to improve glycemic control and identify hypoglycemic events, and also persistent hyperglycemia. The clinical utility of SMBG is dependent upon patients understanding the proper technique, being adherent to testing, and correctly interpreting the results. In addition, clinical utility comes from patients sharing their testing results with providers, and providers acting on that data to make treatment decisions.

SUMMARY

In some aspects, the techniques described herein relate to a computer-implemented method for managing behavior in a subject, the method including: monitoring a plurality of behavioral events, each event being correlated to a timestamp within a time period; identifying a pattern in the plurality of behavioral events; generating, based on the identified pattern, personalized content for the subject; generating one or more nudges for the subject based on the personalized content, wherein the one or more nudges include prompts or suggestions aimed at encouraging adherence to executing suggested behavior changes provided in the personalized content; and causing presentation of the personalized content and the one or more nudges to the subject.

In some aspects, the techniques described herein relate to a computer-implemented method, wherein: at least one of the plurality of behavioral events includes a last consumed meal; the personalized content includes feedback on the last consumed meal.

In some aspects, the techniques described herein relate to a computer-implemented method, wherein the feedback includes suggested timing for a next meal and educational content, the educational content including a meal plan for the subject that minimizes glucose spikes over a second time period.

In some aspects, the techniques described herein relate to a computer-implemented method, wherein the personalized content includes one or more of: dietary recommendations, exercise suggestions, and lifestyle modifications.

In some aspects, the techniques described herein relate to a computer-implemented method, wherein the method further includes: monitoring a behavior or input responsive to the presentation of the one or more nudges; iteratively repeating the monitoring of behavior exhibited by the subject; in response to detecting additional behavioral events, identifying an additional pattern in the additional behavioral events; updating the personalized content according to the additional behavioral events based on the identified additional pattern; generating an updated nudge corresponding to the updated personalized content; and causing presentation of the updated nudge and the updated personalized content to the subject.

In some aspects, the techniques described herein relate to a computer-implemented method, wherein the monitoring of the plurality of behavioral events is performed at least in part by an artificial intelligence computer agent configured to use data generated by the monitoring and a plurality of template guides to generate the one or more nudges.

In some aspects, the techniques described herein relate to a computer-implemented method, wherein the method further includes: adapting the personalized content based on contextual information associated with the subject, wherein the contextual information includes at least one of: a current location, a time of day, one or more upcoming events, or one or more recent activities.

In some aspects, the techniques described herein relate to a computer-implemented method, wherein the method further includes: determining, based on the plurality of behavioral events and the monitoring, a nudge mode from a plurality of nudge modes, a historical adherence to previous nudges or recommendations generated for the subject; and generating the one or more nudges according to the determined nudge mode.

In some aspects, the techniques described herein relate to a computer-implemented method, wherein the plurality of nudge modes includes a light mode, a regular mode, and a heavy mode.

In some aspects, the techniques described herein relate to a computer-implemented method, wherein the light mode is activated during at least one of: holidays, travel, postpartum periods, short-term illnesses, or user-designated cheat days.

In some aspects, the techniques described herein relate to a computer-implemented method, wherein the heavy mode is activated during at least one of: periods following discontinuation of one or more medications or when the subject sets aggressive health goals.

In some aspects, the techniques described herein relate to a computer-implemented method, wherein: monitoring the plurality of behavioral events includes monitoring or receiving blood glucose data for the subject; identifying the pattern in the plurality of behavioral events includes identifying a glucose time in range for the subject; and selecting, based on the glucose time in range, one or more times in which to present the one or more nudges to the subject.

In some aspects, the techniques described herein relate to a computer-implemented method, wherein the personalized content includes a grocery shopping list curated according to the identified pattern, and the method further includes automatically placing a plurality of items on the grocery shopping list in an online shopping cart or automatically placing an order of the plurality of items on the grocery shopping list.

In some aspects, the techniques described herein relate to a computer-implemented method, wherein the personalized content includes a plurality of restaurant menu suggestions selected according to the identified pattern, and food data corresponding to each of the plurality of restaurant menu suggestions, the food data indicating one or more of: calorie content, sugar content, carbohydrate content, and at least one reason for selecting the respective restaurant menu suggestions.

In some aspects, the techniques described herein relate to a computer-implemented method, wherein the computer-implemented method is performed by an artificial intelligence health coach configured to share data with a buddy computing device according to permissions associated with the subject, the shared data including one or more of: a blood glucose estimation, identified behavioral patterns, a status update corresponding to the subject, and a summary corresponding to the subject.

In some aspects, the operations described herein are performed by an artificial intelligence computer agent configured to use data generated by monitoring the behavior of the subject and a plurality of template guides to generate the one or more nudges to coach the subject to modify the behavior over an upcoming time period.

In some aspects, the techniques described herein relate to a system or a computer-readable medium that perform the above recited techniques.

Implementations of the described techniques may include hardware, a method or process, or computer software on a computer-accessible medium. The details of one or more implementations are set forth in the accompanying drawings and the description below. Other features will be apparent from the description and drawings, and from the claims.

BRIEF DESCRIPTION OF THE DRAWINGS

The foregoing is a summary, and thus, may be limited in detail. Approaches for performing a noninvasive blood glucose measurement and/or related prediction are presented herein. The above-mentioned aspects, as well as other aspects, features, and advantages of the present technology are described below in connection with various embodiments, with reference made to the accompanying drawings.

FIG. 16 illustrates a flow diagram of an example process for managing blood glucose levels in a subject.

FIGS. 17A-17D illustrate an example user interface of a conversational exchange depicting an interaction sequence between a user and an AI-driven user interface.

FIGS. 18A-18B illustrate example user interfaces of a conversational exchange depicting an interaction sequence between a user and an AI-driven user interface for providing personalized health and fitness recommendations.

Figure 1:
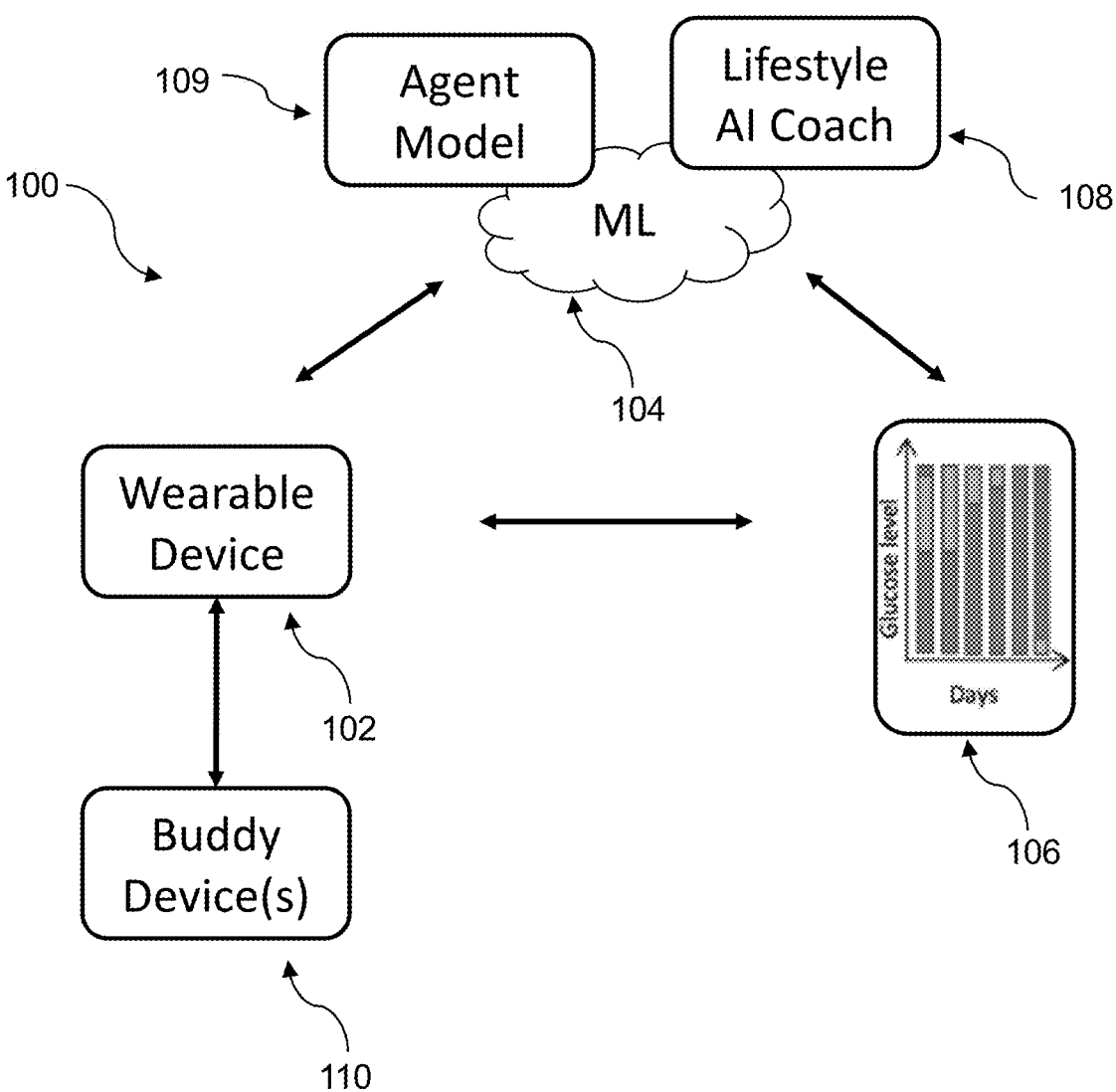
FIG. 1 illustrates an example high level system for obtaining noninvasive glucose assessments for a body site of a user and monitoring well-being and/or glucose and generating recommendations or other content for behavioral and/or lifestyle changes.

The illustrated embodiments are merely examples and are not intended to limit the disclosure. The schematics are drawn to illustrate features and concepts and are not necessarily drawn to scale.

DETAILED DESCRIPTION

The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated claimed subject matter. Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

Described herein are systems and methods that utilize large language models and/or generative artificial intelligence to assess and change human behavior associated with managing user health, lifestyle, and diabetes. In some implementations, the systems and methods may utilize one or more devices (e.g., device 102, bands 1500, or band 1550) for performing non-invasive glucose monitoring, behavior assessment, and recommendation/actionable instruction/insight generation. In some implementations, the systems and methods described herein may monitor, determine, and inform the user about an anticipated or recent glucose reading and provide information about a recent trend in glucose readings for the user. In some embodiments, the systems and methods described herein can perform such monitoring to facilitate obtaining health knowledge for a user and to assist in user adherence to lifestyle improvements to reduce risks for developing blood sugar related illness, including, but not limited to: Type 2 Diabetes (T2D), Type 1 Diabetes (TID), and prediabetes. In some embodiments, the systems and methods described herein may be used to enable early diagnosis of Type 2 Diabetes (T2D), Type 1 Diabetes (TID), and/or prediabetes. In some embodiments, the systems and methods described herein can generate predictive glucose responses and predictive health related events. In some embodiments, the systems and methods described herein can use data obtained from glucose monitoring to facilitate predictions that may be used to generate instructions for a user to carry out to treat, manage, and/or prevent blood sugar related illnesses.

One technical problem sought to be solved by the systems described herein is to provide non-invasive, near real time and/or continuous glucose and/or behavior monitoring for a user. An example technical solution provided by the embodiments described herein includes employing at least one sensor device, software algorithms, and/or one or more machine learning (ML) models to assess glucose changes and/or related behavior over time for a user. For example, the systems described herein may include a device arranged to capture images of a body site including at least one venous structure (e.g., a vein). The systems described herein may include one or more of: a wearable device, a server(s), an artificial intelligence model, or the like. Such systems may analyze the images to determine blood glucose levels and/or blood glucose changes. In some embodiments, the systems described herein may detect/determine blood glucose changes over time and in response, may generate content such as recommendations, actionable instructions, and/or insights for a user wearing or otherwise accessing a wearable device arranged to capture images of a body site having at least one viewable venous structure. In some embodiments, the content may be based on the detected/determined glucose changes for a user. In some embodiments, the content may be based on detected/determined glucose changes for a user and historical glucose data for the user. In some embodiments, the content may be based on detected/determined glucose changes for a user, historical glucose data for the user, and/or historical glucose data for any number of other users. In some embodiments, the content includes educational content selected according to glucose behavior, tracked eating behavior, and/or tracked exercise behavior.

The detected and/or monitored behaviors described herein may be managed, coached, or otherwise modified by the systems described herein. For example, the systems described herein may implement comprehensive behavioral and physiological monitoring across multiple categories to enable personalized health interventions and coaching. The behaviors may include, but are not limited to one or more of: dietary behavior, physical activity behavior, sleep and circadian rhythm behavior, stress or emotional behavior, communication and/or technology usage pattern behaviors, location-based or environmental behaviors, physiological behaviors or measurements, and hormonal and temporal behaviors, etc.

For example, dietary behavior management may include the systems described herein monitoring a frequency and timing of meals and tracking specific meal content. Such a system may analyze tracked eating behavior and can identify high added sugar consumption as a modifiable risk factor including monitoring consumption of sugar-sweetened beverages (e.g., soda, candy, fruit drinks, etc.) and/or refined carbohydrates (e.g., white bread, white rice, pastries, etc.). In some embodiments, the systems described herein may further monitor alcohol intake patterns, including frequency and context (e.g., social functions, weekends) to provide behavioral guidance, and may track eating timing such as monitoring adherence to a cutoff time for evening eating (e.g., 8 or 9 PM), to assist and/or coach the user with ways to minimize late-night glucose spikes.

Physical activity behavior may be monitored by the systems described herein by detecting and/or analyzing exercise patterns including tracked exercise behavior and activity level and frequency including both aerobic and strength-based exercises. The system may use accelerometers and/or gyroscopes to track movement changes and can detect when there is little physical activity sensed, while also tracking post-prandial light exercise and monitoring whether users engage in moderate intensity exercise per day.

Sleep and circadian rhythm events may further be monitoring to assess sleep duration and quality as these represent modifiable risk factors for chronic diseases such as cardiovascular disease and diabetes. The systems may track various sleep events (e.g., excess sleep, sleep deprivation, exhaustion, etc.) and may assess how such events affect (or affected) glucose levels over a time period.

Another technical problem sought to be solved by the systems described herein is to determine which recommendations to provide to a user based on real time glucose measurements and contextual factors such as user location. Conventional systems lack the ability to dynamically adapt recommendations and nudges (e.g., prompts, information, triggers, comments or other text or images that function to generally steer a user to accomplish a goal/task) based on changing glucose levels, behaviors, and/or situational context corresponding to the user. To solve this problem, the systems and methods described herein implement an agent model (e.g., agent model 109) as a technical solution to the technical problem. The agent model is a computer-using agent that combines one or more AI models to simulate controlling computer interfaces and task performance on or for the wearable device 102. The agent model 109 can enroll trusted members, provide updates and monitoring data, and generate personalized feedback on how past and future diet, exercise, behavior, and medications may affect blood glucose levels.

The technical effect of this technical solution is the provision of personalized, context-aware recommendations and nudges to users as a basis for improving glucose management and overall health. The systems and methods described herein enable real-time adaptation of recommendations based on intermittent or continuous glucose measurements and user location. The systems integrate data from multiple sources to generate more relevant and effective nudges, and improves user adherence to health goals through personalized and timely interventions. The systems enhance the ability for users to plan ahead for patterns (e.g., patterns of glycemia, patterns of eating, etc.) that may negatively impact glucose levels and provides immediate feedback on the impact of lifestyle choices. By using AI-driven, personalized communication strategies, the systems described herein increase user engagement. These technical effects result in a more effective and user-friendly system for managing glucose levels and promoting healthier lifestyle choices, addressing limitations of conventional glucose monitoring and management systems.

In general, the sensor devices described herein may acquire whole or partial images of a target body site, including, but not limited to, venous structures and cutaneous tissues (e.g., skin surfaces). The captured image data may be processed to determine one or more optical characteristics of the venous structures, including a colorimetric value or shade, such as luminance or darkness of the venous structure(s). For example, the systems described herein may be operable to detect and quantify chromatic properties of the skin and vein tissues, including skin tone and vein coloration/saturation. The systems described herein may further analyze morphometric parameters, including but not limited to, a diameter, a cross-sectional area, and/or a volumetric capacity of the vein(s). In some embodiments, the sensor devices may evaluate surface texture attributes of the skin proximate to the veinous structures. In some embodiments, the systems described herein may detect and characterize light interaction phenomena associated with the veins, including backscattering and/or optical absorption.

Such image analysis may be performed by the systems described herein and may be representative of particular particles, elements, or glucose flowing through the veins. For example, images captured by the image sensors described herein may be analyzed to determine correlations between changes in blood glucose levels by assessing changes in the appearance of the veins in the captured images. For example, the systems described herein may determine a concentration of glucose using a near infrared (NIR) optical sensor, for example, positioned substantially adjacent to a body site of a user. In some embodiments, the systems may determine a concentration of urea by analyzing image data captured by the NIR optical sensor (or another onboard sensor 229). In some embodiments, the systems may determine a concentration of sodium by analyzing the image data captured by the NIR optical sensor (or another onboard sensor 229). In some embodiments, the systems may determine a concentration of chloride by analyzing image data captured by the NIR optical sensor (or another onboard sensor 229). In some implementations, the systems described herein may determine a concentration of potassium using the NIR optical sensor (or another onboard sensor 229). In some embodiments, the systems described herein may determine a concentration of bicarbonate based on analyzing image data captured by the NIR optical sensor (or another onboard sensor 229).

The systems and methods described herein may provide the advantages of a wearable solution that reduces or eliminates the use of needle pricks, chemical patch replacements, under skin wire applications, or the in-clinic medical testing for blood sugar assessment. While there are numerous SMBG systems available, the embodiments described herein provide advantages compared to conventional solutions of blood sugar assessment and management.

For example, while conventional methods of non-invasive measures for SMBG have shown that they can provide reliable measurements related to blood glucose levels, such methods, despite these positive results, have been limited due to technical or usability issues with the approaches. For example, conventional methods of non-invasive measures for SMBG may include componentry that may be placed in body regions that may cause the componentry to be rubbed, moved, dislodged or the like. Such componentry may fail when improperly moved or dislodged. In some embodiments, conventional componentry for SMGB may also include electrochemical portions that have to be replaced or refilled.

The embodiments described herein may function to address at least the above limitations of conventional methods of SMBG. For example, the systems and methods described herein may provide a non-invasive and wearable glucose monitor that is an affordable, instantaneous, general wellness device. This device, coupled with a software application can function to provide meaningful and actionable blood sugar and/or general health insights for a particular user wearing the device. In addition, wearing one or more of the devices described herein may promote a healthy lifestyle ultimately helping users reverse prediabetes and/or prevent T2D. The systems and methods described herein provide at least the advantages of zero medical waste, user friendly interfaces, and in general, a low barrier to adoption thereby aiding widespread adoption.

In operation, the systems and methods described herein can illuminate a body site and capture images of the body site using an image sensor, such as an NIR optical image sensor (e.g., a camera) or a camera using a red-light source, to assess near infrared light absorption and scattering. For example, the image sensor may capture images of a body site of a user wearing a device housing the image sensor. The image sensor may capture images of a combined effect of both a physiological change in a human body and a physical light scattering property at the body site. In such examples, the body site may be illuminated with a wavelength of light in the range of highest sensitivity of the NIR sensor, that is, highest quantum efficiency of the NIR sensor and the light source wavelength may range from about 700 nanometers (nm) to about 1200 nm. The captured one or more images may be of any part of the human body. For example, a body site, as used herein may include one or more of a wrist (e.g., volar, dorsal), fingers (e.g., palmar or dorsal), an arm, a knee (e.g., popliteal fossa), a palm, a leg, an ankle, a foot, toes, etc. In operation, the systems and methods described herein may analyze captured images to determine the effects of physiological changes by analyzing how the body site scatters the illuminated light.

While the systems and methods described herein utilize the infrared or the near infrared spectrum to noninvasively assess glucose levels, spectroscopic techniques are not utilized in the techniques described herein. Instead ML models are generated and used to map image content of venous blood vessels to accurate glucose levels.

For health and wellness in the prediabetes space, the conventional inputs for lifestyle change continue to be useful. For example, diet intake, activity level and frequency, sleep duration and quality, and stress level are modifiable risk factors for chronic diseases, especially for cardiovascular disease and diabetes. The systems and methods described herein may monitor or retrieve any one or more of: diet intake, activity level and frequency, sleep duration and quality, and stress level of a user wearing the device 102. The data obtained from such monitoring or retrieval may be used as an input into a generative AI model for causing changes in user behavior. The systems and methods may utilize any number of functions, tools (e.g., food logging tools, sleep monitoring tools, step or physical activity monitoring tools, stress measuring tools, etc.) and AI agentic workflows to generate recommendations for modifying one or more risk factors associated with chronic disease. Mobile device-type measurements may include one or more of: frequency of phone/app interaction and patterns of use, glucose spike patterns, frequency and timing of meals, frequency and pattern of communication via text message, email message, phone call, or voice message, location services (e.g., restaurant, game, work, home, vacation), and social networks of individuals in a same location and an associated behavior pattern.

For human behavior, any one or more of the above-recited inputs from a mobile device regarding patterns of communication and behavior, plus data on blood glucose from device 102 or another source, location, and low-burden user provided data on age, gender, comorbidities. For example, user behavior such as regularly ingesting a food type (e.g., pizza, ice cream, sugar, etc.) on a particular day and/or performing or not performing exercise on such days may be assessed by the systems described herein to determine a behavior pattern and to generate one or more suggestions, recommendations to allow the user to plan ahead for such patterns to mitigate such patterns or to enable healthier choices after the pattern occurs.

Together, with an abundance of data, the systems and methods described herein may use AI/ML techniques to generate distinct patterns of behavior, and can iterate on these patterns with increased inputs to further understand which patterns are the riskiest.

After an understanding of behavior patterns that have a higher risk of glucose spikes, the systems and methods can use LLM/AI (e.g., generative system 209, prediction system 210, and/or NNs 216) to nudge (e.g., prompt, inform, trigger, comment or steer) the consumer to move away from performing particular behaviors. For example, the systems and methods described herein may warn against drinking more than two drinks if the user is at a bar with friends at night, as this can cause a significant glucose spike. If the user is alone at home during the day and there is little physical activity sensed, LLMs or other AI models and/or agents can nudge the user to move. If being home alone is a context that has previously led to over-eating and high glucose, use of this technology may pre-emptively suggest foods high in fiber and protein instead of the high refined-carbohydrate snacks that are easiest to grab while at home. For example, the systems and methods described herein may utilize an LLM or other AI model or agent to suggest a lighter meal after a prolonged glucose spike after a meal at a restaurant.

Secondly, glucose time in range may drive the deployment of the health behavior-related nudges. The personalized portion of this process may be based on trial and error of specific tactics for each user. If post-prandial glucose is continually highly elevated after meals, the first nudges may be to decrease refined carbohydrates and increase high fiber and protein in each meal. If the user is deployed this suggestion and glucose spikes do not change for 3 days postprandially, it may suggest changing meal order (start with the vegetables and protein-based foods, end with eating carbohydrates). If that does not work, the systems and methods described herein may suggest post-prandial light exercise and nudge towards 30 min moderate intensity exercise per day. If the user gets bored of the same type of exercise daily, the systems and methods described herein may suggest a more vigorous HIIT related workout at times of the day when there is little activity, and while are unscheduled based on a calendar associated with the user.

The format of the nudges may vary: short games, popups, text messages, alerts based on blood glucose levels, prompts for logging diet intake, etc. In some embodiments, the nudges may provide an advantage of increasing user involvement and enhancing a sense of accomplishment for the user. The systems described herein may use inputs from sensors 228, 229, geolocation, user-entered data, etc. to define patterns of risk and try to sway the individual away from these risky behaviors. In some implementations, the devices and methods described herein may operate in response to user provided permissions to ensure user privacy, HIPPA privacy compliance, and the like.

In some implementations, the systems and methods described herein may employ motivational interviewing. Motivational interviewing may assist the systems described herein in capturing user-specific barriers and may direct the user towards a particular behavior change. This can be an iterative process to detect a behavior change and incrementally improve the behavior based on recommendations and/or nudges. In such examples, the systems described herein can conduct the motivational interview and generate the steps to trigger behavioral changes based on the user answers in the interview and/or prior or ongoing monitoring of the user activity or behaviors.

FIG. 1 illustrates an example high level system 100 for obtaining noninvasive glucose assessments for a body site of a user and monitoring well-being and/or glucose and generating recommendations or other content for behavioral and/or lifestyle changes. The system 100 may use images and ML techniques to detect and analyze glucose signals associated with a body site of a user to determine whether the signals are coming from interstitial fluid or blood. For example, the system 100 may use one or more noninvasive optical sensors (e.g., image sensor(s) 228) on a wearable device 102 to detect physical and physiological changes in venous blood under a skin portion of a user. In some embodiments, the wearable device 102 (and coupled image sensor(s) 228) may be positioned against (or near to or substantially near to) the body site. In some embodiments, the wearable device 102 may be worn on a body part and the body site may be placed in contact (or in near contact or in substantially near contact) to the wearable device 102.

The sensor devices described herein may include at least one image sensor (e.g., optical sensor, image capture device, camera, etc.) that may capture images of visual changes that occur in one or more veins (e.g., venous blood vessels) near to or at a surface of the body site of the user. For example, the sensors described herein may capture/observe a combined effect of both osmolality changes in an appearance of one or more veins of the body site and changes in a light absorption property of water and glucose associated with the one or more veins at the body site. These appearance changes may be used by the systems described herein to determine when a glucose level has changed for the user.

In some embodiments, the systems and methods described herein may provide a non-invasive optical sensor that detects a combined effect of both a physiological change in the human body and the physical light scattering property. Such changes/effects may be analyzed using a first machine learning (ML) model and/or a first Deep Learning (DL) model that may determine if the physical and/or physiological changes are coming from blood in the veins, for example. A second ML model (which may represent a DL model) may map the changes in blood to a glucose level. A software application executing on a computer system (e.g., computer system 1400 of FIG. 14 and/or wearable device 102 of FIG. 1/FIG. 2) may generate meaningful and actionable insights and/or recommendations for a user wearing the optical sensor and/or may provide information, insights, and/or recommendations to a health care provider, a caretaker, a buddy device 110, or the like.

The wearable device 102 may include any number of image capture devices and/or sensors to capture images of the body site. The device 102 may utilize one or more ML models 104 to discern any physiological changes in venous structures and/or skin in the images to ascertain a glucose level or glucose change in the blood associated with the body site versus a physiological change in glucose in the interstitial fluid associated with the body site. In some embodiments, the ML models 104 may map the detected changes in the blood to particular glucose levels. The wearable device 102 may obtain additional glucose signals over time by monitoring the body site. Data may be generated from the monitoring, and the ML models 104 may analyze changes over time. Such changes and data may be detected by the ML models 104 using one or more processors as described herein. The changes and/or data may be used to generate user interface content and/or data for an application that may be presented on an optional display of the wearable device 102. In some embodiments, the user interface content and/or data may be presented on a computing device 106 that is in wired or wireless communication with the wearable device 102 or a buddy device 110 in communication with the wearable device 102. The buddy device 110 may represent a device of a trusted person that a user of wearable device 104 chooses to share health data or other related device data. The computing device 106 may be a smart phone, a smart watch, a mobile gaming device, a laptop computer, a desktop computer, a cloud hosted computer, or the like.

The buddy device 110 may be a smart phone, a smart watch, a mobile gaming device, a laptop computer, a desktop computer, a cloud hosted computer, or the like. The buddy device 110 may receive output from the agent model 109 and provide insights, recommendations or the like to the user of the wearable device 102. The output may include progress notes, blood glucose or other health changes, diet selections, and the like. A buddy device 110 may access the agent model 109 as a way to enroll in receiving input from the wearable device 102 according to predefined user permissions. In some embodiments, the wearable device 102 includes the agent model 109 and automatically generates the output based on a user-configured schedule selected by a user of the wearable device 102. In some embodiments, the agent model 109 is external to device 102 and may be triggered externally by the buddy device 110 according to a buddy-configured schedule selected by a user of the buddy device 110.

In some embodiments, the agent model 109 may represent a computer-using agent that can perform tasks on behalf of a user or device. For example, agent model agent may be a computer-using agent model that combines one or more other AI models to simulate controlling computer interfaces and/or task performance. In some embodiments, the agent model 109 may use or employ generative system 209 and/or prediction system 210. In some embodiments, the agent model 109 may be outside of device 102 and may employ generative system 209*b* and/or prediction system, 210*b*. In some embodiments, the agent model 109 may execute on a separate computing device outside of systems 100, 200, but may be communicatively coupled to system 100, 200 to provide input to wearable device 102 and/or lifestyle AI coach 108.

The ML models 104, 104*a* described herein may function in conjunction with additional AI components including generative systems 209, 209*b* and prediction systems 210, 210*a* where the generative systems may function with any or all ML models 104, 104*a* to assess user behavior and user indications. The prediction systems may function with ML models 104, 104*a* to preprocess, optionally segment, analyze, and predict blood glucose levels. This ML architecture enables the system 200 to process complex physiological data and generate accurate predictions for personalized health recommendations and behavioral interventions.

Figure 2:
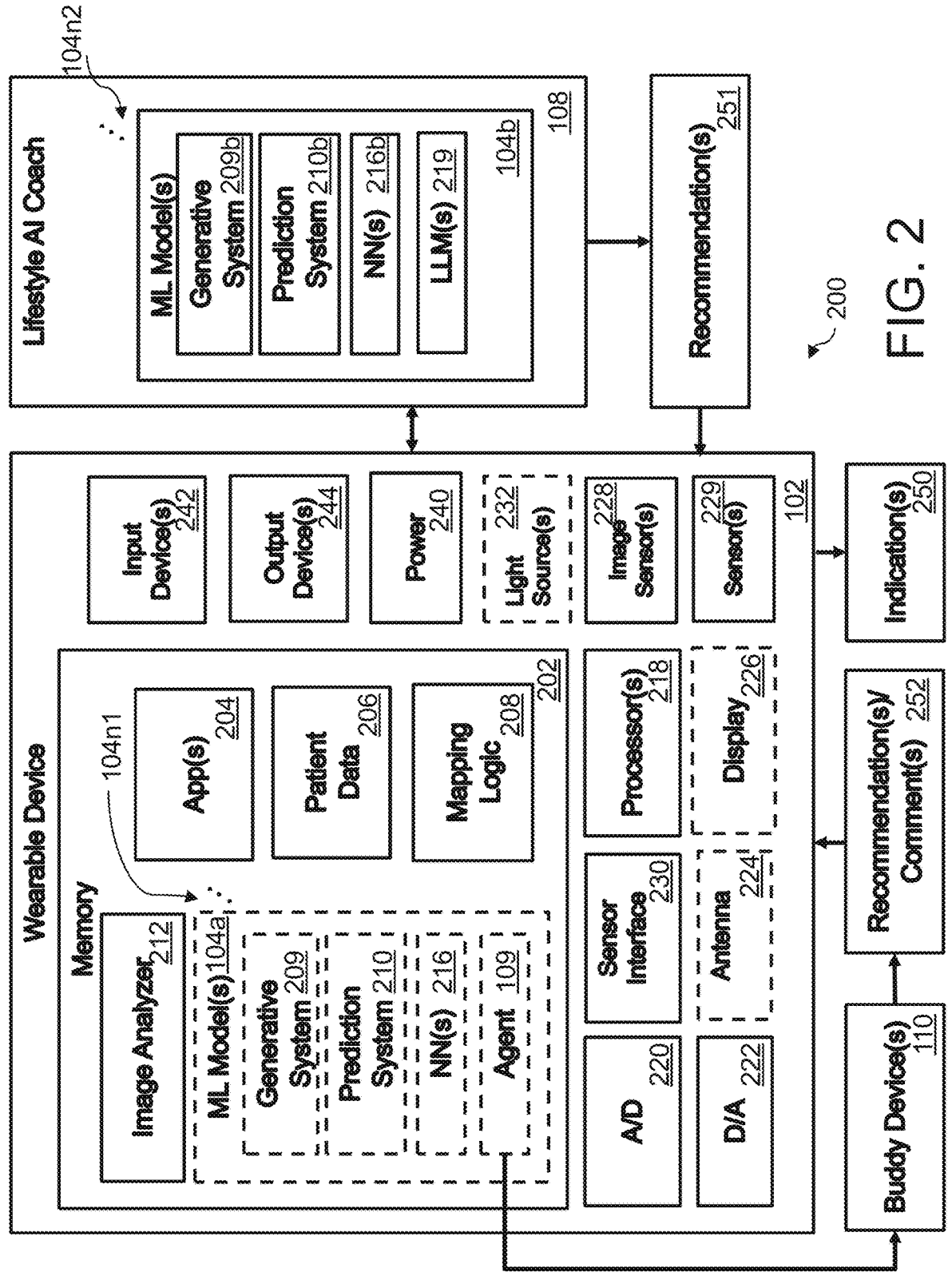
FIG. 2 illustrates a block diagram of an example system for monitoring well-being and/or glucose and generating recommendations or other content for behavioral and/or lifestyle changes.

In some embodiments, the agent model 109 may operate in a continuous loop to send instructions to be executed on a computer or browser (e.g., app). Example instructions for the agent model 109 may include requests to view updates on behavior, food intake, exercise, glucose level changes, etc. In some embodiments, the agent model 109 may capture screenshots of such data from the wearable device 102 and provide the screenshots as updates to buddy device 110. In some embodiments, the agent model 109 can take additional actions including, but not limited to triggering glucose monitoring for a time period, triggering comments, insights, and/or recommendations to be provided to the user of device 102, and/or buddy device 110. While the agent model 109 in FIG. 2 is depicted within wearable device 102, the agent model 109 may instead be external to wearable device 102, as shown in FIG. 1. In some embodiments, the agent model 109 may be part of lifestyle AI coach 108.

Some or all components of the wearable device 102 may be integrated into a band, a watch, a smart watch, an adhesive strip, jewelry, a patch, clothing, or any other wearable accessory. For example, some or all components of the wearable device 102 may be incorporated into a band or a watch or a pair of bands or pair of watches to be worn one on each arm or leg (or other appendage on the arm or leg). In some embodiments, the lifestyle AI coach 108 may operate as a server, cloud server, or other hosted computing device. In some embodiments, coach 108 may operate locally on wearable device 102 and may provide an interface in which to ask questions or otherwise inquire about future goals, shopping or food based data, exercise data, monitored data, and/or wearable device captured data. In response, the interface may generate and provide content responsive to such inquires.

In operation, the system 200 may analyze images to determine and/or monitor blood glucose changes for a user. The images may be captured by wearable device 102 and may depict a body site of the user. For example, if the wearable device 102 is a band, the body site may be a portion of a wrist, arm, ankle, leg when the band is worn on the body. The body site may include skin and a visual full or partial view of one or more venous structures.

In some embodiments, the ML models 104 and/or agent 109, in general, may utilize glucose assessments and/or user input to determine content such as recommendations, insights, and/or actionable guidance including, but not limited to maps, directions, shopping lists, educational content, menu items, or the like. The content may be provided to the wearable device 102 to give the user personalized feedback on how past and future diet, exercise, behavior, and/or medications may affect blood glucose levels so that the user may use the information to adjust lifestyle choices.

In some embodiments, such content may be generated as a basis for coaching the user to improve health metrics and/or lifestyle metrics. For example, the content may include lifestyle change recommendations that may be used as a way to lower a burden of healthful eating for a user to move the user behavior from less healthy states to more healthy states. For example, content generated by system 200 may include food recommendations and/or timing of ingesting such recommended foods. In some embodiments, recipe recommendations may be generated and provided to the user. In some embodiments, grocery store recommendations may be generated and provided to the user. In some embodiments, grocery purchase recommendations may be generated and provided to the user. In some embodiments, goods or product recommendations may be generated and provided to the user. In some embodiments, educational recommendations may be generated and provided to the user. In some embodiments, educational content recommendations (e.g., advice, links to research, details about foods, etc.) may be generated and provided to the user along with any other recommendation described herein.

In some embodiments, the system 200 may detect/determine blood glucose changes over time by analyzing the images of the body site. In response, the analysis of the changes, the system 200 may generate content, as described herein, based on the detected/determined glucose changes. In some embodiments, the content may be generated by system 200 based on user specified requests or input. In some embodiments, the system 200 may generate content according to data from wearable device 102 and/or direct requests to lifestyle coach 108 from the user using device 102.

In some embodiments, the system 200 may include or be communicatively coupled to a lifestyle coach 108. The lifestyle coach 108 may include an AI chat agent such as a large language model (LLM) 219 that may provide content that takes the form of coaching advice, lifestyle advice, recommendations, educational content, or the like based on data captured by wearable device 102 and/or data requested by a user of wearable device 102. In some embodiments, the content may include shopping recommendations, restaurant recommendations and/or corresponding educational content, as described elsewhere herein.

The system 200 may include or be communicatively coupled to one or more buddy devices 110. A buddy device 110 may represent a device of a trusted person that a user of wearable device 102 chooses to share health data or other related device data. The buddy device 110 may receive data from device 102 with permission of the user of device 102. A user of buddy device 110 may review the data and provide comments and/or recommendations 252 to encourage the user of device 102 to improve lifestyle choices and/or behaviors. In some embodiments, the buddy device 110 may function as a motivational check in and/or other process/entity capable of motivating the user to continue on an improved health path.

FIG. 2 illustrates a block diagram of an example system 200 for monitoring well-being and/or glucose and generating recommendations or other content for behavioral and/or lifestyle changes. In some embodiments, the system 200 may represent a detailed version of system 100. As shown, system 200 includes wearable device 102 communicatively coupled to a lifestyle AI coach 108 and a buddy device 110. The wearable device 102 may interact with and/or receive recommendations and coaching from coach 108. The wearable device 102 may interact with and/or receive recommendations 252 and input from one or more buddy devices 110.

In some embodiments, the system 200 may include or be communicatively coupled to a lifestyle coach 108. The lifestyle coach 108 may include an AI chat agent such as a large language model (LLM) 219 that may provide content that takes the form of coaching advice, lifestyle advice, recommendations, educational content, or the like based on data captured by wearable device 102 and/or data requested by a user of wearable device 102. In some embodiments, the content may include shopping recommendations, restaurant recommendations and/or corresponding educational content, as described elsewhere herein.

The lifestyle coach 108 may function to provide feedback on a meal just consumed by a user. The feedback may be based on detected or determined glucose responses captured by wearable device 102. In some embodiments, the lifestyle coach 108 may suggest content and/or timing of a next meal with a goal to minimize glucose spikes in the blood glucose level of the user using device 102. In some embodiments, the lifestyle coach 108 may provide feedback that includes motivating and/or incentivizing content for enabling a user to avoid glucose spikes for a set time period. The suggested time period may be based at least in part on a glucose history captured for the user by device 102, for example. The set time period may be predefined, user defined, and/or system 200 defined and may be set for about 1 day to about 10 days; about 1 day to about 2 days; about 1 day to about 3 days; about 1 day to about 4 days; about 1 day to about 5 days; about 1 day to about 6 days; about 1 day to about 7 days; about 2 days to about 4 days; about 3 days to about 4 days; about 3 days to about 5 days; about 4 days to about 5 days; about 4 days to about 6 days; about 5 days to about 6 days; about 6 days to about 7 days; about 7 days to about 8 days; about 8 days to about 9 days; or about 9 days to about 10 days.

In some embodiments, the lifestyle coach 108 may access databases of historical data for the user of wearable device 102. In some embodiments, the lifestyle coach 108 may access databases of historical data for prediabetic or diabetic users. Example databases may include, but are not limited to open-access glycemic data, which may include one or more datasets that contain glucose values from subjects with prediabetes or diabetes. The data may represent a set time period (e.g., data collected over 2-4 weeks at regular intervals of 5 minutes, with diet intake and mealtimes documented). Other user-specific or user-agnostic databases may be utilized. The databases accessed may include glucose values collected for shorter or longer time periods. The databases may represent glucose value captures performed intermittently or with a continuous glucose monitor.

The historical data may be used to generate recommendations, content, or other insight. For example, the lifestyle coach 108 may be programmed to perform intermittent checks with instructions such as 'If the user is found to have high postprandial glycemia of 140-199 mg/dL two hours after a meal, recommend the user to increase protein and healthy fat intake in the next meal, and eat these food components before a small portion of complex carbohydrates. Keep this recommendation in your non-parametric memory when suggesting menu items from the user-provided restaurant or while recommending grocery items. Ask the user to set reward goals at the beginning of each week. Some example reward goals are a dessert with suspension of the measurement of post-prandial glycemia akin to a cheat dessert after 3 days of glycemic control or a manicure after 5 days of controlled glycemia. Nudge the user to achieve these rewards with progressive, adaptable goals for glycemic control.' Other instructions are of course possible, as one of skill in the art will appreciate.

In some embodiments, the blood glucose data may be obtained from a known database of multiple users or from a historical record of data of a particular user. The system 200 may be prompted/triggered to perform particular tasks based on received, monitored, or otherwise detected blood glucose. For example, if a user is found to have high postprandial glycemia of about 140-199 mg/dL about two hours after a meal, the system 200 may recommend the user to increase protein and healthy fat intake in the next meal, and eat these food components before a small portion of complex carbohydrates. The system 200 may also be prompted or programmed to keep these types of recommendations in non-parametric memory when suggesting menu items from a user-provided restaurant or while recommending grocery items, for example. The system 200 may also be prompted or programmed to ask the user to set reward goals at the beginning of each week. Some example reward goals include a dessert with suspension of the measurement of post-prandial glycemia akin to a cheat dessert after 3 days of glycemic control or a manicure after 5 days of controlled glycemia, for example. The system 200 may be further prompted or programmed to nudge the user to achieve these rewards with progressive, adaptable goals for glycemic control.

In some embodiments, the system 200 implements a lifestyle AI coach (e.g., lifestyle AI coach 108) that generates and provides personalized health recommendations, with a focus on glucose management. To do so, the system 200 may utilize one or more Application Programming Interface (API) keys to import libraries, databases, and/or functions to enable personalized health assessments and recommendation generation. These may include APIs for accessing external services such as mapping and restaurant information databases, web scraping, online shopping platforms, etc.

At a high level, the system 200 may define and utilize a set of software functions for interacting with external services. For example, a get_grocery_stores function may be used to find nearby grocery stores based on a provided ZIP code. In some embodiments, the system 200 may define and utilize a sum_item_prices function may be used to adjust a list of items to fit within a specified budget. In some embodiments, a get_restaurant_dishes function may be used to retrieve menu items or other purchasable items for a specified restaurant or other venue. In some embodiments, the system 200 may define and utilize a check_restaurant_menu_availability tool to check if a particular restaurant menu or storefront is available to access through system 200. The tool may function when the user is dining out to analyze a restaurant menu in real time, and suggest modifications to dishes that could help maintain stable glucose levels.

In some embodiments, the lifestyle AI coach 108 is a conversation agent that utilizes one or more language models. This agent may initialize with a system 200 prompt that defines the coach role and capabilities. In addition, the agent may use memory 202 to maintain conversation history. Further, the agent may implement a conversation chain that processes user input and generates responses.

In some embodiments, the system 200 may implement and/or generate a user interface (e.g., shown in FIGS. 17A-18D. The user interface may be a web interface or an app interface (e.g., apps 204). The interface may display logos, application titles, menus, conversation history containers, input fields, and response fields.

In some embodiments, the lifestyle AI coach 108 may recommend nearby grocery stores and healthy food items based on a determined user location. The coach 108 may suggest healthy menu options from restaurants, provide personalized health advice based on glucose levels and user behavior, adapt recommendations based on user location and context, and/or generate nudges or messages to encourage healthy behaviors.

The system 200 integrates various data sources to provide comprehensive recommendations responsive to user input received through the lifestyle AI coach interface 108 and/or directly through the wearable device 102. The data sources may include glucose measurements, which may be simulated or determined and sent by wearable device 102 or another wearable device coupled to device 102. The data sources may further include location data to enable provision of context-aware recommendations by system 200. The data sources may further include restaurant and/or grocery store information obtained from external databases and/or scraped online sources.

The system 200 employs artificial intelligence techniques to analyze patterns in user data and generate personalized recommendations. This may involve machine learning models trained on health and nutrition data, glucose data, and/or user-specific health data.

In some embodiments, the system 200 may include or be communicatively coupled to one or more buddy devices 110. A buddy device 110 may represent a device of a trusted person that a user of wearable device 102 chooses to share health data or other related data. The buddy device 110 may have access to data provided by wearable device 102 through agent model 109. Access is provided according to user selected privacy conditions configured by a user of wearable device 102.

The agent model 109 may represent an agent that can control portions of data from wearable device 102 and/or particular actions performed by (or associated with) wearable device 102. For example, the agent model 109 may be a computer-using agent that can perform tasks on behalf of a user or device. In some embodiments, the agent model 109 may be a computer-using agent model that combines one or more other AI models to simulate controlling computer interfaces and/or task performance of wearable device 102. The agent model 109 may function to enroll a trusted member (e.g., user, user device, etc.) and may cause device 102 to provide updates and/or monitoring data such that the trusted member may use such updates and/or data to provide accountability for goals of the user associated with wearable device 102.

In a non-limiting example, the agent model may function as an automated agent to obtain progress data, monitoring data, or the like from wearable device 102. Such data may include obtaining glucose levels for a user, summarizing the data, and sending such glucose data to the buddy device 110. In some embodiments, the data is not summarized, but instead sent as a screenshot, value, or interface depicting a portion of monitored data pertaining to the user of device 102. The agent model 109 may receive feedback from a user of the buddy device 110 through an interface that communicatively couples the agent model 109 to the buddy device 110. The agent model 109 functions to operate as an agent for the wearable device 102 (e.g., a band) and/or as an agent for a device (e.g., smart watch, phone, etc.) communicatively coupled to device 102. The agent model 109 can send data as messages from the buddy device 110 to the wearable device 102 and may receive responses from the buddy device 110 and the wearable device 102. In some embodiments, the agent model 109 may include or have access to databases, data, web scrapes, or the like in order to provide content, updates, or other requested information to the wearable device user and/or the buddy device user. In this example, the user of the wearable device 102 may provide permission to the agent model 109 to share updates and/or health data with a selected one or more buddy devices 110. Future updates and/or data sharing from the device 102 to the one or more buddy devices 110 may be automatically performed by the agent model 109 according to user enabled permissions. In some embodiments, the agent model 109 may be used by a user of the buddy device 110 to offer feedback or encouragement to the user based on what the agent model 109 provided to the buddy device 110 as an update.

In some embodiments, the agent model 109 may function to find and provide options to the user of wearable device 102. For example, the agent model 109 may analyze a current location for the user and glucose trends corresponding to the user to suggest nearby restaurants with menu items suitable for maintaining stable blood glucose levels. If the user is at work, the agent model 109 may recommend healthier alternatives to common vending machine snacks. When grocery shopping, the agent model 109 may provide real-time suggestions for lower glycemic index alternatives as the user scans or selects items.

In some embodiments, the agent model 109 may function to provide an automated end-to-end ordering process for food, groceries, supplies, or other purchasable items. For example, if the glucose levels for the user are detected to indicate that the user may benefit from more fiber, the agent model 109 may generate a shopping list of high-fiber foods, locate these items at nearby grocery stores, compare prices, place items in an online shopping cart and/or place an order for delivery or pickup. Similarly, if the user frequently skips meals due to a busy schedule, the agent model 109 may suggest and order healthy meal kit deliveries that align with the glucose management goals corresponding to the user.

In some embodiments, the agent model 109 may provide real-time updates on ingredients, menu items, suggestions, grocery store inventory, etc. For example, if a user is dining out, the agent model 109 may analyze the restaurant menu in real-time, suggesting modifications to dishes that could help maintain stable glucose levels. The agent model 109 may also alert the user to new low-glycemic products available at a predefined or selected grocery store. During seasonal changes, the agent model 109 may update recommendations to include seasonal produce that can positively impact glucose management. If a user is determined to have a favorite healthy item and that item is out of stock, the agent model 109 may immediately suggest alternatives with similar nutritional profiles.

In some embodiments, the lifestyle coach 108 may ask the user for contact information for a buddy device 110 (e.g., email, phone number, etc.). In some embodiments, the agent model 109 may suggest particular users in a contact list of a wearable device user. The suggested users may be suggested to function as a buddy device 110. A messaging agent may share the same guidelines and incentives, proposed by the LLM, with the trusted member. The message may help the buddy understand how particular support may help the user. The messaging agent (e.g., agent model 109) may also share progress associated with the user. Using the function calling ability of the LLM, the LLM may call a web-searching API to find places/stores that would be of interest to the trusted member that is also in the vicinity of the recommended grocery store, if that trusted member is responsible for groceries and/or cooking.

As shown in FIG. 2, the wearable device 102 includes memory 202 for storing program instructions and data that may be used and/or generated by processes carried out by the wearable device 102. The memory 202 may store and execute instructions associated with applications (e.g., apps) 204, patient data 206, mapping logic 208, generative system 209 and/or generative system 209$b$, prediction system 210 and/or prediction system 210$b$, image analyzer 212, ML models 104$a$, 104$n$1 and/or ML models 104$b$, 104$n$2, and/or neural networks 216, 216$b$. The processors 218, the analog to digital converter 220, the digital to analog converter 222, the optional antenna 224, and the optional display 226 may also interface with memory 202 and/or apps 204, patient data 206, mapping logic 208, generative systems 209, 209$b$, prediction systems 210, 210$b$, image analyzer 212, ML models 104, and/or neural networks 216, as described in detail below. While the ML models 104$a$ are depicted as executing on the wearable device 102, other implementations may provide ML models external to system 200. In some embodiments, the ML models 104$a$ may be replaced with external models 104$b$, which may operate in lifestyle AI coach 108 (or another computing device communicatively couplable to device 102 or coach 108).

The wearable device 102 may include one or more sensors for detecting physiological parameters of the user. For example, the wearable device 102 may include one or more image sensors 228 for obtaining visually-identified glucose measurements, for example. In some embodiments, the wearable device 102 may include one or more sensors 229 that include inertial measurement units such as accelerometers and/or gyroscopes to track movement changes, temperature sensors to track user temperatures. Other sensors and/or elements may be incorporated into or near to the device 102. For example, other optical, electrical, and/or mechanical sensors 229 may also be included in device 102 to measure any number of physiological parameters of a user wearing device 102. In some embodiments, the image sensors 228 may include one or more of: a light source, a red-light source, an IR light source, or a near infrared (NIR) light source for illuminating a body site.

In operation of device 102 using sensor(s) 228, incident light undergoes reflection, absorption, and scattering that may be captured by the image sensor(s) 228. For example, the reflected light arrives at the image sensor 228 (e.g., a camera lens). The camera lens focuses the reflected light onto the sensor which then produces an image that is captured using software described herein. The digital image is stored on a persistent storage medium for later use by components of wearable device 102 and/or other computing device(s) communicatively coupled to device 102.

In some embodiments, glucose measurements may be obtained using an optical sensor (e.g., one or more image sensors 228) that is integrated into or associated with the wearable device 102. For example, the device 102 may include one or more image sensors for detecting a combined effect of osmolality changes in one or more veins of the user by assessing an NIR light absorption property of water and a scattering property of glucose in the veins. In some embodiments, the image sensor 228 may be an NIR camera that captures images of veins in a body site of the user wearing device 102. In such an example, the image sensor 228 may operate with an optional light source 232 with a wavelength that ranges from about 700 nm to about 1000 nm. In some embodiments, the light source may be a red-light source with a wavelength of about 620 nm to about 750 nm. In some embodiments, the optional light source 232 may be integrated into the image sensor 228. In some embodiments, the optional light source 232 may be separate from image sensors 228, but may be installed within wearable device 102. In some embodiments, the device 102 may be communicatively coupled (e.g., via antenna 224) to an external sensor (not shown) that is not housed in or integrated into device 102. In such examples, the external sensor may provide data (e.g., images, measurements, etc.) to wearable device 102 to determine particular outputs, such as glucose levels, glucose predictions or related predictions, and/or other measurements obtained at a body site of the user wearing device 102 and/or the external sensor. In such examples, the external sensor may be part of a watch face while device 102 represents a watch band. The sensors onboard device 102 may interface with and otherwise communicate with external sensors onboard a peripherally connected or wirelessly connected other device.

In some embodiments, the sensors 228 and/or other sensors in communication with wearable device 102 may be coupled to a sensor interface 230. The sensor interface 230 may store instructions to carry out operations pertaining to received sensor signals from one or more of the sensors 228, 229. For example, the instructions may enable interaction with memory 202, one or more processors 218, and/or sensors 228 to communicate sensor data from one or more of the sensors 228, 229 to the wearable device 102. The sensor data may be obtained from the sensors 228 in the form of recordings, measurements, images, and/or audial information.

Referring again to FIG. 2, one or more ML models 104a may be optionally installed on wearable device 102. The one or more ML models 104a may include a generative system 209a, a prediction system 210a, and one or more neural networks 216a. The ML models 104a may include any number of ML models. A first ML model 104 (e.g., ML model 104a) may perform a first set of functions and a second ML model (e.g., ML model 104n1) may perform a second set of functions. In some embodiments, the wearable device 102 may utilize ML models on a server and/or other device external to wearable device 102. For example, the wearable device 102 may utilize ML model 104b and/or ML model 104n2 on lifestyle coach 108. The ML models 104b, 104n2 may include a generative system 209b, a prediction system 210b, and one or more neural networks 216b. The ML models 104b, etc. on coach 108 may include or provide access to any number of ML models. A first ML model (e.g., ML model 104b) may perform a first set of functions and a second ML model (e.g., ML model 104n2) may perform a second set of functions.

In general, the ML models 104 (e.g., 104a, 104b, 104n1, 104n2, etc.) described herein may include any number of neural networks 216 (e.g., neural networks 216a, 216b, etc.) that are programmed to learn to determine levels of glucose in a vein, for example, by analyzing images of example veins (e.g., training data) at different levels of abstraction in order to determine levels of glucose in images of veins provided to the ML model after the training of the model, for example. In general, the neural networks 216a, 216b, etc. can model complex non-linear relationships amongst inputs to learn how to analyze new inputs. The neural networks described herein may include or use one or more machine learning algorithms to learn from training data and apply that learning to new inputs. The learning may take the form of modeling high-level abstractions in data.

In the examples described herein, the ML models 104 may be trained with training data including images of one or more veins of a user and with data representing glucose measurements, sodium measurements, and/or potassium measurements associated with blood of the respective user. For example, the ML models 104 described herein may be trained using (1) a collection of labeled data from clinical study participants to analyze a relationship between glucose, sodium, and/or potassium measurements associated with such study participants, (2) lab generated data values from a basic metabolic panel (BMP) testing and/or analysis. In some embodiments, an example clinical study may include at least about 20 to about 60 participants that are provided a controlled meal prior to a blood draw. Then, blood from a vein for each participant may be sampled (e.g., drawn at regular intervals of about 10 to about 15 minutes for about 3 hours). These blood samples can be run through a lab for BMP testing and/or analysis to obtain a reference value of each participant's blood glucose, sodium, potassium, and blood urea nitrogen (BUN), or other patient data 206, for example. The ML models 104 may be trained and tested to output a glucose value (or range) for a user wearing the wearable device 102, for example, based at least in part on elements (1) and (2) above. Although a single clinical study is described, any number of clinical studies and/or any amount of simulated data may be used to train and/or test the ML models 104.

In some embodiments, the training may include augmentation of datasets used for training. For example, training data may include preprocessing of data used for training. Preprocessing may include, but is not limited to resizing, rescaling, sampling, cropping, rotating, flipping, de-noising, etc. one or more of the images in the training data. In some embodiments, training data may include synthesized new data based on plausible and tested real-life scenarios for a particular user or a population.

In a non-limiting example, the ML models 104 may include a first ML model 104 (e.g., ML model 104a or 104b, etc.) arranged to perform semantic segmentation on images to detect veins (e.g., portions of venous blood vessels). The first ML model 104 may perform image segmentation to partition a digital image into multiple segments. This segmenting process may simplify and/or modify a representation of the digital image as a basis in which to locate particular objects, boundaries, or the like within the images. For example, the segmenting process may be performed to identify one or more venous blood vessels and/or venous blood vessel portions within a body site adjacent to the wearable device 102.

In general, the segmenting process may include dividing up one or more digital images (e.g., representing a capture of IR reflections by sensor 228) and analyzing the one or more digital images. The analyzing may result in identifying particular pixels/voxels in the images and/or applying labels, indicators, markers, or other indications on particular pixels/voxels. In some embodiments, identifying and/or labeling pixels/voxels may pertain to venous blood vessels and/or particular changes in an appearance of such blood vessels. In some embodiments, identifying and/or labeling particular pixels/voxels may pertain to particular changes in light scattering behavior detected from the blood vessels. In some embodiments, identifying and/or labeling particular pixels/voxels may pertain to particular changes in osmolality changes associated with the digital images of the blood vessels. In some embodiments, identifying and/or labeling particular pixels/voxels may pertain to detecting a reduced scattering coefficient detected in the digital images of the blood vessels.

In some embodiments, segmenting and labeling the digital images may allow that particular features or characteristics in the segmented images be mappable back to features in a corresponding captured image in which the segmented images were derived. In some embodiments, the segmenting process may be used to train the first ML model 104 to segment structural features of blood vessels captured in images by wearable device 102.

The first ML model 104 may be one of several ML models within the ML models 104. The first ML model 104 may include a suitable convolutional neural network (CNN) architecture such as a UNET, EFFICIENTNET, RESNET, FR-UNET, Swin-UNETR, OCTA-NET, V-Net, DeepLab, FCN, etc. It is noted, selection of an ML model may self-select the hardware upon which the ML model may be executed. For example, ML models that utilize greater computational resources may not be executed on a mobile device (i.e., the mobile device does not have enough processing power) and instead may be executed on a server and/or desktop. However, it is contemplated that mobile device hardware may improve to become suitable for those ML models that utilize greater computational resources. The first ML model 104 may be trained to segment venous blood vessel images and may be understood to include a collection of weights and biases for neurons established during training and details of hyperparameters such as the learning rate associated with the ML model. In some embodiments, patient data 206 may be used as training data in the event that the user (i.e., the patient under test) has approved the use of such data.

A second model 104 (e.g., ML model 104*n*1 or ML model 104*b*, etc.) may receive the output (e.g., segmented images of one or more veins) of the first model as input and may perform a classification of the images. For example, a second model in the ML models 104 may include a suitable architecture, e.g., CNN (e.g., such as one or more deep learning networks), logistic regression, decision trees, random forests, support vector machines, Naive Bayes, K-nearest neighbor (KNN), etc. that may be used for classification of the segmented images into classes of glucose measurements having a range of about 5 mg/dL. The second ML model 104 may be trained to assess venous blood vessel images for blood glucose, sodium, bicarbonate, and/or potassium and may be understood to include a collection of weights and biases for neurons established during training and details of hyperparameters such as the learning rate associated with the ML model. In some embodiments, patient data 206 may be used as training data in the event that the user (i.e., the patient under test) has approved permission of the use of such data.

In some embodiments, the classification may be based on particular classes (e.g., categories) of glycemia associated with the glycemic index of food. In one non-limiting example, a size of each class may be chosen to be about 5 mg/dL per class. However, the total number of output classes utilized by device 102 and ML models 104 may be selected based on the size of each class. For example, the total number of output classes may be determined based on a clinically significant glucose range of about 54 mg/dL to about 250 mg/dL and a range of glucose values obtained from training data. In some embodiments, the number of output classes may be based on predetermined glucose ranges that are clinically significant. In some embodiments, the classification of the segmented images may be classified by the first ML model into classes selected based on one or more clinical trials. Such trials may collect (from each participant in a particular trial) images of venous blood vessels and corresponding blood samples at a same time window and/or before/after the time window. The blood samples may be tested for glucose, potassium, sodium, and/or BUN by a laboratory. Features in the images may be compared to levels of glucose, potassium, sodium, and/or BUN in the blood. Assessments may be made to generate the categories of glycemia. In some embodiments, the categories may be generated and subcategorized according one or more of subject age, disease status, weight, medication status, skin tone, skin thickness, gender, ethnicity, temperature, tracked food intake, stressor(s)/stress level(s), etc.

Upon completion of classification, the training of ML models 104 may be considered completed such that the ML models 104 can be used to infer a range of glucose values (e.g., mg/dL), given a sensor output from one or more sensors 228, for example.

In some embodiments, the ML models 104 may be expanded and trained to predict a range of glucose values according to a panel of metabolic readings, including, but not limited to potassium, sodium, and/or BUN, to provide an overall representation of current metabolic status related to prediabetes, for example. In some embodiments, the ML models 104 may be programmed to determine a maximum achievable accuracy, sensitivity, and/or specificity for glucose, potassium, sodium, and/or BUN values. Other patient data 206 may also be used for particular calculations and/or related predictions generated by device 102 when the user (i.e., the patient under test) has provided permission for the use of such data.

Example ML models 104 may include a CNN architecture that executes using two or more graphical processing units. For example, a CNN architecture like EFFICIENTNET or RESNET model may be used. In some embodiments, pre-training one or more of the ML models 104 with IMAGENET may be performed to assess and/or improve the accuracy of the output of one or more of the ML models 104. Bias, variance, and error analysis may be performed, on the development set, and appropriate model hyperparameters can be fine-tuned to iteratively increase the performance of the ML models 104. Further, different layers of the neural networks 216*a*, 216*b* can be introspected to understand what the different hidden units in both the shallow and deep layers of the networks are learning or computing. Information from neural network introspection may also be used to improve the performance of one or more of the ML models 104. Data visualization may be performed using suitable dimensionality reduction techniques, e.g., SNE, t-SNE, UMAP, etc, for example, to understand how the output data is clustered and whether there are gaps in the output data.

In some embodiments, the performance of the ML model may be assessed (or results may be displayed) by an app 204 or server/cloud device (not shown). The assessment may evaluate according to any or all of the following elements: sensitivity, specificity, true/false positive, and true/false negative. The sensitivity element may refer to a probability of a positive test, conditioned on truly having a condition such as prediabetes, diabetes, etc. (or tested positive by a predefined test level if the true condition cannot be known). The specificity element may refer to a probability of a negative test, provided one does not have the condition. The true positive element may represent a test result that correctly indicates the presence of a condition or characteristic. The true negative element may represent a test result that correctly indicates the absence of a condition or characteristic. The false positive element represents a test result which wrongly indicates that a particular condition or attribute is present. The false negative element may represent a test result which wrongly indicates that a particular condition or attribute is absent.

In some embodiments, one or more user interfaces may be provided on the optional display 226 of wearable device 102 and/or another computing device coupled to wearable device 102. The user interfaces may be textual, tactile, audial, and/or graphical and may be displayed in one or more apps 204. The apps 204 may provide information (via the user interfaces) to support user self-monitoring with the intention of influencing health decisions to prevent the development of prediabetes and/or T2D. In some embodiments, one or more apps 204 may trigger for the sensor 228 to capture one or more images. The one or more images may then be sent to an external computing device (e.g., cloud server, mobile phone, computing system 1400, or the like) for further assessment and machine learning-based predictions. Any predicted results (e.g., glucose results, potassium results, sodium results, etc.) may be provided back to the app 204, which may cause display of such results on wearable device 102 (or another computing device external to device 102). In some embodiments, one or more apps 204 may trigger for the sensor 228 to capture one or more images. The one or more images may then be analyzed by wearable device 102 to perform assessment and machine learning-based predictions. Any predicted results (e.g., glucose results, potassium results, sodium results, etc.) may be provided via the app 204, which may cause display of such results on wearable device 102 (or another computing device external to device 102).

In some embodiments, an app(s) 204 may provide graphical content showing a current glucose, sodium, potassium, and/or BUN range for a user wearing device 102. For example, the app 204 can provide a graphical plot of one or more values throughout a time period, for example a day. This graphical plot and/or view may also mark hyper- and hypo-glycemic boundaries. In some embodiments, the apps 204 may provide a number to serve as a surrogate for good glycemic control and set targets for the user to help achieve specific glycemic control ranges. These targets can be set in an incremental way such that the user is able to gradually change behavior to achieve realistic and lasting lifestyle changes. In some embodiments, the apps 204 may be synchronized with a third party health app to provide users a holistic view of user-based glucose, metabolites, diet, and/or activity, just to name a few examples.

In general, the apps 204 may be used by a user of the wearable device 102 to interface with output from ML models 104, sensors 228, generative system 209, prediction system 210, image analyzer 212, and mapping logic 208. In some embodiments, at least one of the apps 204 may provide a trigger for a sensor (e.g., sensor 228) to capture data, send the captured data to an online storage medium (e.g., a cloud server) for ML processing and/or prediction system processing, and push the predicted results back to the app 204. The app 204 may then display the predicted results on the optional display 226, and/or may display results on another computing device display.

In some embodiments, the apps 204 may include an AI application for coaching or assisting a user with lifestyle choices. For example, the lifestyle AI coach 108 may execute as an app 204 on device 102 and may utilize data from the wearable device 102, user inputs, and external sources to provide personalized guidance. The AI coach 108 may analyze patterns in glucose levels of the user, correlating them with diet, exercise, sleep, and stress data to identify factors influencing glucose management. Based on this analysis, the coach may generate tailored recommendations, such as suggesting specific meal compositions to minimize post-prandial glucose spikes or recommending optimal times for physical activity to improve glucose control.

In some embodiments, the AI coach 108 may also adapt to a selected or predefined communication style and frequency based on user preferences and engagement levels. For example, the AI coach 108 may use motivational interviewing techniques to help users overcome barriers to behavior change, asking open-ended questions and providing reflective feedback. The AI coach 108 may employ different strategies for different users. For example, the AI coach 108 may use gamification elements for those motivated by competition, or may provide detailed scientific explanations for users that prefer to understand the underlying mechanisms of glucose regulation.

In some embodiments, the AI coach 108 may anticipate potential challenges and proactively provide strategies to maintain healthy behaviors for a user. For example, if a calendar associated with the user indicates an upcoming business trip, the AI coach 108 may offer tips for managing glucose levels while traveling, including restaurant recommendations and strategies for staying active. The AI coach 108 may also integrate with other apps and services, such as suggesting recipes that align with user health goals and may, for example, automatically add ingredients to a shopping list. By providing continuous, personalized support, the AI coach 108 aims to make sustainable lifestyle changes more achievable for users managing glucose levels.

In operation of system 200, analysis performed may be representative of particular particles, elements, or glucose flowing through the veins. For example, the systems described herein may determine a concentration of glucose using an optical sensor, such as an NIR optical sensor positioned substantially adjacent to a body site of a user. In some embodiments, images captured by the image sensors described herein may be analyzed by system 200 to determine correlations between changes in blood glucose levels by assessing changes in the appearance of the veins in the captured images.

In some embodiments, the system 200 (e.g., wearable device 102) may determine a concentration of urea by analyzing image data captured by the NIR optical sensor (or another onboard sensor). For example, the system 200 may detect changes in the optical properties of the venous structures that correlate with urea concentration. In this instance, specific NIR spectrum wavelength(s) may be utilized to determine the absorption characteristics of urea exist and determine intensity of the light. This information can be used in conjunction with determined glucose data to provide a comprehensive assessment of the metabolic state of the user. The system 200 may alert the user if urea levels indicate potential kidney function issues or dehydration, prompting (e.g., nudging) the user to increase fluid intake or seek medical advice.

In a non-limiting example, the system 200 may detect changes in a darkness of the veins, which may be attributed to the NIR light interactions. The higher the glucose concentration, the lower the scattering coefficient of NIR photons and the darker the veins, corresponding to fewer photos returning back to the sensor 228. The changes in the size and volume of the veins may be attributed to the osmolality changes. The higher the glucose concentration, the higher the osmolality and larger the size or volume of the veins, corresponding to water flow into the veins.

In some embodiments, the systems may determine a concentration of sodium by analyzing the image data captured by the NIR optical sensor (or another onboard sensor). For example, the system 200 (e.g., wearable device 102) may detect subtle changes in tissue fluid balance and blood vessel characteristics that correspond to sodium levels. Users can use this information to manage hypertension and/or heart conditions alongside diabetes or prediabetes conditions. The AI coach 108 may use the data to provide tailored dietary recommendations, such as suggesting low-sodium alternatives or advising on optimal hydration strategies based on the detected sodium levels and activity patterns of the user.

In some embodiments, the systems may determine a concentration of chloride by analyzing image data captured by the NIR optical sensor (or another onboard sensor). For example, the system 200 (e.g., wearable device 102) may identify osmolality changes associated with chloride ions in the bloodstream. In some embodiments, particular NIR optical sensors may be utilized for particular determinations. For example, for chloride ion determination a suitable porphyrin based sensor such as 5, 10, 15, 20-Tetrakis (4-hydroxyphenyl) porphyrin (THPP) may be used. Chloride levels can also provide insights into an electrolyte balance and hydration status of the user. The AI coach 108 may use this information to fine-tune recommendations for fluid intake. This can ensure that users engaged in intense physical activity or those living in hot climates are provided a recommendation based on context of the body engagement and location.

In some implementations, the systems described herein may determine a concentration of potassium using the NIR optical sensor (or another onboard sensor). For example, the system 200 (e.g., wearable device 102) may detect changes in the electrical properties of tissues that correlate with potassium levels. For example, utilizing a specific NIR spectrum wavelength (e.g., spectral range between about 900 nm to about 1700 nm) sensitive to the presence and concentration of potassium. This measurement may provide a potassium monitoring mechanism for users taking certain medications that affect potassium balance. The AI coach 108 may provide alerts if potassium levels approach concerning thresholds and may offer dietary suggestions to maintain optimal potassium levels, such as recommending potassium-rich foods when levels are low or advising caution with high-potassium foods when levels are elevated.

In some embodiments, the systems described herein may determine a concentration of bicarbonate based on analyzing image data captured by the NIR optical sensor (or another onboard sensor). For example, the system 200 (e.g., wearable device 102) may detect subtle changes in blood pH levels reflected in the optical properties of venous structures. For example, utilizing a specific NIR spectrum wavelength (e.g., spectral range between about 700 nm to about 2500 nm) sensitive to the pH levels. Bicarbonate levels can provide insights into an acid-base balance in the body, which can help to assess overall metabolic health. The AI coach 108 may use this information to provide guidance on dietary choices that support optimal pH balance, such as suggesting alkaline-forming foods if bicarbonate levels are low, or advising on strategies to mitigate metabolic acidosis in conjunction with glucose management.

Referring again to FIG. 2, the image analyzer 212 may receive images (e.g., image data) from one or more image sensors 228 (e.g., an NIR sensor). The received images may include data representing one or more digital images capturing a body site of a user wearing device 102. The image analyzer 212 may assess the images to measure and/or detect both physical and physiological changes under human skin, such as within veins and in particular, venous blood. The physical and/or physiological changes in a vein responsive to IR light, for example, may be used by device 102 to ascertain changes in glucose for the user wearing device 102. For example, utilizing a specific NIR spectrum wavelength (e.g., spectral range between about 700 nm to about 2500 nm, about 900 nm to about 2000 nm, about 1000 nm to about 1800 nm, etc.) sensitive to the glucose molecules. For example, the changes in the darkness of one or more veins at the body site may be attributed to IR light interactions between the sensor 228 and the body site. Changes in the size and/or volume of the one or more veins at the body site may be attributed to osmolality changes.

In general, osmolality represents a colligative property of a solution (including body fluid) that indicates the concentration of all the particles dissolved in the solution. Assessing osmolality using IR light, as described herein, can allow for determination of glucose changes in venous blood within a vein at a body site. In human blood serum or blood plasma, osmolality depends on the concentration of five major osmotic solutes. Three of the five osmotic solutes are of ionic nature (i.e., $Na+$ (sodium ion), $Cl-$ (chloride), $HCO3-$ (bicarbonate)). The final two osmotic solutes are non-ionic (i.e., glucose and urea). Water normally flows from a compartment of low osmolality to a compartment of high osmolality and this occurs if a membrane between the two compartments is permeable to water. When water moves between plasma and intracellular compartments, the movement direction depends on the osmolality of both compartments. For example, if a cell is in a relatively hyperosmolar solution, fluid will move out of the cell towards the highly concentrated compartment to reach homeostasis. As a result, the cell will shrink. There are many ways to estimate serum osmolality utilizing the basic metabolic panel test to measure sodium, glucose, potassium, and/or blood urea nitrogen.

In addition, water absorption in the shorter NIR wavelengths is typically lower (e.g., about $0.004 \text{ mm}^{-1}$ to about $0.04 \text{ mm}^{-1}$). Tissue penetration in the shorter NIR wavelengths is typically higher (e.g., about 2 mm to about 3 mm). Both together make this wavelength range suitable for sensing in humans. Clinical measurements corresponding to embodiments shown in FIGS. 4A-12D indicate a good correlation between reduced scattering coefficients of intracellular mediums and extracellular mediums in the NIR range and the concentration of glucose as determined from a conventional blood test of glucose.

The majority of glucose in the human body is found within interstitial fluid (i.e., between cells), rather than being contained in blood. Accordingly, the embodiments described herein may discern a location of one or more veins, determine where the one or more veins are located in relation to surrounding tissue, and perform analysis on changes over time in such veins and surrounding tissue. In addition, water also has a strong absorption spectrum in the NIR wavelengths. However, interference from water may be avoided by the embodiments described herein due to the ability of the wearable device 102 to discern veins from other tissues of the body. Further, under normal bodily function circumstances, the concentration of water in venal blood remains steady and thus is unlikely to interfere with assessments performed by the device 102 on captured images of the one or more veins.

Since glucose levels fluctuate immediately with food intake but sodium levels do not typically fluctuate immediately with food intake, changes in osmolality may predominantly reflect changes in blood glucose. Thus, the image analyzer 212 can obtain and analyze images and/or image data and provide such image data and analysis to one or more ML models 104. In some embodiments, one or more ML models 104 can preprocess (e.g., resizing, rescaling, sampling, cropping, rotating, flipping, etc.) the images before the image analyzer 212 analyzes the images. In some embodiments, the image analyzer 212 is a module within an ML model 104 and may function as an image analyzer algorithm for the ML model 104.

The generative system 209 may function with any or all ML models 104 to assess user behavior and user indications 250, for example, as a basis in which to generate recommendations 251 for improving such user behavior with respect to disease states. The recommendations 251 may be based on observations and/or predictions generated by system 209, system 210, or other model 104 associated with device 102, band 1500, band 1550, or the like. In some implementations, the recommendations may be based on observations assessed via other devices or input by the user at a computing device such as a smart phone. The generative system 209 may represent an AI model that is trained to generate content based on prompts to the model. The system 209 may receive a user input requesting a text output from the model, and the model may generate and output text based on the user input. System 209 may be referred to as a question and answer model, where the model is provided a natural language question and the model generates a natural language answer to the question.

In some embodiments, the generative system 209 may allow for multi-shot prompting. A standardized format or output template may be used depending on the content being generated. For example, if system 209 is generating a proposed grocery list, the system 200 may automatically provide particular stored templates for presenting grocery list suggestions. By contrast, a user may request different formats and/or templates when requesting a grocery list. The templates may be predefined or user defined. In some embodiments, the template may mimic output provided in a previous request when the requests are similar in nature. For example, rather than following a predefined template, the generative system 209 may be aware of a prior grocery list request and may provide new output for a different grocery store, but may choose to provide the new output according to the previous output format, alignment, or other similar textual or graphical feature. Providing output in a predictable format provides an advantage to users of expected form and function with a recognizable user interface. Such an advantages enables a user to understand and engage with the output at an accelerated pace than if the format were to differ between queries. Moreover, using a similar or previously known format can improve the ability of the user to determine the reliability and/or accuracy of the output based on the recognition of the way similar data had been previously presented.

In general, the prediction system 210 may function with ML models 104 to preprocess, optionally segment, analyze, and predict blood glucose levels within one or more venous blood vessels. For example, the prediction system 210 may generate one or more outputs such as glucose levels, glucose measurements, glucose predictions, and/or related predictions. In some embodiments, the prediction system may generate the one or more outputs and wearable device 102 may use such outputs to generate indications 250 and/or recommendations 251. For example, prediction system 210 may be used to predict sodium, potassium, glucose, and/or BUN since serum osmolality is based on these metabolites.

Prediction system 210 may use one or more of the following algorithms to predict sodium, potassium, glucose, and/or BUN.

$$(1.86 \times Na) + (glucose/18) + (BUN/2.8) + 9 \qquad \text{Algorithm one}$$

$$(2 \times Na) + (glucose/18) + (BUN/1.8) \qquad \text{Algorithm two}$$

$$(1/86 \times (Na + K)) + (1.15 \times (glucose/18)) + (urea/6) + 14 \quad \text{Algorithm three}$$

In some embodiments, ML models 104 may include a plurality of layers. For example, one or more shallow or lower layers may learn simple features, and one or more deeper layers may learn more complex features. In one exemplary, non-limiting embodiment, a first layer may learn simple features like edges (vertical, horizontal, diagonal) or shades of color. A second layer may learn more complex features such as shapes and textures. A third layer may learn further complex patterns like honeycomb shapes, multi-layered or dimensional shapes, etc. A fourth layer may be able to detect whole objects. A fifth layer may learn features within whole objects or associated with whole objects. Employing exemplary ML models 104 to the embodiments described herein may include using one or more lower layers to detect edges of veins, sizes of veins, shapes of veins, vein or skin color contrast, etc. Further, one or more deeper layers may be used to learn a wrist, background, fingers, whole arm, etc. Since the ML model 104 would be able to learn the shapes of veins, color contrast, and the size of the veins, the ML model 104 may learn to detect changes in the size, shape, and/or color of the veins. In other words, the ML model 104 may detect osmolality changes associated with one or more veins. In some embodiments, one or more connected layers may classify the various changes in size, shape, and/or color into probabilities of each glucose range, as described elsewhere herein.

Indications 250 may be provided and/or presented as text, audio data, and/or visual data including, but not limited to: observations, observation periods, glucose statistics, severity levels, raw measurements, predictive events, and predictive levels of glucose, etc. In some embodiments, the data may further include treatment options, diagnoses, activity levels, patterns in glucose over time, and/or other fitness or health measurements. For example, data may include reports with detailed analyses of glucose level predictions as well as various treatment options for a specific user. In some embodiments, alerts, messages, and/or reminders about particular glucose testing (e.g., image capture) and glucose assessments (e.g., data and/or reports that are generated on a schedule) may notify the user with a visual or audial cue.

Recommendations 251 may be provided and/or presented as text, audio data, and/or visual data including, but not limited to: observations, observation periods, behavior changes, behavior patterns, purchase recommendations, glucose statistics, severity levels, raw measurements, predictive events, and predictive levels of glucose, etc. In some embodiments, the data may further include treatment options, diagnoses, activity levels, patterns in glucose over time, and/or other fitness or health measurements. For example, data may include reports with detailed analyses of behavior (e.g., eating and/or exercise events or patterns), glucose level predictions as well as various treatment or behavior recommendation options for a specific user. In some embodiments, alerts, messages, and/or reminders about particular user behavior may notify the user with a visual or audial cue via device 102, band 1500, band 1550, or the like.

The prediction system 210 may be part of ML models 104 and may utilize ML models 104 and/or image analyzer 212 to generate predictions of glucose levels over time based on captured images and/or reflections from a body site of a user wearing device 102, for example. In some embodiments, the prediction system 210 may determine or predict blood glucose measurements/estimates of a user wearing device 102 by using dynamic image attributes of a body site of the user from one or more sensors 228 on device 102.

In some embodiments, the prediction system 210 represents a diabetes classification system that may predict a likelihood of a user having and/or developing prediabetes, T2D, or another blood sugar disorder based on classifying glucose levels identified by ML models 104 by assessing a historical selection of images of venous blood vessels of a subject (e.g., user) wearing device 102, for example. In some embodiments, the prediction system 210 may further provide predictions for the user with respect to health decline or health improvement based on glucose levels that are determined over time for a particular user.

Predictions may be provided and/or presented as a report including data such as observations, observation periods, glucose statistics, severity levels, raw measurements, etc. In some embodiments, report data may further include treatment options, diagnoses, activity levels, patterns in glucose over time, and/or other fitness or health measurements. For example, reports may include detailed analysis of predictions as well as various treatment options for a specific user. In some embodiments, alerts, messages, and/or reminders about particular glucose testing (e.g., image capture) and glucose assessments (e.g., reports that are generated on a schedule) may notify the user with a visual or audial cue. For example, a visual cue may refer to a message indicator (e.g., indication(s) 250) in an app 204 or an email in an email app. An audio cue may be provided as an audio output from a speaker of device 102, an audio output from a digital assistant in communication with device 102, and/or an audio output from other computing device in communication with device 102.

In some embodiments, the ML models 104 may map the detected changes in the blood to particular glucose levels. The device 102 may obtain additional glucose signals over time by monitoring the body site. Data may be generated from the monitoring and the ML models 104 may map changes over time. In some embodiments, the mapping logic 208 may be used in combination with ML models 104 to map the detected changes in blood to particular glucose levels. For example, one or more images may be obtained from sensor 228. The one or more images may visually show a correlation between a change in a glucose level associated with one or more veins (captured in the one or more images) and a change in an appearance (e.g., a darkness, a size, and a volume) of the one or more veins. The visual changes in the vein can be mapped by ML models 104 using mapping logic 208 to map the visual features/changes to known glucose values.

The mapping logic 208 may represent a set of rules for mapping visual features/changes of a particular image of venous blood vessels to predefined glucose values. For example, the mapping logic 208 may include one or more data structures that correlate blood glucose levels with physical and/or physiological features of a venous blood vessel. The one or more data structures may include one or more lookup tables, algorithms, or techniques. The mapping logic 208 may be applied to function on pixels, voxels, circles, ovals, rectangles, squares, and/or other polygon or predefined shape.

In an example, non-limiting embodiment, mapping logic 208 may include using an edge detector algorithm to detect the edges of one or more blood vessel portions in one or more images; segmenting image portions of the one or more blood vessel portions based on the detected edges; aligning the segmented image portions over time or from two or more time periods; determining a blood volume change between a first image, at a first time, showing the one or more blood vessel portions and a second image, at a second time, showing the one or more blood vessel portions; detecting, using a contrast detector, a change in the darkness or intensities of the pixels between a first image, at a first time, showing the one or more blood vessel portions and a second image, at a second time, showing the one or more blood vessel portions; and mapping the change in darkness or intensities to a corresponding change in a glucose level done based on the determined changed in blood volume and the determined change in darkness or intensities of the pixels. In some embodiments, the first time and the second time are after a predefined event, event-based, on-demand, otherwise. The events may include, but are not limited to, one or more of: a meal, a fast, a physical stressor, exercise, an emotional stressor, a sleep event (e.g., excess sleep, sleep deprivation, exhaustion, etc.), a time of day, and a change in estrogen.

These changes in an appearance (e.g., darkness, size, and volume) of the one or more veins, as captured by the sensor 228, can be ascertained by the device 102 and ML models 104 based on a combined effect of the reduced scattering coefficient of NIR light in the presence of glucose molecules and the change in plasma osmolality as described in detail herein. Determining changes in the appearance of one or more veins of a user wearing device 102, for example, can be used as a way to measure venous blood glucose values for the user in a noninvasive way by using image capture and machine learning image assessments.

In some embodiments, the ML models 104 may utilize mapping logic 208 to map detected changes in the appearance of veins before and after events. The events may include, but are not limited to one or more of: a meal, a fast, a physical stressor, exercise, an emotional stressor, a sleep event (e.g., excess sleep, sleep deprivation, exhaustion, etc.), a time of day, and a change in estrogen. In some embodiments, using ML models 104 to map detected changes in the appearance of veins before and after events allows the learned patterns and predictions (generated by ML models 104) about glucose determinations and/or related predictions to be incorporated into a semi-supervised ML learning stage of ML models 104. For example, a semi-supervised stage of an ML model may include learning from both unlabeled and labeled samples, typically sampled from the same or similar distributions. In some embodiments, using ML models 104 to map detected changes in the appearance of veins before and after events allows the learned patterns and predictions (generated by ML models 104) about glucose determinations and/or related predictions to be incorporated into a self-supervised ML learning stage of ML models 104.

In some embodiments, one or more of ML models 104 may employ self-supervised learning. Self-supervised learning uses surrogate (pretext) tasks that can be formulated using unsupervised data. A pretext task is designed in a way that solving the pretext task includes learning of a useful image representation. In some of the embodiments described herein, the pretext task may be learning representations by maximizing agreement between different views of the veins of each user obtained at the same instant of time. For example, the process may include supervised pretraining using large scale non-medical labeled data (e.g., ImageNet). The process may further include multi-instance contrastive self-supervised pretraining using domain specific unlabeled data, resulting in learning a representation or pretext task. For example, an unlabeled dataset may be collected from any of the devices described herein without a clinical study because the data is unlabeled (i.e., does not include corresponding venous blood glucose values). The process may further include supervised fine-tuning using labeled dataset collected from, for example, a clinical study. This may be the classification step that learns to output glucose range, glucose number, a change in glucose, a glucose color, or the like.

Patient data 206 may include, but is not limited to, patient identifying information (e.g., a name, birthdate, etc.), patient-entered data, and digital data indicative of historical and/or current conditions of a patient, diagnostic tests, and test results associated with the patient, medications prescribed or administered to the patient, therapies (e.g., surgeries, outpatient procedures, or the like) administered to the patient, prior and real time glucose predictions and measurements captured by wearable device 102, data stored or extracted from an electronic medical record (EMR), demographics of a patient, vital signs of a patient, notes from one or more medical appointments attended by the patient, or any combination thereof. In general, patient data 206 may be used by the systems and processes described herein when permission for using such data has been provided by the patient.

One or more processors 218 may be included in device 102. The processors 218 may be used for executing program instructions associated with apps 204, ML models 104, image analyzer 212, and/or mapping logic 208. In some embodiments, the processors 218 may include graphical processing units (GPUs) for rendering and generating graphics, images, video, audio, and/or multimedia files.

Other circuitry such as an analog-to-digital converter (ADC) 220 and a digital-to-analog converter (DAC) 222 can also be located within wearable device 102, such as co-integrated as a portion of a commonly-shared integrated circuit or integrated circuit package. The ADC 220 may convert an analog signal representation of a captured image into a digital representation of the image. The DAC 222 may convert a digital signal representation of a captured image into an analog signal for further processing.

Although the prediction system 210, image analyzer 212, mapping logic 208, and the ML models 104 are depicted as part of the wearable device 102, any or all of such functionality carried out by the prediction system 210, image analyzer 212, mapping logic 208, and/or the ML models 104 may alternatively, or additionally, be carried out by an external computing device, such as the computing device 106 in wired or wireless communication with wearable device 102. In addition, while the image analyzer 212 is depicted external to (e.g., not integrated into) ML models 104, in some embodiments, the image analyzer 212 may be integrated into the ML models 104. In addition, while the prediction system 210 is depicted internal to (e.g., integrated into) ML models 104, in some embodiments, the prediction system 210 may be external to (e.g., not integrated into) the ML models 104.

The wearable device 102 also includes or is communicatively coupled to power 240, input devices 242, and output devices 244. The power 240 may be a power source for the wearable device 102 and/or sensors 228. The power 240 may include or connect to a battery or a port for connecting the wearable device 102 to a power supply, a wall power adapter, a battery pack, or the like.

The input devices 242 may interact with memory 202, one or more processors 218, sensors 228, apps 204, image analyzer 212, prediction system 210, ML models 104, mapping logic 208, and/or patient data 206. The input devices 242 may include touchscreens, switches, buttons, toggles, and/or other hardware components located on wearable device 102. In some embodiments, the input device 242 may be external to or not integrated into the device 102, such that one or more controllers, mobile device, apps (e.g., apps 204), etc., may communicate (e.g., one or more optional antennas 224, coils, etc.) with device 102 using a wireless communications protocol. In some embodiments, the input device 242 may include, for example, a touch input device that can receive tactile user input, a microphone that can receive audible input, and the like.

The output devices 244 may interact with memory 202, one or more processors 218, sensors 228, apps 204, image analyzer 212, prediction system 210, ML models 104, mapping logic 208, and/or patient data 206. The output devices 244 may include, for example, a display (e.g., optional display 226) for visual output, a speaker for audio output, and/or haptic feedback.

In some embodiments, the wearable device 102 is a noninvasive blood glucose monitoring system that is configured to be removably coupled to a body site of a user. The wearable device 102 may include at least one optical sensor (e.g., image sensor 228) communicatively coupled to at least one light source (e.g., red-light source, near infrared light source, optional light source 232 or a light source internal to sensor 228). The optical sensor 228 may sense reflected light from the body site resulting in a captured image. The wearable device 102 may also include and be communicatively coupled to at least one processor (e.g., processor 218) which may be programmed with the techniques and algorithms described herein to programmatically analyze the captured image to determine a blood glucose estimate for the user.

In some embodiments, system 200 may function to nudge users toward improved health behaviors, particularly in individuals exhibiting prediabetes or risk factors for developing type 2 diabetes. The system 200 may include one or more generative AI modules, such as large language models (LLMs, generative systems 209, 209*b*), one or more predictive models (e.g., predictive systems 210, 210*b*) that may function to provide personalized dietary, physical activity, and behavioral guidance based on user-specific health status and preferences.

The nudges described herein may represent indications 220 that may represent recommendations 251 or other prompts to enable a user of wearable device 102 to improve health metrics or lifestyle metrics. Example nudges may include dietary behavior modifications, nutrient modifications, behavioral modifications, exercise modifications, stress modifications, and/or sleep modifications.

In a non-limiting example, the system 200 may identify a user with prediabetes or diabetes risk factors and generate a personalized behavioral intervention plan. The system 200 may recommend a targeted weight reduction of approximately 7% of total body weight through improved diet quality and increased physical activity, for example.

The system 200 may generate recommendations 251 for dietary behavior modifications. For example, the system 200 may identify high added sugar consumption as a modifiable risk factor. One or more ML models 104 may generate tailored recommendations that prompt the user to eliminate sugar-sweetened beverages (e.g., soda, candy, fruit drinks, etc.), informing the user with additional education. For example, the ML models 104 may further indicate to the user that such items constitute empty calories with minimal nutritional value. The system 200 may further query the user to identify frequently consumed sugary items and generate behavioral nudges that frame these foods as occasional rewards (e.g., consumed once weekly instead of daily).

The system 200 may also assess an intake of refined carbohydrates (e.g., white bread, white rice, pastries, etc.) and recommend substitutions with whole grain options, such as whole wheat, barley, millet, and oats. In some embodiments, the system 200 may provide an explanation regarding the limited nutritional value of enriched flours as compared to whole grains, including the loss of dietary fiber.

In cases where device 102 detects glycemic spikes despite whole grain consumption, the ML model 104 may suggest pairing carbohydrates with proteins (e.g., egg) or healthy fats (e.g., almond butter) to moderate glycemic response. If a user is shopping or indicating a request for a shopping list, the system 200 may be also analyze food labels for added sugars and recommend specific brands that meet nutritional criteria, alleviating the burden of label analysis. For example, the system 200 may receive a user prompt such as, 'Which whole grain breads do not contain added sugar?' and the ML model 104 may return product-specific recommendations with annotated nutritional information. A secondary software agent (e.g., agent 109) may be called by the ML model 104 to extract label data, calculate added sugar or calorie totals, and/or compare these values against thresholds defined by health guidelines (e.g., 24 grams/day for adult women).

The system 200 may generate recommendations 251 for fiber intake enhancement. For example, the system 200 may identify insufficient dietary fiber as a common deficiency and recommend increased intake through fruits, vegetables, and cereal-based sources (e.g., wheat, oats, millet, etc.). In some embodiments, the system 200 may provide educational content along with the recommendations 251. For example, the system 200 may provide indications in a user interface that explain the roles of soluble and insoluble fiber in cholesterol and blood glucose management, respectively, and may further suggest whole foods as the preferred delivery vehicle. The system 200 may also provide optional guidance on fiber supplementation when applicable.

The system 200 may generate recommendations 251 for alcohol intake monitoring. For example, in some implementations, the system 200 may prompt users to assess personal alcohol consumption frequency and context (e.g., social functions, weekends). The system 200 may suggest behavioral replacements for alcoholic beverages, including sparkling water, kombucha, or non-alcoholic alternatives. The ML model 104 may also dispel outdated health beliefs regarding alcohol (e.g., the heart-health benefits of red wine), citing recent evidence attributing such benefits to the overall dietary pattern rather than alcohol consumption itself.

The system 200 may generate recommendations 251 for temporal eating patterns. For example, to further support glycemic control, the system 200 may guide users to establish a cutoff time for evening eating (e.g., 8 or 9 PM), thereby minimizing late-night glucose spikes. Additional example behavioral guidance may include instructions to consume proteins and vegetables prior to carbohydrates during meals, which can modulate postprandial glucose levels.

The system 200 may generate recommendations 251 for physical activity integration. For example, the system 200 may prompt users to identify preferred forms of physical activity. Both aerobic and strength-based exercises are recommended, as each contributes to increased insulin sensitivity. The ML model 104 may offer suggestions ranging from moderate-intensity activities (e.g., walking, cycling) to vigorous exercise (e.g., running, lap swimming), and remind users that consistency outweighs selecting a specific modality.

The system 200 may generate recommendations 251 for stress detection and management. For example, the system 200 may monitor indicators of user stress and may invoke a set of actions to reduce stress-related glucose elevation. If stress is detected, the system 200 may activate a game-based nudging mechanism and/or a humor-driven nudging mechanism. A game-based nudging mechanism may launch a gamified behavioral experience, such as a digital version of a game in which beneficial food choices (e.g., vegetables) allow users to ascend toward winning the game while poor choices (e.g., candy) result in setbacks (e.g., descending a feature of the game). A humor-driven nudging mechanism may include delivering context-aware humorous content, such as stand-up comedy clips or ML model 104-generated jokes, to elicit laughter and reduce cortisol levels. In some embodiments, selection of the nudging mechanisms may be user specific. For example, a younger user may enjoy digital games and be more engaged with a gamified nudging.

The AI/ML models described herein can be prompted to suggest all of the above and in that order based on training, user behavior detection, user input, and the like. Moreover, the system 200 may provide real-time user monitoring of diet and activities over time and provide such information in a stepped fashion to ensure compliance to steps for improving behavior, to build knowledge slowly, and to provide research-based medical knowledge on an as detected (or as requested) basis.

In a non-limiting example, the system 200 may adapt recommendation generation behavior and recommendations based on various contextual factors. For example, if a user is attending a conference and unable to adhere to typical recommendations, the lifestyle AI coach 108 may inquire about the conference details. The AI coach 108 may utilize a web-searching function to obtain information about the conference end date and may adjust a nudging mode or strategy, accordingly, thereby resuming normal recommendations after the conference concludes.

In some embodiments, a nudging strategy may represent any number of nudging modes. For example, the AI coach 108 (or user of wearable device 102) may select a light mode, a regular mode, or a heavy mode to receive nudges generated based on the selected mode. By way of example, the system 200 may account for travel scenarios, which often disrupt user health goals. During travel periods, the nudges may transition to the light mode, maintaining minimal guidance to ensure users still consume adequate fiber, vegetables, and water without feeling overly restricted. In general, the system 200 may implement different modes of nudging intensity, including light mode, regular mode, and heavy mode. Light mode may be activated during holidays, business, or personal travel, the postpartum period, short-term illnesses or injuries (personal or of loved ones), and user-designated cheat/light days. Conversely, heavy mode may be employed after discontinuation of certain medications like GLP-1 agonists to prevent rapid weight regain, or when users set aggressive goals, such as in preparation for an upcoming doctor visit.

The lifestyle AI coach 108 may provide various types of recommendations tailored to a particular user context. Example recommendations may include tips on meal timing, focusing on earlier eating and monitoring blood glucose during time-restricted eating trials. The AI coach 108 may also offer guidance on food choices and meal sequencing, assessing glucose control in the context of specific diet plans such as ketogenic diets. Example exercise recommendations may cover both type and duration of physical activities. The system 200 may suggest recipe modifications, such as incorporating more legumes or vegetables into pasta dishes, and may provide strategies for managing food cravings. In examples in which users are discontinuing a GLP-1 agonist medication, the AI coach 108 may offer specific advice for managing withdrawal symptoms and maintaining blood sugar control, including suggestions for nutrient-dense foods and monitoring calorie and/or fiber intake.

A tone and approach of the lifestyle AI coach 108 may be dynamically adjusted based on user feedback. For example, the system 200 may implement a quick poll using emojis to gauge a current emotional state of the user, thereby allowing the AI coach 108 to generate a more empathetic or assertive approach accordingly. This emotional input may also influence the selection of nudging modes.

In some embodiments, the lifestyle AI coach 108 may provide location-specific suggestions, such as identifying nearby grocery stores or recommending healthy menu options from local restaurants. The system 200 and/or lifestyle AI coach 108 may account for seasonal or cultural events that may impact eating patterns. For example, if consistent nighttime glucose spikes are detected for a user during Ramadan, the AI coach 108 may adjust recommendations and shift to a light mode of nudging until the end of the fasting period. Similar adaptations may be made for other holidays that follow non-solar calendars, such as Diwali or Hanukkah.

The system 200 may leverage milestones such as birthdays to encourage behavior change, prompting users to resume glucose monitoring if frequency has decreased and/or suggesting the setting of new lifestyle goals. Subsequently, the AI coach 108 may implement quarterly check-ins to remind users of these goals and assess progress.

In some embodiments, the system 200 may implement behavior-based adjustments. For example, if the lifestyle AI coach 108 detects systematic elevations in glucose levels over the course of a month, the system 200 may provide nudges reminding the user of healthful meal components and encourage the reintroduction of routine exercise. This approach helps address the common issue of declining motivation between healthcare provider appointments, using device-generated data to re-motivate users even before clinical testing occurs. The system 200 may also account for the tendency of users to relax effort after a period of successful outcomes. To address this, the nudge mode may be switched to a light mode after a prolonged stretch of success, such as 3-6 months, and then may revert to the previous mode if the AI coach 108 detects a decline in adherence to health goals.

The frequency and intensity of nudges may be adjusted based on a glucose time in range (or the proportion of glucose values within normal limits) for the user. If the time in range is consistently high, the system 200 may reduce monitoring frequency to weekly checks. However, if values begin to fall out of a predefined range (described elsewhere herein) more often, the AI coach 108 may adapt by deploying more frequent reminders on lifestyle changes and daily monitoring until glucose levels improve. In some embodiments, users may select reminders and monitoring schedules, for example, some users may become used to receiving reminders and monitoring and thus may appreciate the consistency.

In some embodiments, the lifestyle AI coach 108 may also provide real-time, meal-specific guidance. For example, if a trend towards increasing blood glucose levels is detected after typical mealtimes, the AI coach 108 may prompt the user to consume protein-containing foods first at the next meal and suggest a particular meal sequence based on the user entering input including upcoming, planned food items.

In some embodiments, the lifestyle AI coach 108 may provide exercise recommendations that are fine-tuned based on glucose data collected after different types of physical activity. The system 200 and/or the lifestyle AI coach 108 may curate personalized exercise programs by analyzing glucose responses to various forms of aerobic and resistance training.

In some embodiments, the wearable device 102 may be made aware of circumstances such as pregnancy. In response, the lifestyle AI coach 108 may adapt guidance and/or recommendations to address specific health concerns like appropriate weight gain. The AI coach 108 may also provide tailored advice for the postpartum period, when users often shift focus away from personal health and towards infant care.

To reduce barriers to healthful eating, the lifestyle AI coach 108 may inquire about which grocery store(s) the user wishes to shop. Using web-searching or maps-searching functions, the AI coach 108 may suggest alternative stores in the neighborhood if a usual choice is suboptimal from a nutritional standpoint. The system 200 may also provide specific food recommendations within a given store, suggest quick and healthy recipes, and provide detailed shopping lists including ingredient quantities and potential store locations. By making healthful eating more convenient and accessible, the system 200 aims to facilitate easier adoption of beneficial dietary habits. Additional examples are described in FIGS. 17A-18B.

In a non-limiting example, the system 200 may address financial constraints that may impede healthy lifestyle choices. For example, the lifestyle AI coach 108 may inquire about user budget constraints. Upon receiving this information, the AI coach 108 may employ a web-searching function to locate nearby grocery stores and browse through healthy food options. The system 200 may then activate a coding agent (e.g., agent model 109) to generate code or call a predefined function to identify favorable pricing on services and/or food items. The agent model 109 may generate an algorithm that aggregates the prices of healthy items and ensures that the total cost remains within the specified budget limit. Based on this analysis, the lifestyle AI coach 108 may present the user with a list of budget-friendly, healthy food options. To further illustrate the financial benefits of home cooking, the app 204 may provide a chat interface to perform a cost comparison between takeout meals and home-cooked alternatives, displaying the potential financial incentives for preparing meals at home.

In some embodiments, the system 200 may account for loss aversion or bias with respect to understanding that some users may wish to work harder to avoid losses rather than work the same amount to achieve equivalent gains. For example, the system 200 may enable a user to avoid future losses. In a non-limiting example, the system 200 may determine to provide a takeout meal versus home cooked meal price comparison and financial incentive to encourage selection of the home cooked meal. For example, the system 200 may specifically calculate an amount of money to be saved by allowing the system 200 to suggest and perform grocery shopping for a home cooked meal. In some embodiments, the system 200 may further provide a recipe to encourage the user to choose a home cooked meal.

In some embodiments, the system 200 may account for loss aversion bias of a user. For example, the system 200 may calculate and depict progress for accomplishing behavioral goals to encourage continued goal increasing behavior. For example, the system 200 may set goals for the user such as perform moderate physical activity 3 times per week and/or limit added sugars for 5 days in a row. The system 200 may monitor user behavior to assess for the set goals and may project changes in endurance or sugar levels or other health value when detecting a goal failure or backward slide from a set goal. Such goals may be overlaid with other rules, goals, and interruptions. For example, a holiday or planned exercise hiatus can be accounted for with the set goal because the system 200 may extend the days or per week goal to exclude the planned downtime.

The system 200 may also address time constraints, which are often cited by users as a barrier to adopting healthier lifestyles. For example, the lifestyle AI coach 108 may assist users in efficiently restocking food items at home, potentially saving time typically spent on grocery shopping and meal planning. This feature may be beneficial for users following specific dietary guidelines, such as those recommended by diabetes prevention programs, which can be time-intensive to implement.

To combat a lack of immediate symptoms often associated with elevated glucose levels, the lifestyle AI coach 108 may be programmed to educate users about the long-term implications and potential consequences of developing diabetes. The system 200 may employ strategies to counteract optimism bias, which is the tendency to underestimate the likelihood of negative events and overestimate the likelihood of positive ones. The lifestyle AI coach 108 may also provide immediate feedback on glucose levels, interpreting data and presenting typical rhythms of blood glucose changes without having the user read and interpret complex charts. This real-time feedback may serve as motivation for making healthier choices in subsequent meals or during the next grocery shopping trip.

In some embodiments, the system 200 may incorporate gamification techniques to leverage present bias, which is the tendency to assign greater value to immediate rewards compared to future benefits. For example, the AI coach 108 may implement a reward system for achieving exercise goals or improving eating habits, providing immediate positive reinforcement for healthy behaviors. In some embodiments, the rewards may include any suitable goal for a user, such as foods they do not normally consume, a gift or coupon for a product they planned to purchase, a digital reward (e.g., customization items for a user avatar, achievement badges, unlocked content, in-game currency, etc.), etc.

In some embodiments, the lifestyle AI coach 108 may assess baseline patterns of glycemia, including the frequency and timing of glucose checks and the resulting glucose levels. For example, if a user consistently checks fasting blood sugar levels, which are generally within normal range, the AI coach 108 may prompt the user to also check glucose levels 1-2 hours after meals. This additional data may reveal postprandial glucose spikes, which could indicate impaired glucose tolerance and potential prediabetes presentation. Upon detecting such patterns, the lifestyle AI coach 108 may suggest specific dietary modifications. For example, the AI coach 108 may recommend replacing a pastry and coffee breakfast with steel-cut oatmeal and nuts, or advise moving dinner to an earlier time. The system 200 may then track the impact of these changes, potentially observing a reduction in glucose excursions.

In some embodiments, the lifestyle AI coach 108 may be programmed to address common challenges in both short-term and long-term behavior change. For short-term challenges, the AI coach 108 may help users overcome inertia by suggesting small, manageable lifestyle changes and demonstrating their immediate benefits. This approach may prevent users from becoming overwhelmed by attempting to implement multiple significant changes simultaneously. For long-term challenges, the system 200 may be designed to combat issues such as routine fatigue, plateaus in progress, holiday-related setbacks, and/or health challenges. For example, the lifestyle AI coach 108 may provide varied recommendations to maintain engagement, offer strategies for overcoming plateaus, and provide tailored guidance during holidays or periods of health challenges.

The system 200 may also address an importance of social support in maintaining behavior changes. For example, the lifestyle AI coach 108 may inquire about trusted family members or friends (e.g., buddy devices 110) that may provide support and accountability. With user permission, the AI coach 108 may share guidelines and incentives with these trusted individuals, helping to understand how to provide support to benefit the user. Additionally, the system 200 may use web-searching functions to identify activities or locations of interest to both the user and their support network, potentially aligning healthy choices with social activities. In some embodiments, the lifestyle AI coach 108 may directly contact the user's support network to let them know of the user's status and/or to provide scheduled check-ins to further incentivize the user to keep engaged and on track with guidance provided.

In some embodiments, the lifestyle AI coach 108 may incorporate elements of cognitive behavioral therapy, focusing on self-worth and positive self-perception. This approach may help users avoid viewing themselves as impaired or diseased, which could lead to self-fulfilling negative expectations. Instead, the AI coach 108 may emphasize positive reinforcement, particularly when data shows immediate improvements in health metrics.

In some embodiments, the system 200 may address specific hurdles that users commonly face when attempting to adopt evidence-based dietary guidelines. These may include rigid work and home schedules, family resistance to food changes, taste adaptation challenges, and social expectations around food habits. The lifestyle AI coach 108 may provide targeted strategies for each of these challenges, such as suggesting gradual reductions in salt and sugar intake to allow for taste adaptation, or offering ideas for maintaining healthy choices within existing social routines.

The lifestyle AI coach 108 may be programmed to maintain motivation even after users achieve initial health goals or start medication regimens. By providing updated recommendations and/or nudges, the system 200 may continue emphasizing the ongoing benefits of healthy behaviors and the potential to prevent future complications. In this way, the AI coach 108 may help users avoid the common pitfall of relaxing healthy habits after reaching a perceived endpoint.

In some embodiments, the system 200 may provide continued support during periods of high stress, vacations, holidays, or illness, when users are more likely to deviate from healthy behaviors. For example, the lifestyle AI coach

108 may offer modified recommendations during these periods, helping users maintain some degree of healthy habits without adding undue stress.

Through the varied and adaptive approaches described herein, the system 200 may provide comprehensive, personalized support for users seeking to improve health behaviors and management of glucose levels effectively. Additional examples are described in FIGS. 17A-18B.

Figure 3:
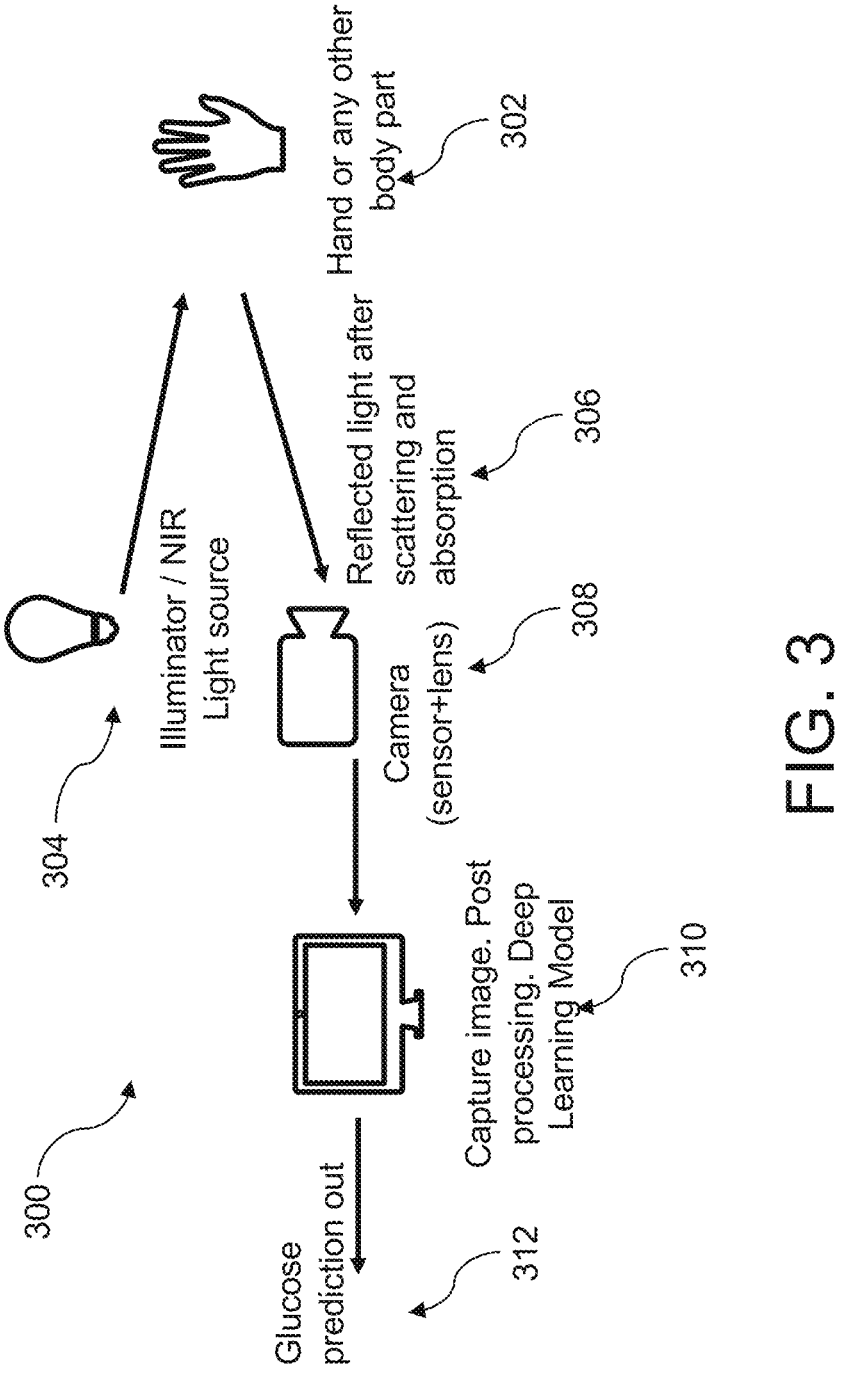
FIG. 3 illustrates a block diagram of an example end to end system for generating noninvasive glucose assessments associated with a body site of a user.

FIG. 3 illustrates a block diagram of an example end to end system 300 for generating noninvasive glucose assessments associated with a body site of a user. The system 300 may include the wearable device 102 (FIG. 2) placed substantially adjacent to a body site of the user, such as a volar wrist. In operation, the system 300 may illuminate (304) a body site 302 (e.g., a hand or other body part) having one or more visible venous blood vessels. The illuminating may cause (306) reflected light to scatter and absorb at the body site 302. The scattered light may be captured (308) by an image sensor 308 (e.g., image sensor 228, camera, optical sensor, etc.). The captured image may be processed (310) by one or more deep learning models (e.g., ML models 104) to generate (312) a glucose level prediction for the user associated with the body site 302.

In general, the system 300 may capture images of veins at the body site. During illumination of the body site, changes in glucose can be monitored and compared over time using system 300, as described in detail in FIG. 2. Changes in the concentration of glucose may modify the indexes of refraction of both the intracellular medium and the extracellular medium, which in turn alters the scattering properties of those media. Such changes in scattering and photon absorption in clinical measurements, as described in detail in Table 1 below, suggest a strong correlation between a reduced scattering coefficient and the concentration of glucose as determined from a blood test. As will be described in detail herein, the image recorded by an NIR image sensor 308 depicts a correlation between glucose level (as read by over-the-counter (OTC) glucose meter) and the darkness/appearance of veins and the surrounding area. The system executing on device 102 and/or system 300 may be used to detect particular glucose measurements and/or determine glucose-based or health based predictions about a user wearing device 102 based at least in part on this correlation. Thus, upon capturing one or more images of a body site, the one or more images may be stored and programmatically analyzed (i.e., using a computer system using hardware and software) to obtain a predicted output value of glucose for the user. The systems 200, 300 may learn to recognize any change in the absorption and/or scattering of NIR light within a vein to ascertain an estimated change in a glucose level in the blood of the user.

Figure 4A:
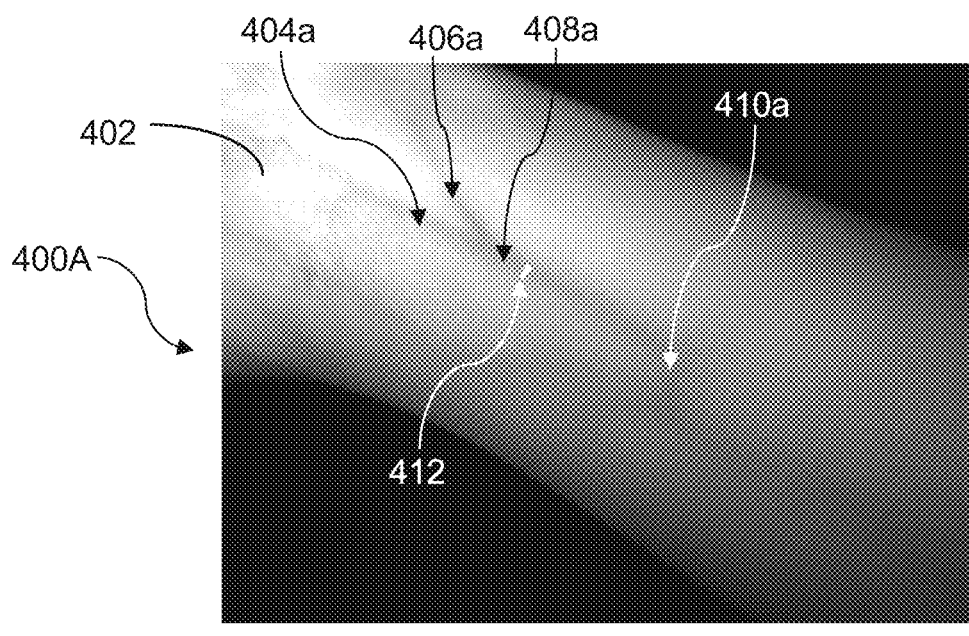
FIGS. 4A-4B illustrate photographic images depicting IR light reflecting off of a volar wrist of a user.
Figure 4B:
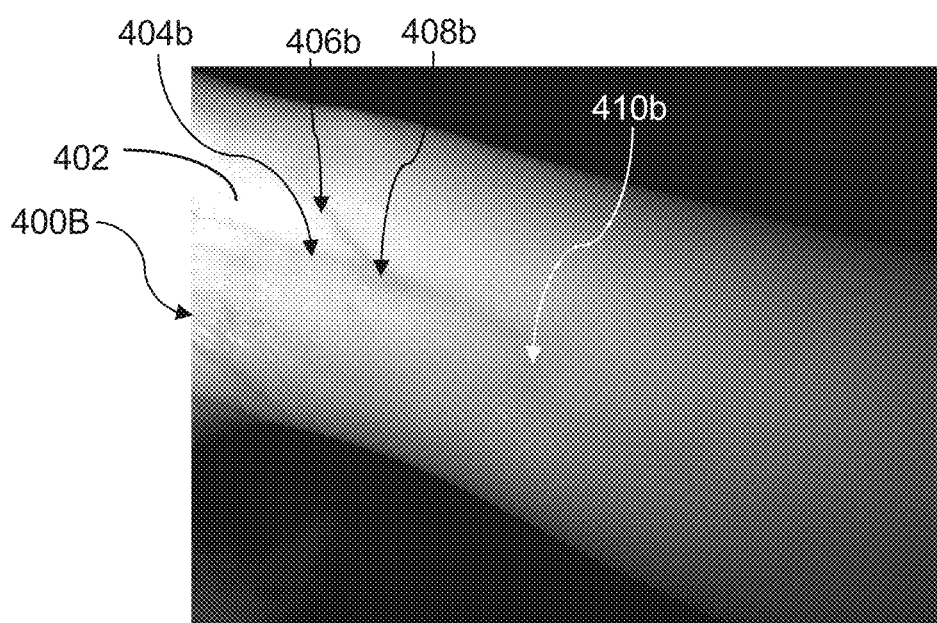

FIGS. 4A-4B illustrate photographic images 400A, 400B depicting IR light reflecting off of an arm (e.g., volar wrist 402) of a user. In this example, the volar wrist 402 may represent a body site on which device 102 may be worn. Alternatively, the volar wrist 402 may represent a body site that is placed into contact with an image sensor (e.g., image sensor 228), detector, or other element of device 102 worn on another body part in order to generate a glucose prediction/measurement for the user. While the images shown in FIGS. 4A-4B may depict a swatch of the body site that is larger than what may be captured and/or analyzed by device 102, the images represent at least portions of the arm that could be captured and analyzed by the device 102. The systems and methods described herein may of course, capture and analyze less than an entire image of a particular body part while maintaining the ability to ascertain blood glucose levels associated with less than the entire body site, and/or the ability to ascertain other physiological parameters or conditions.

FIG. 4A illustrates a photographic image 400A of a user with a glucose meter reading of about 93 mg/dL. Here, the wearable device 102 may capture at least one digital image 400A representing infrared light reflected from the arm. Here, the arm is a non-limiting example of a body site in an upper extremity of the user such that a sensor (e.g., image sensor 228) installed on the wearable device 102, for example, may capture at least one digital image of the volar wrist of the user when the wearable device 102 is worn on the wrist.

The wearable device 102 (and/or other computing device communicatively coupled to device 102) may programmatically analyze the captured digital image(s) to ascertain that digital data captured by the image sensor 228 corresponds to or is strongly suggestive of particular glucose meter reading values based on the characteristics of the reflected light. For example, the wearable device 102 (and/or other computing device communicatively coupled to device 102) may programmatically analyze the image 400A to assess blood glucose for a user. The analyzing may include segmenting, by a first ML model (e.g., ML model 104a) the image 400A into a plurality of regions. The regions may each include at least a portion of a venous blood vessel (e.g., vessel 404a, vessel 406a, vessel 408a, and/or 410a). The segmenting performed by ML model 104a may be performed to detect at least one venous blood vessel (or at least one portion of the venous blood vessel) in the image 400A, for example.

The analyzing performed by wearable device 102 (and/or other computing device communicatively coupled to device 102) may further include analyzing, by a second ML model (e.g., ML model 104b), a visual appearance of at least one of the identified venous blood vessels in the plurality of regions of the image. Analyzing a visual appearance may include analyzing a pixel intensity (e.g., darkness, brightness, etc.) of each venous blood vessel or portion of such a vessel represented in a given image. Each intensity level determined for a region in an image may be compared to predefined glucose data and/or patient data 206 to determine an accurate glucose level and/or glucose prediction for the user. The ML model 104b may use mapping logic 208 and/or prediction system 210 to determine the accurate glucose level and/or glucose prediction for the user in near real time.

For example, analyzing the visual appearance of one or more venous blood vessels in the plurality of regions includes determining an intensity level of pixels representing a portion of the venous blood vessel(s). For instance, the intensity level of pixels may represent a darkness level or brightness level that may be ascertained by processing the image 400A and determining that pixels representing the vessel portion 404a are at a first intensity level, while vessel portions 406a, 508a, and 410a are at different intensity levels. The intensity levels may be further analyzed in combination and/or with other data to generate a glucose level and/or glucose prediction for the user.

For example, additional analysis of the veins in the image 400A may be performed and combined with other analysis (e.g., determined intensity levels of particular veins, prior glucose predictions or measurements, or the like) and/or patient data 206. In some embodiments, the ML model 104b may also determine a dehydration level and/or an osmolality level based on one or more features of the pixels representing the portion of at least one venous blood vessel (e.g., vessel 404a, vessel 406a, vessel 408a, and/or 410a). Such features may include a blood vessel diameter 412 of the portion of one or more venous blood vessel in the image. For example, the ML model 104b may use the image 400A to determine a vessel diameter of any portion of vessels 404a-410a, for example. The determination of dehydration levels and/or osmolality levels may be compared to population level data, prior images associated with the user wearing device 102, and/or patient data 206 in order to determine changes in vessel diameter, vessel behavior, and/or vessel size, in general.

Another feature that the ML model 104b can determine is a volume of fluid in the portion of the one or more venous blood vessels in the image 400A. For example, the ML model 104b may analyze the fluid, particulates, and/or cross sectional areas and any associated volumes pertaining to the one or more venous blood vessels in the image 400A.

In addition, the second ML model 104b may also perform a classification process to classify the plurality of regions according to predefined glucose levels. For example, each of the veins in the image 400A may be classified into a particular window of glucose measurements based on a visual appearance in an image including any or all of the determined pixel intensity levels, the determined dehydration level approximations, the determined osmolality level approximations, the determined vessel diameters and related size-based parameters, and/or the determined volumes associated with at least a portion of one or more of the venous blood vessels depicted in image 400A, for example.

The wearable device 102 (and/or other computing device communicatively coupled to device 102) may then generate, based on the classifying and on the visual appearance of the at least one venous blood vessel, a blood glucose estimate for the user. That is, the wearable device 102 (and/or other computing device communicatively coupled to device 102) may utilize the pixel intensity levels, dehydration level approximations, osmolality level approximations, vessel diameters and related size-based parameters, and volumes associated with at least a portion of one or more venous blood vessels to generate a predicted glucose level and/or measurement for a user of the one or more venous blood vessels. Additional indications 250 may also be provided to a user using device 102 (and/or other computing device communicatively coupled to device 102) based on the generated predicated glucose level and/or measurement.

FIG. 4B illustrates a photographic image 400B of the same user of FIG. 4A with a glucose meter reading of about 89 mg/dL. The image 400B was captured after the user of FIG. 4A ingested a meal. The glucose level has dropped about 5 points from 93 mg/dl to 89 mg/dL. Visual changes are apparent between vessels 404a and 404b, 406a and 406b, 408a and 408b, and between vessels 410a and 410b. Namely, each vessel 404b, 406b, 408b, and 410b of FIG. 4B has less intensity, less volume, and less size than that of the veins 404a, 406a, 408a, and 410a of FIG. 4A.

The wearable device 102 (and/or other computing device communicatively coupled to device 102) may perform the same process as described in FIG. 4A (and/or FIG. 13) to ascertain parameters including, but not limited to the pixel intensity levels, dehydration level approximations, osmolality level approximations, vessel diameters and/or related size-based parameters, or volumes associated with at least a portion of vessels 404b, 406b, 408b, and 410b shown in FIG. 4B. FIG. 4B represents the vessels 404b, 406b, 408b, and 410b at a time after a meal event. The parameters may be used to determine a corresponding glucose level for the user at the time after the meal event. Classification or reclassification of outputs from ML model 104b may also be performed to determine an updated predicted output value (e.g., glucose level) for the user.

Figure 5A:
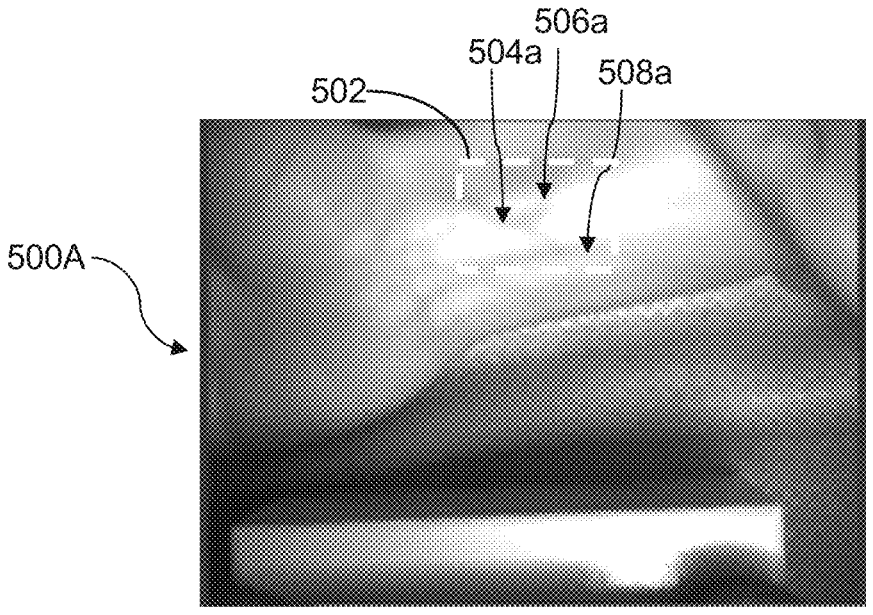
FIGS. 5A-5B illustrate photographic images depicting IR light reflecting off of a volar wrist of a user before and after an event, respectively.
Figure 5B:
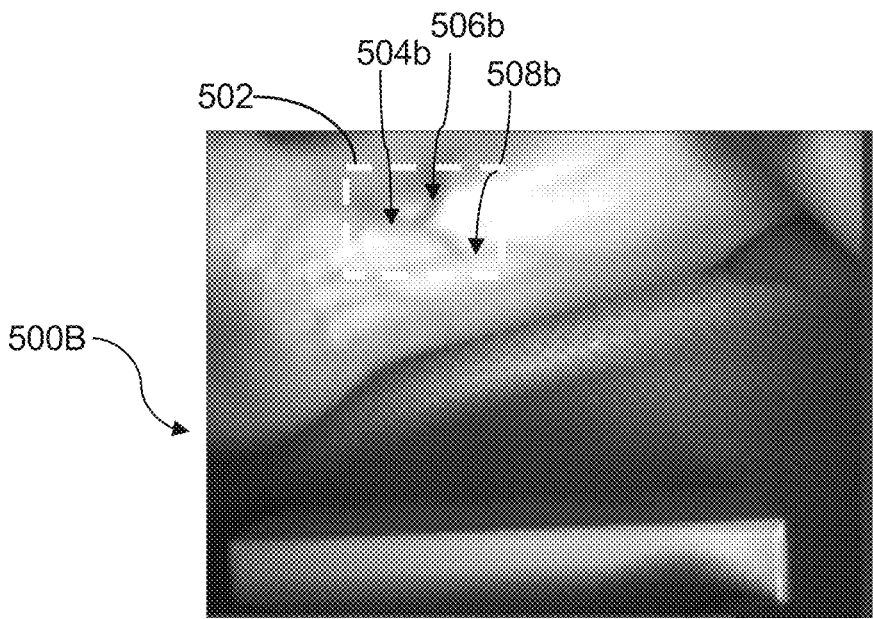

FIGS. 5A-5B illustrate photographic images 500A, 500B depicting IR light reflecting off of an arm (e.g., volar wrist body site 502) of a user before and after an event, respectively. The event described here includes ingestion of a meal, but any event that may alter blood glucose may be substituted and a blood glucose prediction/measurement can be made by wearable device 102 and/or other computing system described herein. Table 1 below indicates the event/meal and the changes in glucose levels, as measured by a glucose meter.

In this example, the body site 502 may represent a body site on which wearable device 102 may be worn. Alternatively, the body site 502 may represent a body site that is placed into contact with an image sensor (e.g., image sensor 228), detector, or other element of device 102 worn on another body part in order to generate a glucose prediction/measurement for the user. While the images shown in FIGS. 5A-5B may depict a swatch of the body site that is larger or smaller than what may be captured and/or analyzed by device 102, the images represent at least portions of the arm that could be captured and analyzed by the device 102. The systems and methods described herein may, of course, capture and analyze less than an entire image of a particular body site while maintaining the ability to ascertain blood glucose levels associated with less than the entire body site, and/or the ability to ascertain other physiological parameters or conditions.

FIG. 5A illustrates a photographic image 500A of a user with a glucose meter reading of about 97 mg/dL. The wearable device 102 (and/or other computing device communicatively coupled to device 102) may analyze the body site 502 to determine and/or predict a blood glucose level for the user wearing device 102 at a particular point in time, as described in detail herein. In this example, the analysis may be based at least in part on visually assessing a venous blood vessel 504a, a venous blood vessel 506a, and/or a venous blood vessel 508a. For example, the wearable device 102 may analyze a visual appearance of one or more vessels to determine a blood glucose level for the user at a point in time. For example, the wearable device 102 may analyze the visual appearance of vessel 504a, 506a, and/or 508a to determine a blood glucose level for the user wearing device 102. Analyzing the visual appearance of vessels 504a, 506a, and/or 508a may include, but is not limited to, assessing pixel intensity, osmolality, blood vessel diameter, blood vessel size, vessel length, vessel width, vessel cross-sectional area, or the like of a portion of one or more venous blood vessels 504a, 506a, and/or 508a in the image 500A.

FIG. 5B illustrates a photographic image 500B of a user with a glucose meter reading of about 92 mg/dL. In this example, the user wearing device 102 ingested a meal and the image 500B depicts a reading directly after ingestion of the meal. The wearable device 102 may assess the visual appearance of body site 502 and in particular, of the same vessels, shown in image 500B as vessels 504b, 506b, and 508b. The vessels 504b, 506b, and 508b are depicted with greater pixel intensity than vessels 504a, 506a, and 508a. In addition, vessels 504b, 506b, and 508b are larger (e.g., wider and longer) than vessels 504a, 506a, and 508a. However, the changes between image 500A and image 500B may not be apparent to the visual eye to provide a blood glucose level or measurement. As such, the wearable device 102 and in general the systems described herein may assess the images to determine and/or predict specific blood glucose levels and/or measurements such that the user may make informed decisions to maintain and/or improve blood sugar health, or the like.

Figure 6A:
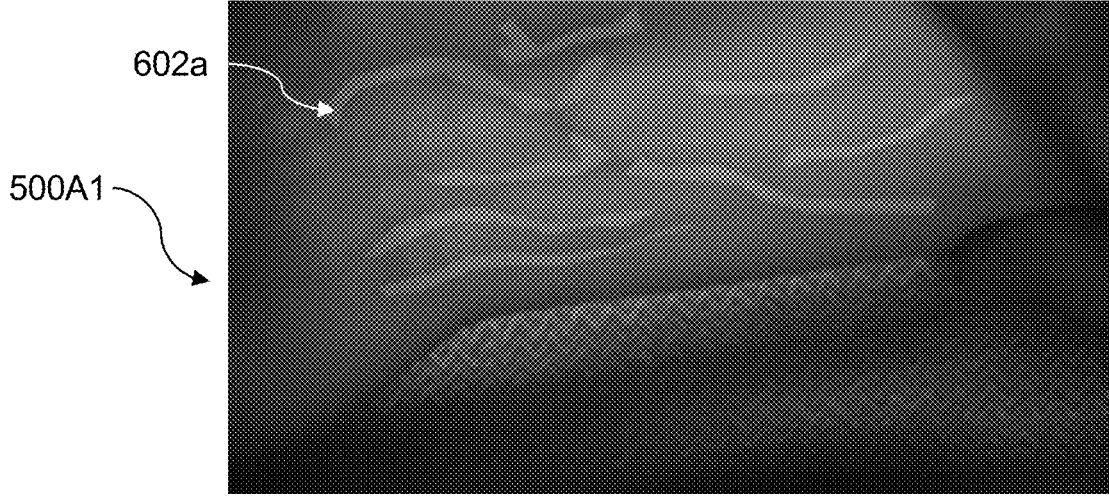
FIGS. 6A-6B illustrate photographic images of a volar wrist with mapped veins before and after an event, respectively.
Figure 6B:
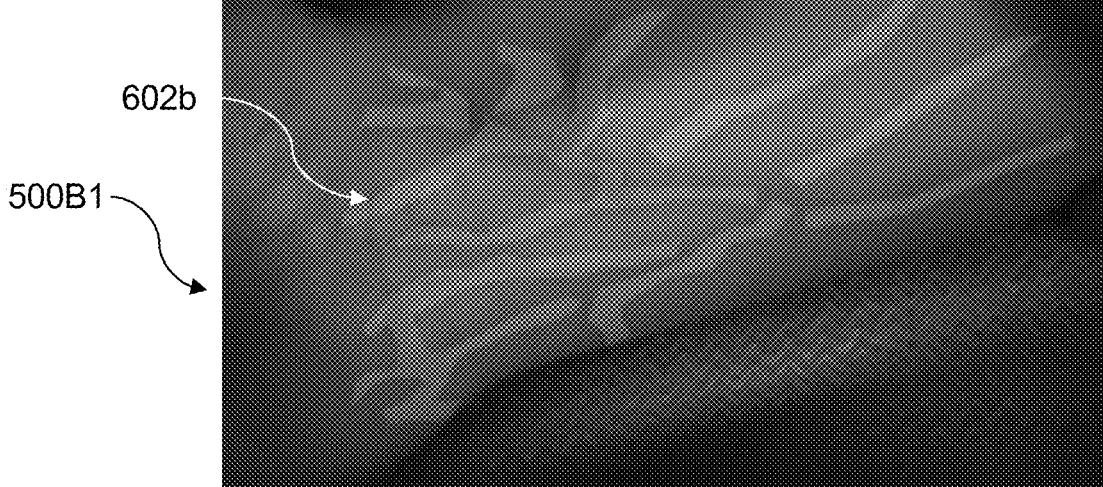

FIGS. 6A-6B illustrate photographic images of a volar wrist with mapped veins before and after an event, respectively. The user depicted in FIGS. 6A and 6B is the same user and timing as shown in FIGS. 5A and 5B, respectively. Here, the wearable device 102 and/or the systems described herein may analyze the visual appearance of venous blood vessels (and/or vessel portions) depicted in the image 500A1 to determine a first glucose measurement and/or prediction. The device 102, for example, may map particular vessels with specific measurements, overlays, and/or coordinates that may be used for future analysis of glucose for the user at a later time. For example, at a later time after an event, such as a meal.

FIG. 6B illustrates the same user of FIG. 6A after a meal event. The wearable device 102 may next analyze the visual appearance of the same venous blood vessels (and/or vessel portions) shown in image 500B1 to generate a second glucose measurement and/or prediction, which may also be marked and/or mapped with measurements, overlays (e.g., overlay 602a, 602b, etc.), and/or coordinates corresponding to changes in the visual appearance of one or more vessels.

In some embodiments, the first glucose measurement can be compared to the second glucose measurement to generate indications for the user, as described in detail herein. For example, the overlay 602a in image 500A1 depicts a vessel as a particular width and length while overlay 602b in image 500B1 differs from the width and length of overlay 602a. The differences can be analyzed by ML models 104 to identify specific changes in the vessel(s) over time to determine occurrences of blood glucose changes and estimates of blood glucose levels. Any number of glucose measurements and/or vessel analysis may be performed to generate additional indications or related data.

Figure 7A:
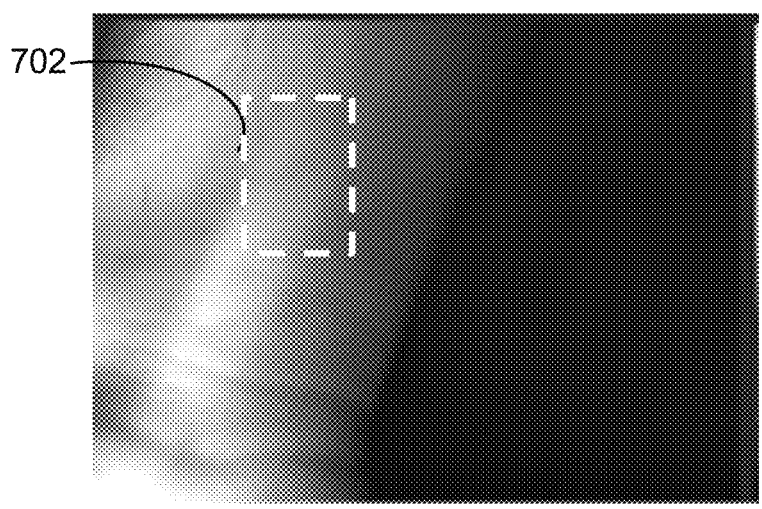
FIGS. 7A-7B illustrate photographic images of a volar wrist captured before and after a meal, respectively.
Figure 7B:
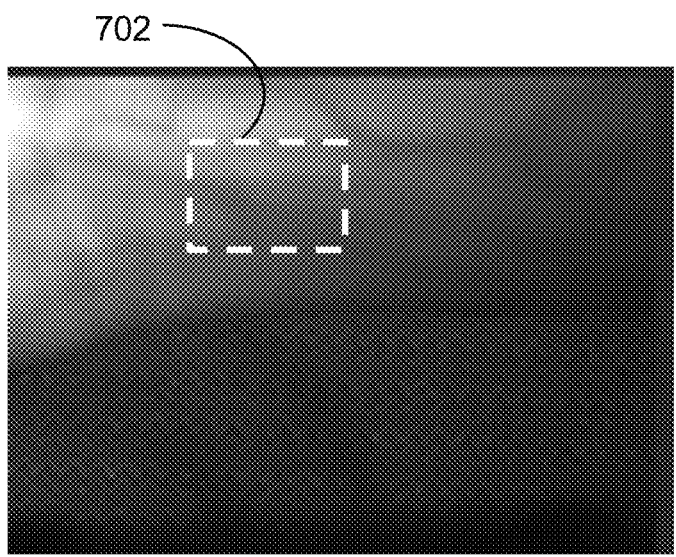

FIGS. 7A-7B illustrate photographic images of a volar wrist body site 702 captured before and after a meal, respectively. FIG. 7A illustrates the body site 702 before a meal while FIG. 7B illustrates the body site after a meal, as indicated in Table 1 below. In this example, the wearable device 102 may again analyze the change in visual appearance of vessels within body site 702 to ascertain changes in glucose over time, as described in detail herein.

Figure 8A:
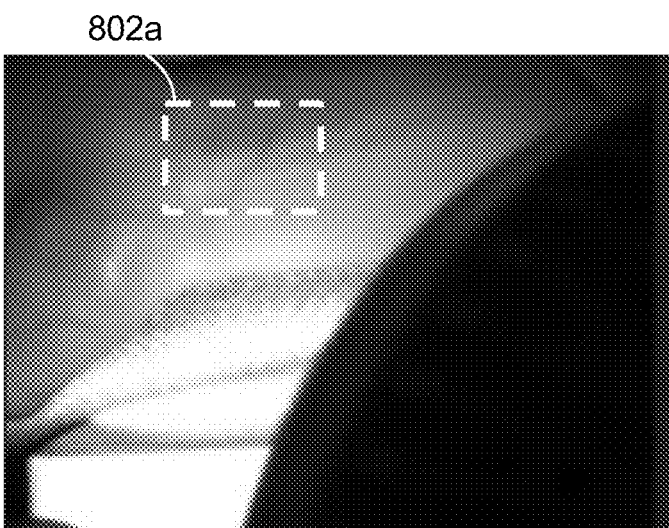
FIGS. 8A-8B illustrate photographic images of a volar wrist captured before and after a meal, respectively.
Figure 8B:
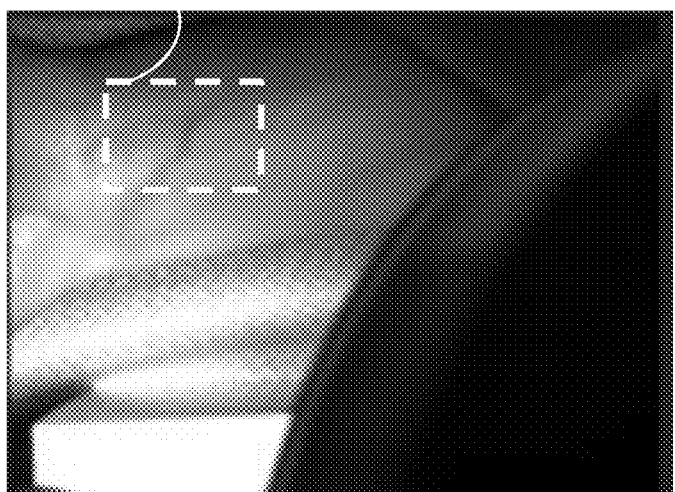

FIGS. 8A-8B illustrate photographic images of a volar wrist body site 802a and body site 802b captured before and after a meal, respectively. FIG. 8A illustrates the body site 802 before a meal while FIG. 8B illustrates the body site after a meal, as indicated in Table 1 below. In this example, the wearable device 102 may again analyze the change in visual appearance of vessels within a first body site 802a to ascertain changes in glucose over time by comparing to the same vessels or different vessels in a second and different body site 802b. For example, if wearable device 102 shifts on the body site 802a to body site 802b, assessments and predictions may still be performed by device 102 by assessing any image overlap and/or assessing additional vessels in the latest image in time (e.g., FIG. 8B).

Figure 9A:
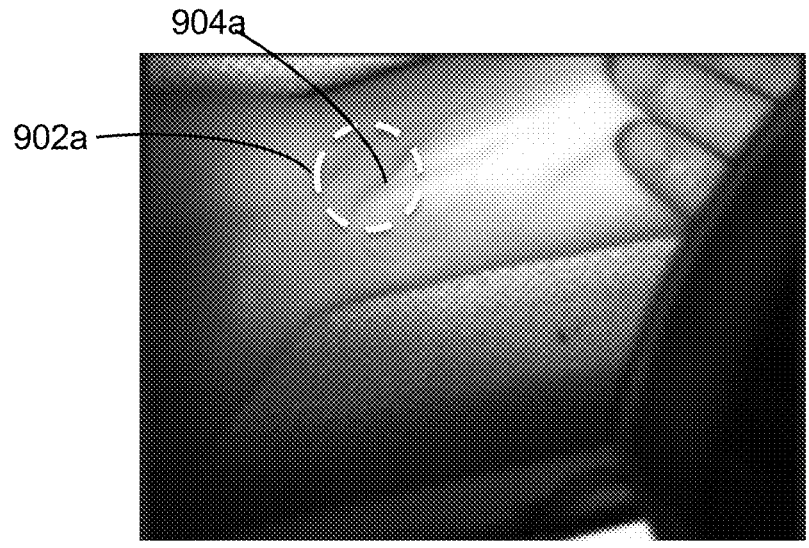
FIGS. 9A-9B illustrate photographic images of a volar wrist captured before and after a meal, respectively.
Figure 9B:
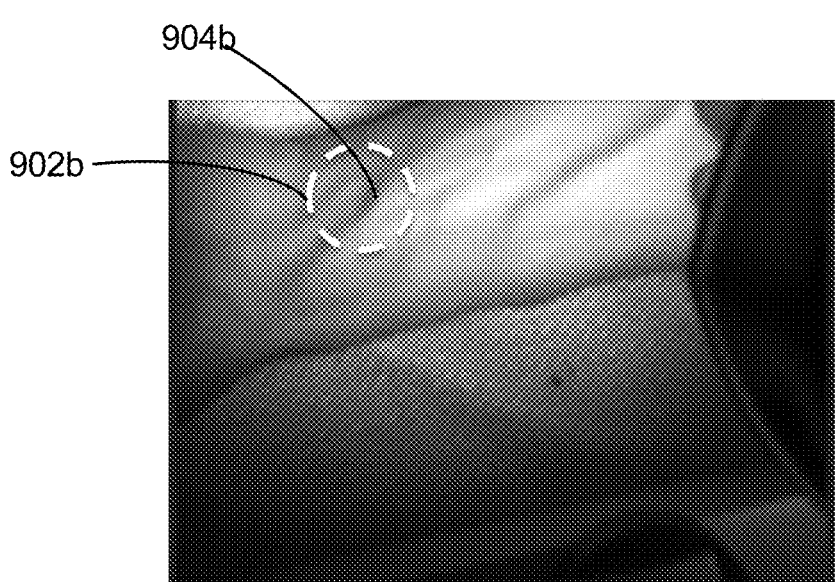

FIGS. 9A-9B illustrate photographic images of a volar wrist captured before and after a meal, respectively. FIG. 9A illustrates the body site 902 before a meal while FIG. 9B illustrates the body site after a meal, as indicated in Table 1 below. In this example, the wearable device 102 may again analyze the change in visual appearance of vessels within body site 902 to ascertain changes in glucose over time, as described in detail herein.

A vessel 904a is shown in both FIGS. 9A and 9B. In FIG. 9B, the vessel 904b is shown to have grown larger than vessel 904a shown in FIG. 9A. In particular, in FIG. 9B, the vessel 904b is shown to be bulging. This change may be detected by wearable device 102 and further analysis can be performed to identify specific changes in blood glucose that occurred between the image captures of FIG. 9A and FIG. 9B. In this example, the body site is shown as a circular shape, however, any shape or size of a capture area on a body may be used by wearable device 102.

Figure 10A:
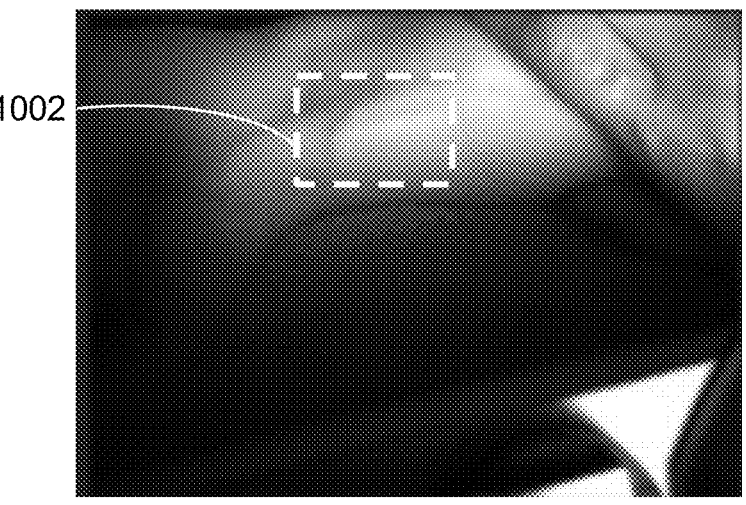
FIGS. 10A-10B illustrate photographic images of a volar wrist captured before and after a meal, respectively.
Figure 10B:
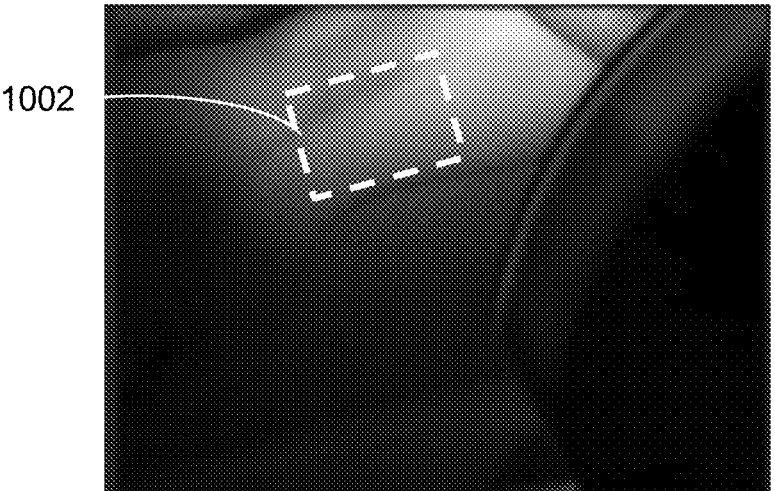

FIGS. 10A-10B illustrate photographic images of a volar wrist body site 1002 captured before and after a meal, respectively. FIG. 10A illustrates the body site 1002 before a meal while FIG. 10B illustrates the body site after a meal, as indicated in Table 1 below. In this example, the wearable device 102 may again analyze the change in visual appearance of vessels within body site 1002 to ascertain changes in glucose over time, as described in detail herein.

Figure 11A:
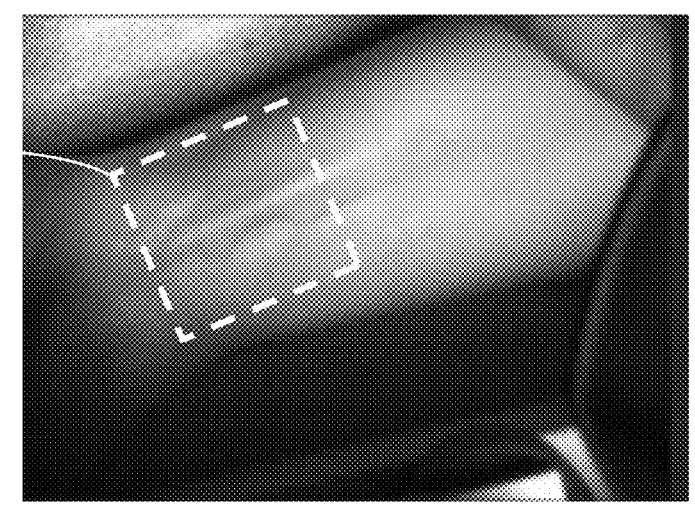
FIGS. 11A-11B illustrate photographic images of a volar wrist captured before and after a meal, respectively.
Figure 11B:
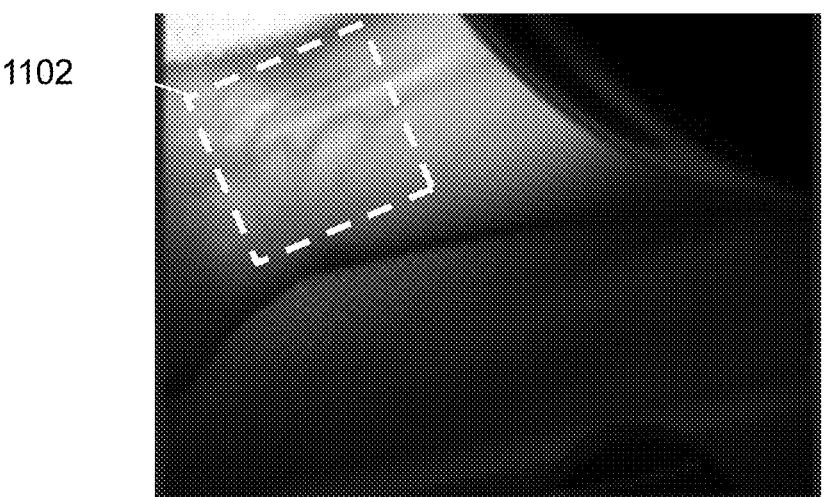

FIGS. 11A-11B illustrate photographic images of a volar wrist captured before and after a meal, respectively. FIG. 11A illustrates the body site 1102 before a meal while FIG. 11B illustrates the body site after a meal, as indicated in Table 1 below. In this example, the wearable device 102 may again analyze the change in visual appearance of vessels within body site 1102 to ascertain changes in glucose over time, as described in detail herein.

FIGS. 12A-12D illustrate example placement of an example noninvasive glucose monitoring device. The noninvasive glucose monitoring devices described herein may take any form or shape that may be fitted to a body site in which one or more venous blood vessels are visible under the skin associated with the body site. The devices of FIGS. 12A-12D may represent wearable device 102. The devices of FIGS. 12A-12D are depicted on or adjacent to a dextral or volar wrist of a user. Although the devices of FIGS. 12A-12D are depicted as a smart watch, other form factors are possible including one or more of a device integrated into a band, a watch, an adhesive strip, jewelry, a patch, clothing, or any other wearable accessory. Various shapes of the devices of FIGS. 12A-12D are depicted. However, other shapes are possible.

Figure 12A:
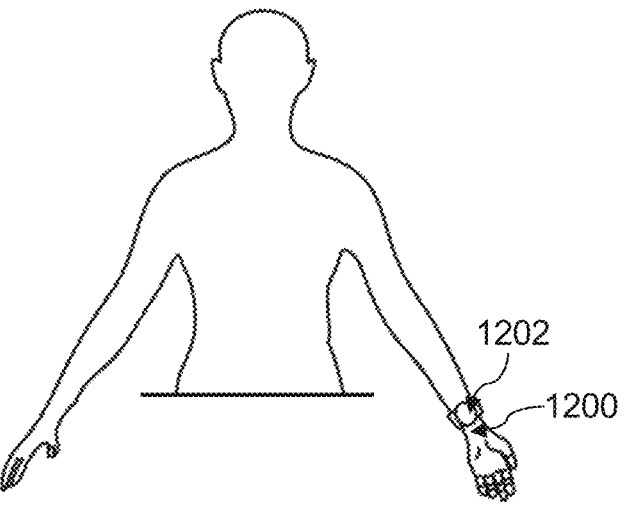
FIGS. 12A-12D illustrate example placement of an example noninvasive glucose monitoring device.

FIG. 12A illustrates an example wearable device 1200 on a volar wrist 1202 of a user. In this example, an image sensor (e.g., image sensor 228) may be coupled to (or integrated into) a base portion (not shown) of device 1200. In operation, the base portion is placed in contact with a portion of the volar wrist. The device 1200 may capture one or more images of the portion of the volar wrist 1202 of the user wearing device 1200.

Figure 12B:
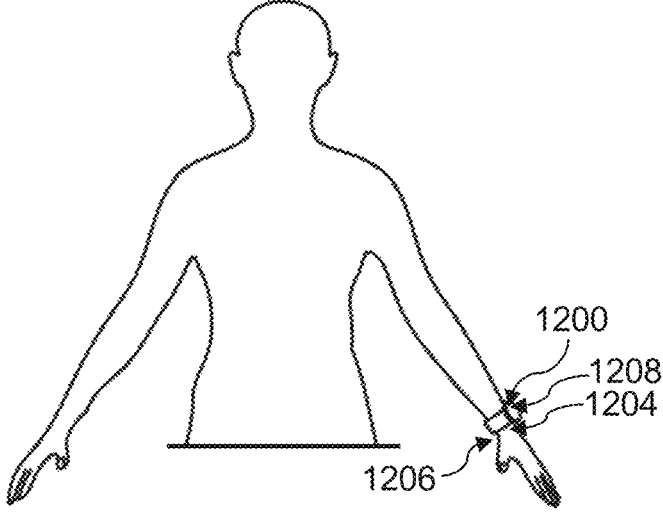
Figure 12C:
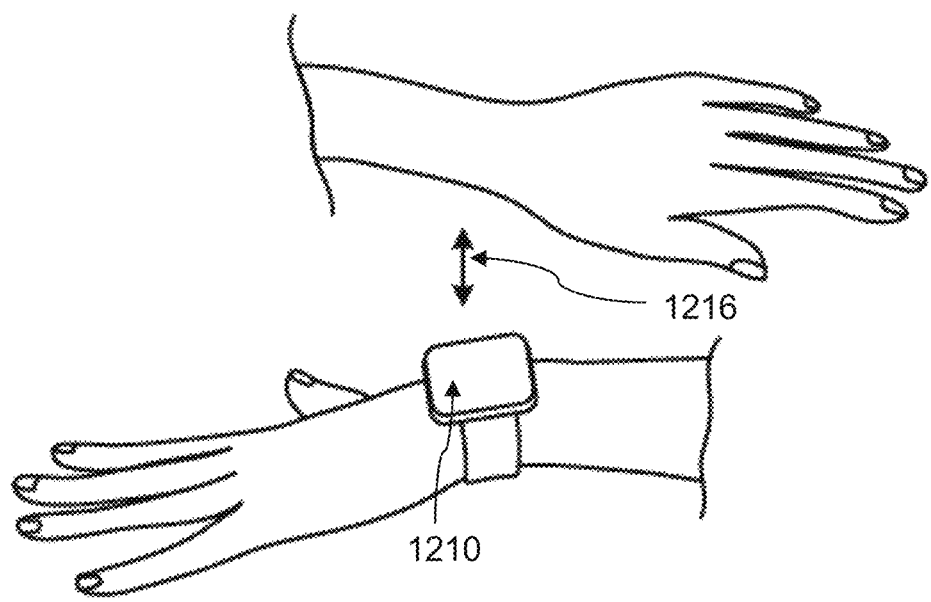
Figure 12D:
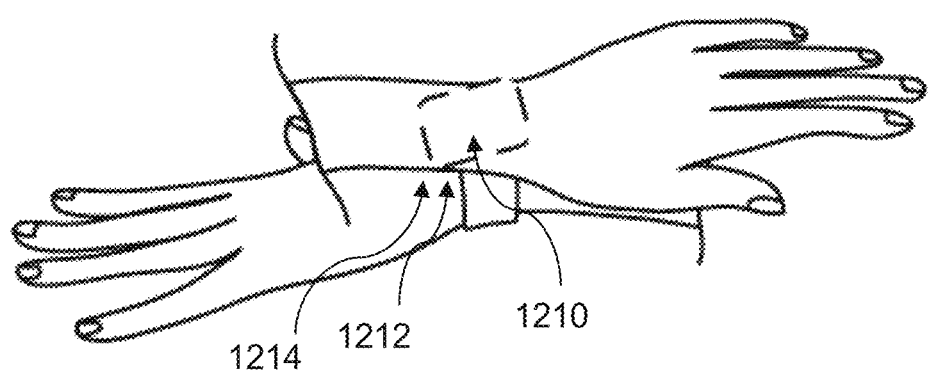

FIG. 12B illustrates the example wearable device 1200 on a dextral wrist 1204 of a user. In this example, an image sensor (e.g., image sensor 228) may be coupled to (or integrated into) a strap portion 1206 of the device 1200 to capture images of a portion of the volar wrist 1202 of the user. In some embodiments, the image sensor may instead be coupled to (or integrated into) a top portion 1208 of device 1200. In such an arrangement, images may be captured of one or more venous blood vessels in response to a user placing a body site in contact or near contact (e.g., hover) with the top portion 1208 and device 1200 detecting such contact or near contact, as shown in FIGS. 12C and 12D. In addition, such an arrangement may also allow for device 1200 to be placed in contact (or near contact) with another body portion including, but not limited to a neck, a lymph node region, or any portion of a limb, an abdominal region, or a thoracic region.

FIG. 12C illustrates an example wearable device 1210 for capturing images of body sites that are not wearing the wearable device. For example, device 1210 may include one or more image sensors (e.g., image sensors 228) on any surface of the device facing away from the skin in contact with the device. Such surfaces may include such sensors and illumination devices to capture images of body sites when the device 1210 detects a nearness or contact with a particular body site. For example, the device 1210 may be worn on a sinistral dorsal wrist 1212 with a sensor and/or light source positioned on the sinistral dorsal wrist 1212 and facing away from the sinistral dorsal wrist 1212. The user may move the dextral volar wrist 1214 toward the face of device 1210, as shown by arrow 1216. When the sensor detects that the dextral volar wrist 1214 is within a predefined range of the light source on device 1210, at least one digital image captures at least a portion of the dextral volar wrist 1214. Although FIGS. 12C-12D show the device 1210 on a sinistral wrist and detection occurring on the dextral wrist, one of skill in the art will appreciate that the device 1210 may be worn on the dextral wrist and the detection may occur on the sinistral wrist.

FIG. 12D illustrates the example wearable device 1210 of FIG. 12C capturing images of a body site that is not wearing the wearable device. In this example, the device 1210 may capture images of a body site that is placed on (or adjacent to) a sensor on device 1210.

Figure 13:
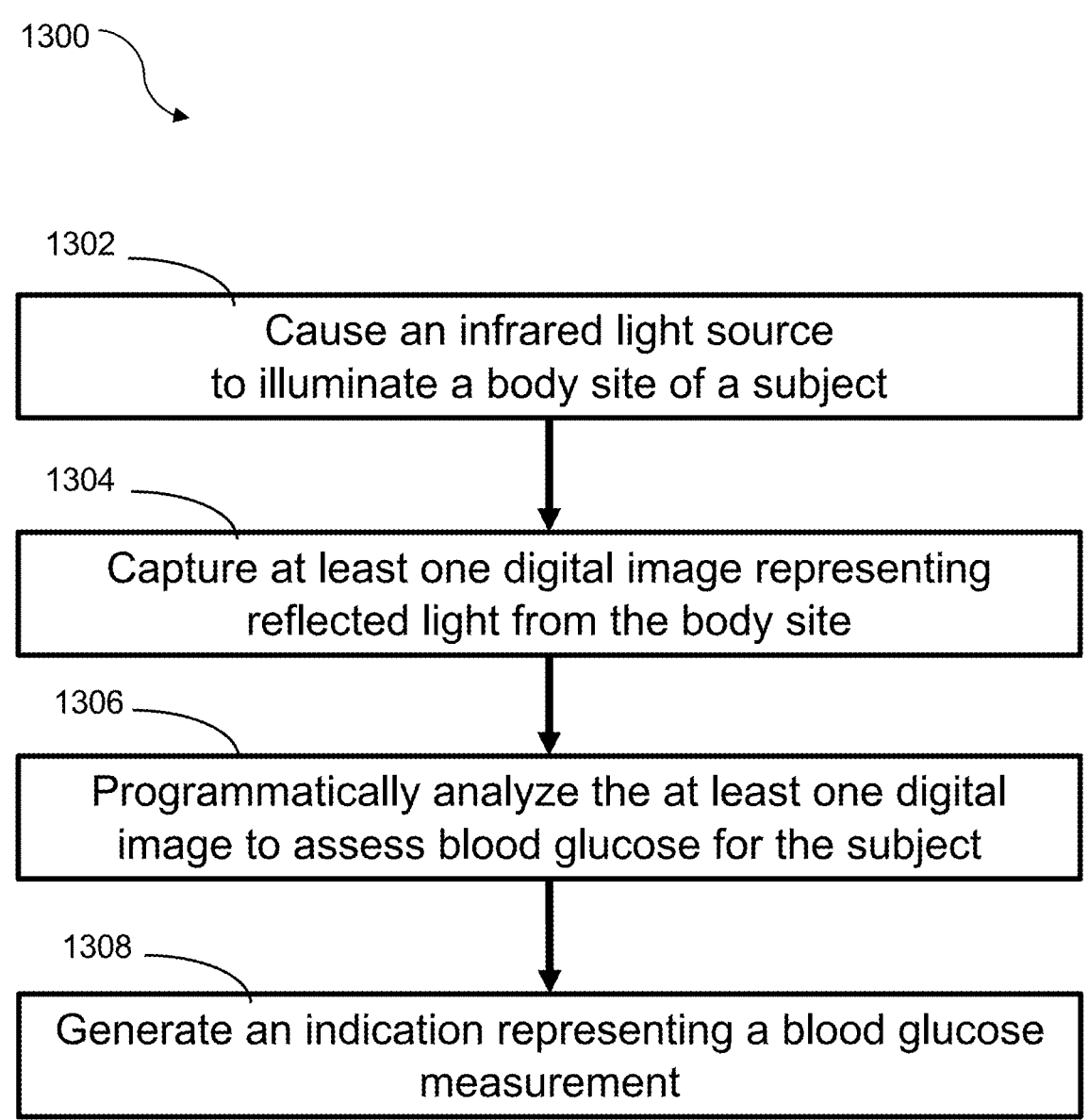
FIG. 13 illustrates a flow diagram of an example process for performing noninvasive blood glucose monitoring of a user.

FIG. 13 is a flow diagram of an example process 1300 for performing noninvasive blood glucose monitoring of a user. The process 1300 may be performed to generate one or more predictions or measurements of a blood glucose level in a user wearing a monitoring devices, such as device 102.

The process 1300 may be executed on a processor (e.g., processors 218). The process 1300 may utilize ML models 104, prediction system 210, and mapping logic 208. Each of the ML models 104, prediction system 210, and mapping logic 208 may be in communication with one or more sensor interfaces 230 and sensors 228, apps 204, processors 1404, and/or memory 202 of device 102 to receive and process sensor signals captured at a body site of a user. The sensor signal may be obtained using device 102 or another device communicatively coupled to device 102. The process 1300 may be performed on device 102, on a companion device (e.g., mobile device), in an on-device app (e.g., app 204), in a third-party app, or on the cloud, or the like.

At block 1302, the process 1300 includes causing a light source to illuminate a body site of a subject. For example, the optional light source 232 or a light source of image sensor 228 may receive instructions to illuminate the body site of a user. The instructions may be provided by a program executing on wearable device 102 or executing on a device communicatively coupled to device 102. The illumination may provide NIR light to the body site.

At block 1304, the process 1300 includes capturing at least one digital image representing reflected light from the body site. For example, the image sensor 228 may capture one or more images (e.g., image signals, digital images, light reflections, digital video, one or more sequences of image frames, etc.) of one or more venous blood vessels (or venous blood vessel portions) viewable on the surface of skin at the body site. In operation, the image sensor 228 may be installed on device 102 in an arrangement to capture an image/image signal of at least one venous blood vessel portion in the image capture. The portion can be used to perform the analysis of glucose levels for the user.

At block 1306, the process 1300 includes programmatically analyzing the at least one image to assess blood glucose for the subject. For example, the wearable device 102 (and/or other computing device communicatively coupled to device 102) may programmatically analyze the captured image(s) to determine a blood glucose level or measurement for the user based at least in part on the characteristics of the reflected light. For example, the wearable device 102 (and/or other computing device communicatively coupled to device 102) may programmatically analyze a captured image to assess blood glucose levels.

In some embodiments, programmatically analyzing the at least one digital image may be performed to compare the at least one digital image to any number of previously captured prior digital images of the body site as a way to ascertain changes in blood glucose levels of the user in response to an event. For example, the analysis of digital images captured by device 102 can be assessed and compared over time to determine past behavior of glucose levels for a specific user and infer future behavior of the glucose levels for the specific user.

At block 1308, the process 1300 includes generating an indication (e.g., indications 250) representing the blood glucose estimate. For example, the analysis described herein may result in an output that is a blood glucose estimate and/or related prediction representing a glucose level for the user of the body site. The output may be further analyzed to generate an indication that may be communicated to an app, the user, or other user with permissions to receive glucose data about the user under test. The indication may be textual, audial, visual (e.g., messages, notifiers, animations, graphical content, image based content, etc.), or a combination thereof, as described in further detail herein.

In some embodiments, the blood glucose estimate may be expressed as a (a) range of values or as (b) a category in a plurality of categories. For example, each class of image features/glucose levels may include a class size of about 5 mg/dL. A total range of clinical significance may be about 54 mg/dL to about 250 mg/dL. In such an example, the outputs of the ML classifier may include (i) about 54 mg/dL to about 59 mg/dL, (ii) about 60 mg/dL to about 65 mg/dL (iii) about 66 mg/dL to about 71 mg/dL, etc. The total number of such output classes may be about 33 classes. In the event that class sizes are configured to be greater than 5 mg/dL, fewer total output classes may be used. Modifying the class size may be used to increase the accuracy of the ML models described herein.

In some embodiments, a classification is not performed and instead a machine learning regression model is utilized by the ML models described herein. In such an example, each integer value in the range of about 54 mg/dL to about 250 mg/dL may represent a potential output of the machine learning regression model.

In some embodiments, the classification may include classifying image features/glucose levels according to color coding. The color coding may pertain to ranges as described elsewhere herein. However, this color coding may ensure that a user may understand a glucose level by recognizing colors that familiarly indicate low glucose, high glucose, average glucose, etc. For example, green may indicate that blood glucose levels are average or good such that no action is being asked of the user. Orange or red may indicate that glucose is becoming higher than average (e.g., orange) or becoming dangerously high or low (e.g., red), which may signal to the user to perform particular actions to correct the glucose level.

In some embodiments, the classification may include classifying image features/glucose levels according to an application-specific unit or scale. For example, the classification may include classifying a particular subject into a particular glycemic level over a predefined number of hours or days.

In some embodiments, the classification may include outputting a change in glucose value. Such a classification may avoid calibration steps that may otherwise be used. For example, a change in glucose after exercise may be −5 mg/dL. Further, for example, a change in glucose after sleeping (e.g., a fasting state) may be −15 mg/dL.

In some embodiments, the indication representing the blood glucose estimate and/or related prediction may include application data (e.g., for or from one or more app(s) 204). The application data may be arranged in a way to present the blood glucose measurements and/or related predictions to the user in one or more of: an email, a display screen, a text message, an audio entry, and a visual indicator (e.g., indicator(s) 250) within a computing device or wearable device associated with the subject or a care provider of the subject.

In some embodiments, the indication representing the blood glucose estimate and/or related prediction may be provided as a notification to one or more interested parties who have (a) indicated an interest in receiving notifications and (b) are approved by the subject. For example, the indication may be associated with one or more rules for sharing indications about a particular user in which the indication pertains.

In some embodiments, a predicted output value or indication 250 about a glucose level for a user may be expressed as a specific number or a range or category. The predicted output value may also be expressed as a measurement or estimate that is estimated to be accurate within a predefined margin of error. The predicted output value may be, at least in part, expressed using one or more colors and/or audio cues within an app 204, for example, to help inform a user, particularly in ways that can reach audiences of varying ages (e.g., children, the elderly, care providers, etc.) and abilities (e.g., hearing or visually impaired). For example, a certain color and/or audio cue may correspond with a certain category or level of glucose in the blood. In this way, if a user has a difficult time interpreting a numerical value, the use of color on the display and/or audio cue may assist in informing the user about a determined glucose level or prediction.

With respect to block 1306, in some embodiments, the analyzing may include segmenting, by a first ML model (e.g., ML model 104a) one or more images into a plurality of regions. The regions may each include at least a portion of a venous blood vessel (e.g., vessel 404a, vessel 406a, vessel 408a, and/or 410a of FIG. 4A). The segmenting performed by ML model 104a may be performed to detect at least one venous blood vessel (or at least a portion of one or more venous blood vessels).

The analyzing performed by wearable device 102 (and/or other computing device communicatively coupled to device 102) may further include analyzing, by a second ML model (e.g., ML model 104b), a visual appearance of at least one of the identified venous blood vessels in the plurality of regions of the image. Analyzing a visual appearance may include analyzing a pixel intensity (e.g., darkness, brightness, etc.) of each venous blood vessel or portion of such a vessel represented in a given image. Each intensity level determined for a region in an image may be compared to predefined glucose data and/or patient data 206 to determine a glucose level estimate (e.g., a glucose prediction) for the user. The ML model 104b may use mapping logic 208 and/or prediction system 210 to determine the glucose level estimate for the user in near real time.

For example, analyzing the visual appearance of one or more venous blood vessels in the plurality of regions includes determining an intensity level of pixels representing a portion of the venous blood vessel(s). For instance, the intensity level of pixels may represent a darkness level or brightness level that may be ascertained by processing the image 400A and determining that pixels representing a first vessel (or vessel portion) are at a first intensity level, while additional vessels (or vessel portions) are at various different intensity levels. The combination of intensity levels of each vessel and/or vessel portion may be further analyzed with other data to generate a glucose level estimate for the user.

In some embodiments, additional analysis of the veins in one or more captured images may be performed and combined with other analysis (e.g., the determined intensity levels of particular veins, prior glucose predictions or measurements, or the like) and/or patient data 206. For example, the ML model 104b may also determine a dehydration level and/or an osmolality level based on one or more features of the pixels representing the portion of at least one venous blood vessel. Such features may include a blood vessel diameter or size of a portion of one or more venous blood vessel in the one or more images. The determination of dehydration levels and/or osmolality levels may be compared to population level data, prior images associated with the user wearing device 102, and/or patient data 206 in order to determine changes in vessel diameter, vessel behavior, and/or vessel size. In some embodiments, the vessel size may include length, width, cross-sectional area, etc.

Another feature that the ML model 104b can determine is a volume of fluid in the portion of the one or more venous blood vessels in one or more image captured by device 102. For example, the ML model 104b may analyze the fluid, particulates, and/or cross-sectional areas and any associated volumes pertaining to the one or more venous blood vessels in one or more of the captured images.

In addition, the second ML model 104b may also perform a classification process to classify the plurality of regions according to predefined glucose levels. For example, each of the veins or vein portions in one or more captured images may be classified into a particular window of glucose measurements based on a visual appearance in an image including any or all of the determined pixel intensity levels, the determined dehydration level approximations, the determined osmolality level approximations, the determined vessel diameters and related size-based parameters, and/or the determined volumes associated with at least a portion of one or more of the venous blood vessels depicted in the one or more captured images.

The wearable device 102 (and/or other computing device communicatively coupled to device 102) may then generate, based on the classifying and on the visual appearance of the at least one vein, a blood glucose estimate for the user. That is, the wearable device 102 (and/or other computing device communicatively coupled to device 102) may utilize the pixel intensity levels, dehydration level approximations, osmolality level approximations, vessel diameters and related size-based parameters, and volumes associated with at least a portion of one or more veins (or vein portions) to generate a predicted glucose level estimate (and/or related predictions or measurements) for a user of the one or more veins or vein portions.

In some embodiments, the process 1300 may further include monitoring the subject over time. For example, the process 1300 may include monitoring the subject with wearable device 102 by repeating the illumination of the body site, repeating the capturing of digital images to capture additional digital images of the venous body site during the monitoring process, and performing additional programmatical analysis of the additional digital images to determine any number of additional blood glucose estimates or predictions for the user. The ML models 104 may perform the additional programmatical analysis to generate a visual mapping depicting the blood glucose estimate and the additional blood glucose estimates in a time-based graph (e.g., shown in FIG. 1 by computing device 106) and as described in additional detail throughout this disclosure.

In some embodiments, the monitoring may be performed continually. In some embodiments, the monitoring may be performed intermittently. In some embodiments, the monitoring may be performed according to a predefined schedule. In some embodiments, the monitoring may be performed according to a predefined event schedule. In some embodiments, the monitoring may be performed on-demand.

In some embodiments, the process 1300 may further include generating a first set of measurements associated with features of the at least one venous blood vessel detected in the at least one digital image at a first point in time. For example, the ML model 104b may assess segmented images of a first set of measurements associated with veins or vein portions in the at least one digital image at time (t). Next, the process 1300 may include generating a second set of measurements for at least one image of the additional digital images corresponding to the same body site in the at least one digital image. The second set of measurements may correspond to the features of the at least one venous blood vessel at a second point in time. Next, the ML model 104b may compare the first set of measurements to the second set of measurements to determine an updated glucose measurement for the user. Additional assessments and/or predictions may also be performed by ML model 104b and such assessments and/or predictions may be provided as output as described in detail throughout this disclosure.

In some embodiments, the process 1300 may be carried out on a computing device in communication with the wearable device 102. For example, the process 1300 may be executed on one or more processors of a smart phone, a smart watch, a mobile gaming device, a laptop computer, a desktop computer, a cloud hosted computer, or the like.

In such an arrangement, the method 1300 may include performing noninvasive blood glucose monitoring of a user. The process may include causing a light source to illuminate a body site of the user, capturing at least one digital image representing reflected light from the body site, programmatically analyzing the at least one digital image by the at least one processor to assess blood glucose for the user. The analyzing may include receiving a segmentation output from a first machine learning model. The segmentation output may include identified venous blood vessel portions in the at least one digital image and image segments representing a plurality of regions of the at least one digital image. The analyzing may further include receiving analysis output from a second machine learning model. The analysis output may include identification of one or more portions in the segments of the at least one digital image and a visual appearance assessment of the portions of the venous blood vessel in the plurality of regions. The analysis may further include receiving, based on the segmentation output and the analysis output, a blood glucose estimate for the user. The process 1300 may include generating an indication representing the blood glucose estimate.

In some embodiments, the first machine learning model and the second machine learning model are accessed on a cloud-based computing device (e.g., cloud servers executing ML models 104) by a noninvasive blood glucose monitor (e.g., wearable device 102) that may monitor the user. For example, process 1300 may be performed on a cloud-based computing device.

In some embodiments, the visual appearance assessment of the portions of the venous blood vessel in the plurality of regions includes determining an intensity level of pixels representing a portion of the at least one venous blood vessel in the at least one digital image and determining an osmolality level based on one or more features of the pixels representing the portion of the at least one venous blood vessel in the at least one digital image. Such features may include a determined vessel diameter of the portion of the at least one venous blood vessel in the at least one digital image and/or a determined volume of fluid in the portion of the at least one venous blood vessel in the at least one digital image.

In some embodiments, the process 1300 may include monitoring, the subject over time, to capture a plurality of additional images, programmatically analyzing the additional images to determine a plurality of additional blood glucose estimates for the subject, and generating a visual mapping depicting the blood glucose estimate and the plurality of additional blood glucose estimates in a time-based graph.

In some embodiments, the image sensor 228 may exchange data (such as captured image and video) over a wireless network or Bluetooth connection to a computer system designed to perform analysis on the image (and potentially video) data captured by the image sensor 228. In some embodiments, that data may be exchanged over a physical link; for example, the software responsible for performing analysis on the captured digital images/videos may reside and execute in the same physical structure as the image sensor 228.

In some embodiments, the light source 232, image sensor 228, and computer system (e.g., computer system 1400 or computing device 106) for running image analysis may be designed with a convenient form factor adaptable for use in a convenient location, such as the kitchen, car, bathroom, or office. Embodiments may also be incorporated into wearable technology, such as wearable device 102, or another device that may be incorporated into clothing or otherwise worn/carried by a human. Embodiments may also be incorporated into mobile phones and other portable devices.

In embodiments where the accuracy of the glucose readings has exceeded a specified threshold, then an alert can be issued to the user and potential other interested/approved parties (such as a care provider or family member) when a glucose level exceeds a predefined threshold of a predefined normal range for the user.

Embodiments may be used to provide useful information to a user pertaining to user health and wellness on a range of topics, including but not limited to (a) the location of veins in the body, (b) the size, diameter, and/or width of veins in the body, (c) the propensity of change in glucose levels after particular predefined or detected events, such as one or more of: a meal, a fast, a physical stressor, an emotional stressor, a sleep event (e.g., excess sleep, sleep deprivation, exhaustion, etc.), a time of day, and a change in estrogen (d) an indirect measurement of dehydration and/or osmolality by measuring water content in the blood or directly measuring osmolality, (e) measuring the fat content in the blood carried by the veins, and/or (f) information about any substance in blood that shows a specific spectral signature in the wavelength range from about 700 nm to about 2500 nm.

EXAMPLE 1

Table 1 below includes data results from an experiment that compared readings generated by a glucometer and readings generated by image sensors. In the experiment, pre-meal and post-meal readings were taken from 33 non-diabetic individuals with consent. Post-meal readings from all participants were taken at exactly 1.5 hours after commencement of a meal. In this example, five different optical sensors were evaluated including Shortwave infrared (SWIR) cameras used with different light sources in the about 1050 nm to about 1550 nm. The Abbott FREESTYLE LITE finger prick glucose meter was used as a reference. The total number of data points collected was 408. Images associated with the experiment are shown in FIG. 5A, FIG. 5B, FIG. 7A, FIG. 7B, FIG. 8A, FIG. 8B, FIG. 9A, FIG. 9B, FIG. 10A, FIG. 10B, FIG. 11A, and FIG. 11B.

image sensor 228), and a software (e.g., within memory 202) for programmatically analyzing images/reflected light captured by the digital camera to capture or generate blood glucose estimates, predictions, and associated data. In some embodiments, system 1400 may represent a portion of the hardware of the wearable device 102.

In some embodiments, computer system 1400 includes one or more processors 1404 (e.g., processors 218), main memory 1406 (e.g., memory 202), ROM 1408, storage device 1410, and communication interface 1418. The at least one processor 1404 may process information. Memory 1406, such as a random-access memory (RAM) or other dynamic storage device, may function to store information and instructions to be executed by processors 1404. Main memory 1406 also may be used for storing temporary variables or other intermediate information during execution of instructions to be executed by processor 1404. Computer system 1400 further includes a read only memory (ROM) 1408 or other static storage device for storing static information and instructions for processor 1404. A storage device

TABLE 1

| | | | | Before meal gluco-meter | After meal gluco-meter | | | |
| --- | --- | --- | --- | --- | --- | --- | --- | --- |
| User #ID | Age Range | Gender | Race/ Ethnicity | reading (mg/dL) | reading (mg/dL) | Delta mg/dL | Meal | (NIR) outputs |
| 1 | 40-44 | M | Indian | 82 | 132 | 50 | Indian white naan and paneer (Indian cheese) | FIG. 7A, 7B |
| 11 | 40-44 | M | Chinese | 98 | 110 | 12 | unknown | FIG. 5A, 5B |
| 12 | 55-59 | F | Vietnamese | 96 | 96 | 0 | corn chips, cheese pizza, salsa, a little cabernet sauvignon | FIG. 8A, 8B |
| 21 | 40-44 | F | Indian | 97 | 92 | −5 | 2 slices of veggie pizza and a cup of Indian chai | FIG. 10A, 10B |
| 26 | 50-54 | M | Indian | 71 | 121 | 50 | 3 wheat rotis, 3/4 cup okra, potato curry, 1/2 cup mango pulp, 1 cup spinach, cucumber, bell pepper salad (no dressing). | FIG. 9A, 9B |
| 33 | 70-74 | F | Indian | 91 | 108 | 17 | Wheat roti, curry (greens, cauliflower), nuts, cream | FIG. 11A, 11B |

Data Results

Data proved that the NIR optical sensor technology is independent of gender, race, and age. It proved about 56% correlation between the delta in finger prick reading and the observed changes by the embodiments described herein. The described embodiments may provide an advantage of detecting possible errors in the conventional glucose meter.

Figure 14:
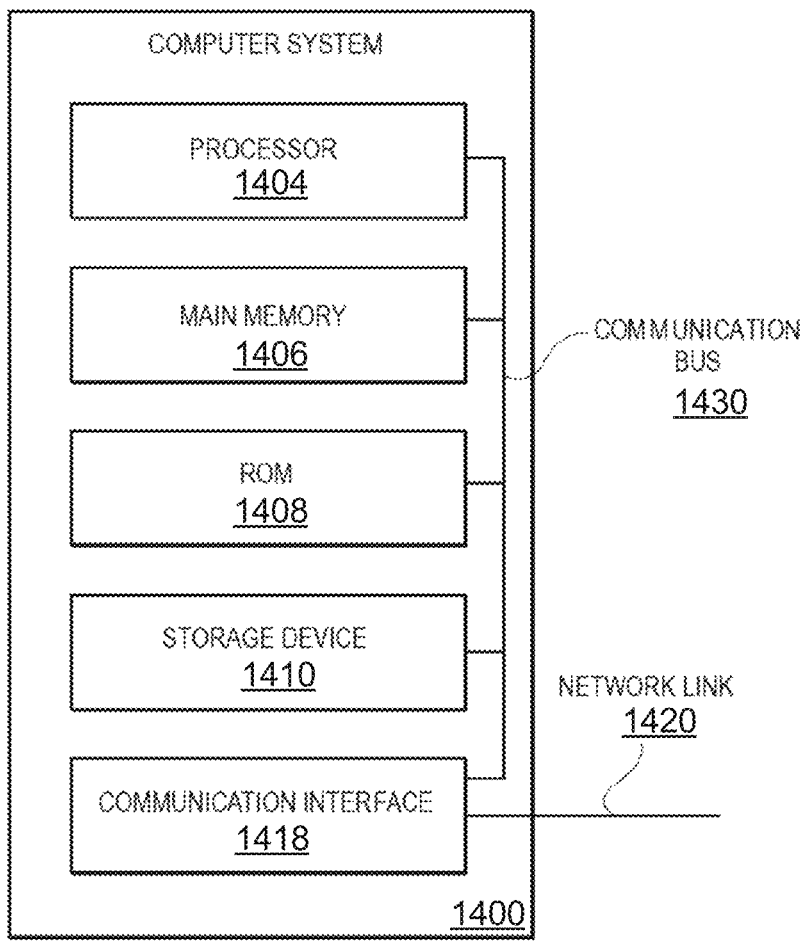
FIG. 14 illustrates a block diagram of an example computing system for performing noninvasive blood glucose monitoring of a user and monitoring well-being and/or glucose.

FIG. 14 is a block diagram of an example computing system for performing noninvasive blood glucose monitoring of a user and monitoring well-being and/or glucose. The computer system 1400 which may control the operation of one or more of a light source (e.g., an IR light source, red-light source, light source 232), a digital camera (e.g., 1410, such as a magnetic disk or optical disk, is provided for storing information and instructions.

The described embodiments are related to the use of computer system 1400 for implementing the techniques described herein. In some embodiments, such techniques are performed by computer system 1400 in response to processor 1404 executing one or more sequences of one or more instructions contained in main memory 1406. Such instructions may be read into main memory 1406 from another machine-readable medium, such as storage device 1410. Execution of the sequences of instructions contained in main memory 1406 causes processor 1404 to perform the process steps described herein. In some embodiments, hard-wired circuitry may be used in place of or in combination with software instructions to implement particular embodiments. Thus, the described embodiments are not limited to any specific combination of hardware circuitry and software.

The term "non-transitory computer-readable storage medium" as used herein refers to any tangible medium that participates in storing instructions which may be provided to processor 1404 for execution. Non-limiting, illustrative examples of non-transitory machine-readable media include, for example, a solid-state device, a floppy disk, a flexible disk, hard disk, magnetic tape, or any other magnetic medium, a CD-ROM, any other optical medium, a RAM, a PROM, and EPROM, a FLASH-EPROM, any other memory chip or cartridge, or any other medium from which a computer can read.

Various forms of non-transitory computer-readable media may be involved in carrying one or more sequences of one or more instructions to processor 1404 for execution. For example, the instructions may initially be carried on a magnetic disk of a remote computer. The remote computer can load the instructions into its dynamic memory and send the instructions over a network link 1420 to computer system 1400.

Communication interface 1418 provides a two-way data communication coupling to a network link 1420 that is connected to a local network. For example, communication interface 1418 may be an integrated services digital network (ISDN) card or a modem to provide a data communication connection to a corresponding type of telephone line. As another example, communication interface 1418 may be a local area network (LAN) card to provide a data communication connection to a compatible LAN. Wireless links may also be implemented. In any such implementation, communication interface 1418 sends and receives electrical, electromagnetic, or optical signals that carry digital data streams representing various types of information.

Network link 1420 typically provides data communication through one or more networks to other data devices. For example, network link 1420 may provide a connection through a local network to a host computer, a mobile phone, or to data equipment operated by an Internet Service Provider (ISP).

Computer system 1400 can send messages and receive data, including program code, through the network(s), network link 1420 and communication interface 1418. For example, a server might transmit a requested code for an application program through the Internet, a local ISP, a local network, subsequently to communication interface 1418. The received code may be executed by processor 1404 as it is received, and/or stored in storage device 1410, or other non-volatile storage for later execution.

Figure 15A:
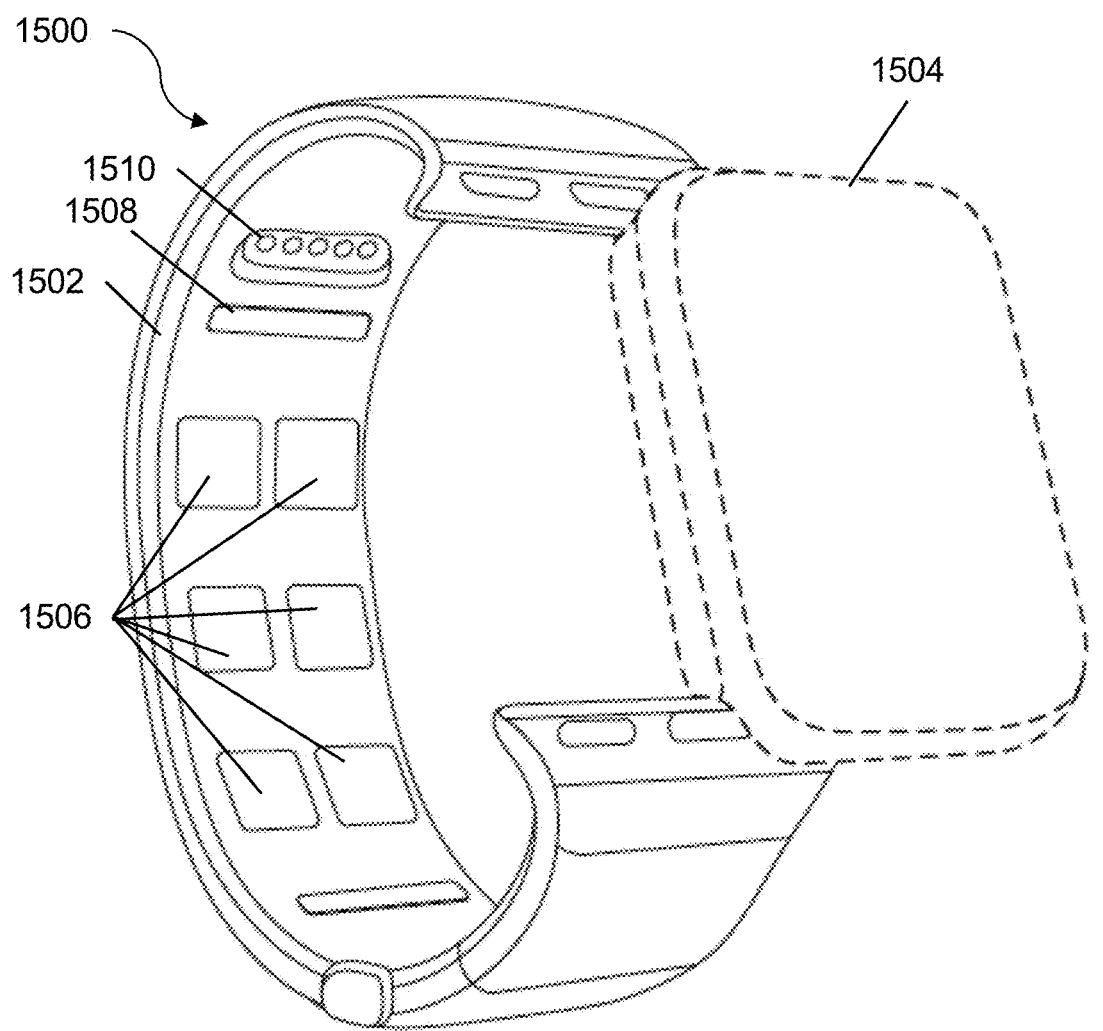
FIG. 15A illustrates an example perspective view of a wearable device for monitoring glucose and user behavior over time.

FIG. 15A illustrates an example perspective view of a wearable device 1500 for monitoring glucose and user behavior over time. The wearable device 1500 may include a band 1502 and an optional watch face 1504. The band 1502 may be communicatively coupled to the watch face 1504 to communicate data for display on watch face 1504. The band 1502 may include electronics for monitoring glucose for a user wearing device 1500. In addition, the band 1502 may include one or more processors coupled to hardware, sensors, or devices for monitoring user behavior, receiving user inputs, and/or generating/displaying recommendations for modifying such user behavior. In some implementations, the device 1500 is communicatively coupled to one or more other computers, smart phones, servers, ML models, or the like.

In this example, the band 1502 includes one or more sensors 1506 (e.g., NIR optical sensor(s) 228, sensors 229, etc.), at least one lens 1508, and one or more LEDs 1510, all of which are depicted on an inner side of the band 1502. The device 1500 may sense user physiological signals on the volar side of the same wrist on which the band is worn.

Figure 15B:
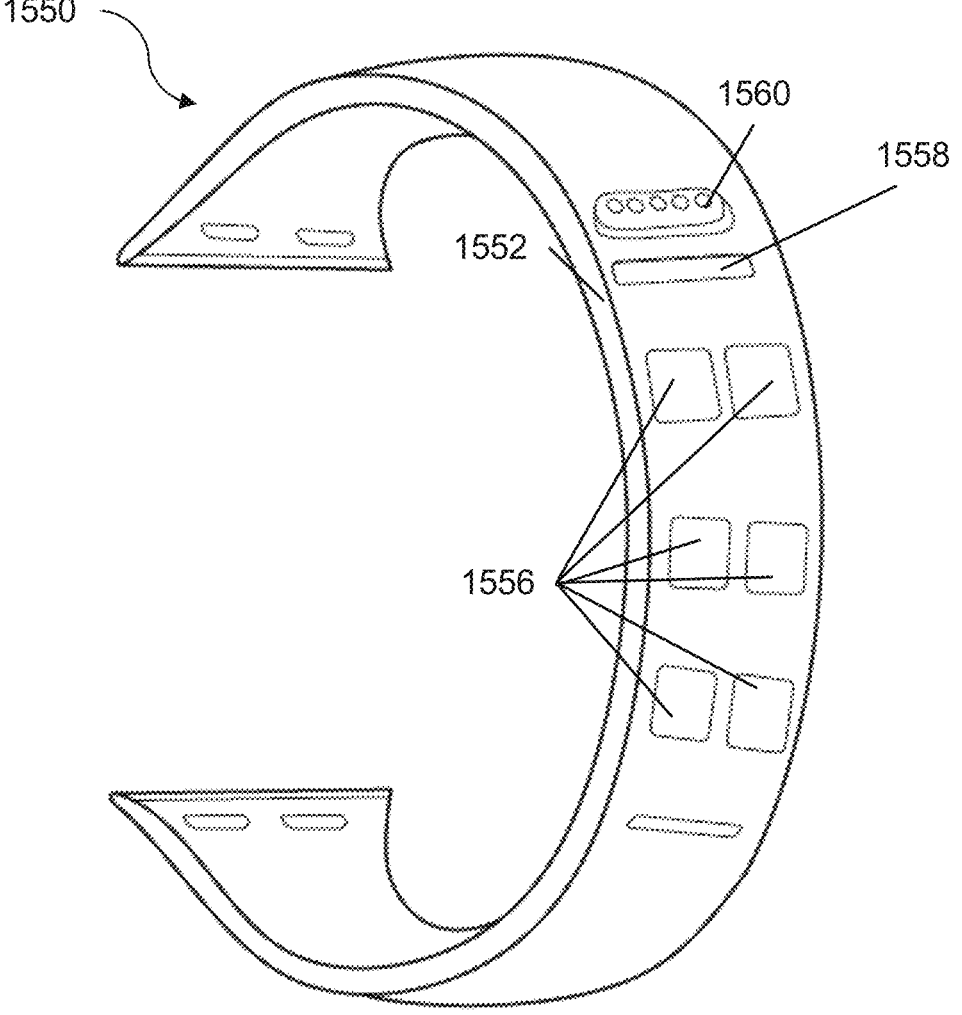
FIG. 15B illustrates an example perspective view of another wearable device for monitoring glucose and user behavior over time.

FIG. 15B illustrates an example perspective view of another wearable device 1550 for monitoring glucose and user behavior over time. The wearable device 1550 may include a band 1552 and an optional smart watch face (not shown). The band 1502 may be communicatively coupled to the smart watch face (not shown) to communicate data for display on the watch face or on a display (not shown) formed within and/or connected to the band 1552. The band 1552 may include electronics for monitoring glucose for a user wearing device 1550. In addition, the band 1552 may include one or more processors coupled to hardware, sensors, or devices for monitoring user behavior, receiving user inputs, and/or generating/displaying recommendations for modifying such user behavior. In some implementations, the device 1550 is communicatively coupled to one or more other computers, smart phones, servers, ML models, or the like.

In this example, the band 1552 includes one or more sensors 1556, at least one lens 1558, and one or more LEDs 1560, all of which are depicted on an outer side of the band 1552. The device 1550 may sense user physiological signals on the volar side of the opposite wrist on which the band is worn, as shown in FIG. 15C and/or as described in FIGS. 12C and/or FIG. 12D.

Figure 15C:
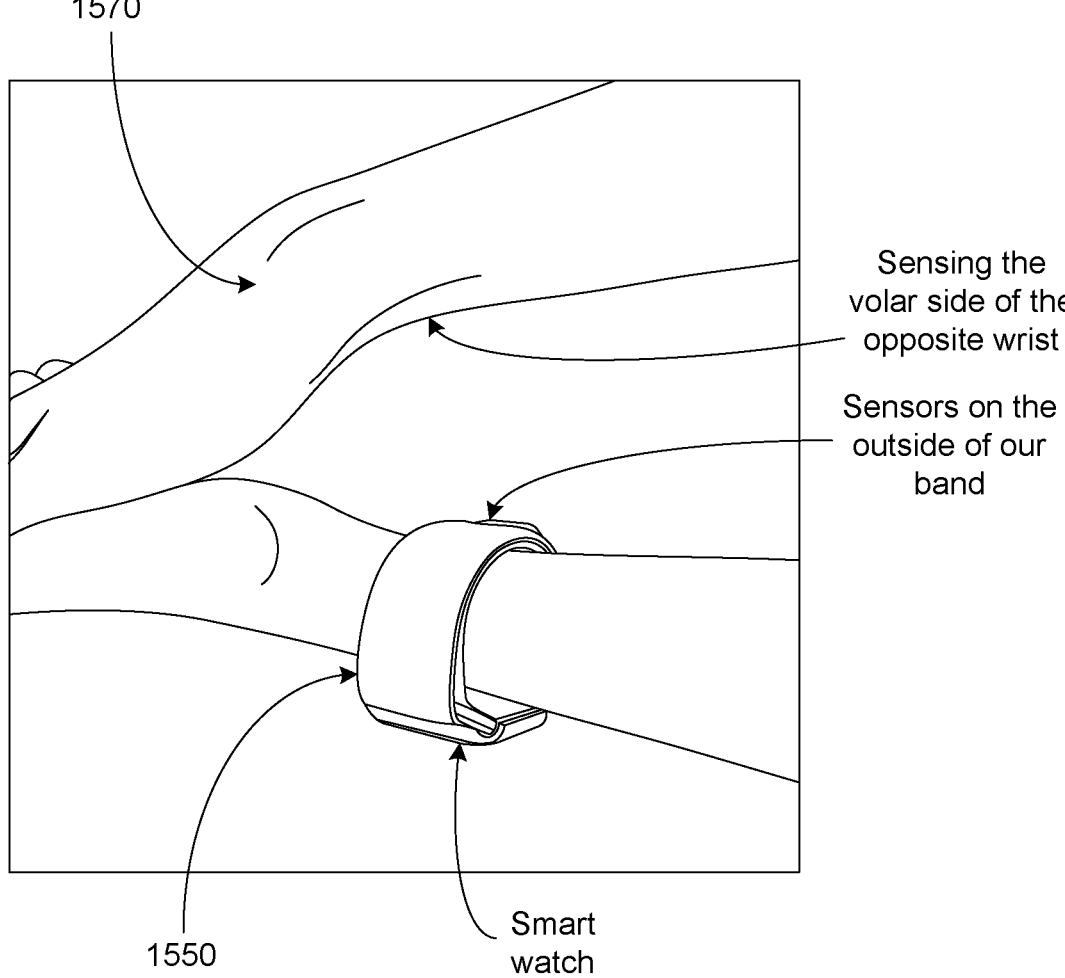
FIG. 15C illustrates an example placement of the wearable device of FIG. 15B.

FIG. 15C illustrates an example placement of the wearable device 1550 of FIG. 15B. In this example, a user 1570 is about to place the volar side of the opposite wrist in which the device 1550 is being worn against or substantially near to one or more sensors (e.g., one or more sensors 1556, at least one lens 1558, and one or more LEDs 1560 shown in FIG. 15B) of device 1550. Once placed against or substantially near to such sensors, the wearable device 1550 may capture one or more measurements (e.g., glucose monitoring measurements, temperature measurements, etc.) as described elsewhere herein.

FIG. 16 illustrates a flow diagram of an example process 1600 for managing blood glucose levels in a subject. The process 1600 functions to ensure that a user may be educated, assisted, supported, or otherwise motivated to modify a health condition and/or behavior to impact overall health. In some embodiments, the process 1600 may be executed by or using a lifestyle AI coach that provides personalized health recommendations, with a focus on glucose management.

At block 1602, the process 1600 includes receiving a plurality of behavioral events. Each behavior event may be correlated to a timestamp within a time period. For example, these events may include blood glucose events, meals consumed, exercise sessions, sleep patterns, and/or stress events, each tagged with a specific time. The timestamp may be used to further assess and/or otherwise determine correlations between event timestamps/events and blood glucose changes. In some embodiments, the process 1600 may include monitoring behavioral events and glucose data over a time period. In such examples, the system 200 may capture both explicit user inputs and physiological measurements that may indicate elevated glucose levels even when symptoms are not present or noticeable to the user.

At block 1604, the process 1600 includes monitoring a plurality of images of a body site captured over the time period. For example, the wearable device 102 may capture images of a wrist at regular intervals throughout a day. In some embodiments, the image capture may instead occur for another body site in which a view of a venous structure portion may be detected by an image sensor. For example, the system 200 may utilize an AI coach or LLM to analyze images for determining glucose patterns and behavioral data to identify rhythms and trends in blood glucose changes. This analysis may enable detection of elevated glucose conditions that typically lack strong symptoms and are not detectable with conventional systems. This may allow the system 200 to inform users of potential glucose abnormalities before clinical testing reveals prediabetes, hypoglycemia, hyperglycemia, or the like.

At block 1606, the process 1600 includes detecting, within each of the plurality of images, an optical characteristic associated with the body site. This may involve analyzing the darkness, size, or volume of veins visible in the captured images, as described in relation to FIGS. 4A-11B. In some embodiments, the detecting may further include other assessments such as a morphometric parameter of the venous structure.

At block 1608, the process 1600 includes determining, for each image and based on the detected optical characteristics, a blood glucose estimation. For example, the system 200 may use ML models 104 to map the visual changes in one or more venous structures to specific glucose levels.

At block 1610, the process 1600 includes identifying a pattern in the determined blood glucose estimations. For example, the system 200 may detect or recognize trends such as post-meal spikes or overnight fasting levels based on a particular pattern identified in one or more blood glucose estimation. In some embodiments, the system 200 may identify patterns in one or more determined blood glucose estimation based on patterns detected or entered by the user including, but not limited to dietary eating patterns, food selection patterns, drug or alcohol consumption patterns, exercise or activity patterns, sleep patterns, stress patterns, and patterns of risk exhibited by the user.

At block 1612, the process 1600 includes correlating at least one behavioral event in the plurality of behavioral events to at least one of the identified patterns. For example, the system 200 may correlate a sharp increase in glucose levels for the user to a particular meal or a gradual decrease to an exercise session.

At block 1614, the process 1600 includes generating, based on the correlating, personalized content for the subject. For example, the system 200 may include tailored dietary recommendations, exercise suggestions, or lifestyle modifications as described in paragraphs elsewhere herein to motivate the user to modify a behavior. Example lifestyle modifications may include meal timing, food ingestion order within meals, optimizing sleep duration, routine stress management in response to daily stressors, encouraging social interaction to help enhance motivation dependent on changes in diet, exercise, mood, etc.

At block 1616, the process 1600 includes generating one or more nudges for the subject based on the personalized content. The one or more nudges may include prompts or suggestions aimed at encouraging adherence to the personalized content. For example, the system 200 may send a reminder to take a walk after a meal that typically causes a glucose spike.

At block 1618, the process 1600 includes causing presentation of the personalized content and the one or more nudges to the subject. For example, the system 200 may generate and present content on the wearable device 102 or a device coupled to wearable device 102. In some embodiments, the information may be sent as a notification to a paired smartphone, one or more buddy devices 110, and/or an AI coach 108.

In some embodiments, the process 1600 may represent a method of treatment for treating a subject having reduced insulin glycemic control. In some embodiments, the process 1600 may represent a method of treatment for treating a subject having poor insulin glycemic control. In some embodiments, the process 1600 may represent a method of treatment for treating a subject to prevent metabolic disease. In some embodiments, the process 1600 may represent a method of treatment for a subject when blood sugar symptoms are lacking detection. For example, the system 200 may determine blood glucose fluctuations when symptoms are not present for the subject. The system 200 may capture glucose data in a noninvasive manner and may assess rhythms of blood glucose change (e.g., using ML models 104, 104a, etc.) and in response, may inform the user even before clinical testing reveals abnormalities. The system 200 may make the user aware of the full implications and down the line consequences of developing diabetes.

In some embodiments, the process 1600 may include assessing psychological aspects of the behavior of a user. For example, the system 200 may use coach 108 and/or ML models 104a to detect or determine default bias patterns that may influence health-related decision making. The system 200 may also detect or determine cognitive biases based on user behavior that could lead to poor health choices or resistance to behavioral changes. Such determinations may be used to generate particular nudges and/or content for the user that account for cognitive biases. In some embodiments, the personalized content may include personalized educational content that includes diagrams and text for making users aware of the full implications and long-term consequences of developing prediabetes, diabetes, and/or maintaining elevated glucose levels. This content may be tailored to overcome identified psychological biases and present information in a manner that resonates with the individual user's cognitive patterns.

In some embodiments, identifying behavioral patterns that correlate with higher risk of glucose spikes may be based on analyzed user data and user history. The system 200 may recognize specific activities, meal choices, timing patterns, or lifestyle factors that may precede glucose elevation events. In some embodiments, the system 200 may present the personalized content, educational materials, and/or behavioral nudges to the user through a user interface, with timing and presentation methods optimized based on glucose patterns and psychological receptivity of the user.

In a non-limiting example, a primary care provider may conventionally have an annual preventive visit with a patient who has prediabetes, elevated blood pressure and rising cholesterol. These are all conditions which benefit from lifestyle change, rather than pharmacologic treatment. Dietary changes, exercise goals, and motivation for behavior change is critical for overcoming these conditions, and the goals and quick strategies are discussed at a primary care visit, but there is no personalized plan of action immediately available to the patient. In this conventional model, there is no monitoring of this behavior and its change until the next annual preventive care visit, unless the patient comes in again for a visit for another issue. This lack of interaction between provider and patient lacks longitudinal support for behavior change. Thus, a year goes by without significant changes to health and without the chance to reverse health risks before the diagnosis of disease occurs. The system 200 may provide lifestyle goal setting and monitoring for the user. For example, after a patient exits a primary care visit, an app (e.g., app 204 or other app accessible on any computing device) may be provided to this patient. The patient may input or import health conditions, and in response, the app will pre-populate goals for diet (e.g., caloric intake and beneficial/adverse food groups to monitor for intake), exercise (e.g., minutes per week of aerobic and strength training), which will form the content of history, context, and prompts provided to the LLM. Using this history and low-burden user-provided demographic, laboratory, habits (e.g., diet preferences, work schedule, preferred exercises, etc.) data, the app may use system 200 to provide scheduled nudges to begin 1-2 weekly behavior changes. These behavior changes will progressively update based on achieving goals. The system 200 may utilize natural milestones (e.g., the beginning of a school/work year, birthdays, vacations, etc.) to align goals for the year. In some embodiments, guidance may be automated for a set time period (e.g., 3 months, 6 months, 1 year, etc.) and may result in a suggestion for repeat testing and a primary care provider visit at the end of this time period. The app can track progress on these lifestyle changes using a combination of user-reported and passive data collected by mobile device health apps, wearable device data, etc.

In some embodiments, the process 1600 may further include correlating the contents of a last consumed meal to the determined blood glucose estimation, and generating feedback on the last consumed meal as part of the personalized content. For example, the system 200 may receive an indication from a user of wearable device 102 that the last consumed meal included white rice, teriyaki chicken, and a soda. The wearable device 102 may detect a glucose response at some time after the meal. For example, a glucose response may be detected as 185 mg/dL indicating a postprandial spike. The lifestyle AI coach 108 may assess the detected glucose response and the meal and may provide feedback. Example feedback for this example may include a message or indication such as 'your blood sugar spiked higher than expected after your last meal. The white rice and soda are likely contributors due to having a high glycemic index. For a more stable blood sugar response, try substituting white rice with brown rice or *quinoa*, and replace soda with water or unsweetened tea.'

In another example, the system 200 may receive an indication from a user of wearable device 102 that the last consumed meal included grilled salmon, *quinoa*, and steamed broccoli. The wearable device 102 may detect a glucose response at some time after the meal. For example, a glucose response may be detected as 110 mg/dL, which may be determined to be within a target postprandial range. The lifestyle AI coach 108 may assess the detected glucose response and the meal and may provide feedback. Example feedback for this example may include a message or indication such as 'Great job! Your blood glucose stayed within a healthy range after your meal. The protein and fiber from salmon and vegetables likely helped slow digestion and glucose absorption. Keep up the balanced meals.'

In another example, the system 200 may receive an indication from the user that the last consumed items were a granola bar and a fruit smoothie. The wearable device 102 may detect a glucose response of approximately 165 mg/dL after consumption. The lifestyle AI coach 108 may assess this elevated response and correlate it with the reported intake. Example feedback may include an indication such as 'although your snack choices seemed healthy, the granola bar and smoothie may have had added sugars. Try checking the labels for total sugar content and opt for whole fruit and nuts instead next time.'

In yet another example, the system 200 may detect that a user consumed cheese pizza at approximately 10:30 PM. A fasting glucose level measured by the wearable device 102 the following morning may indicate an elevated blood glucose response value of approximately 125 mg/dL. The system 200 (e.g., lifestyle AI coach 108 or agent 109) may evaluate the temporal relationship between the meal and the glucose reading and provide feedback such as 'your fasting blood sugar was elevated this morning, which may be linked to your late-night meal. Try to finish eating 2-3 hours before bedtime to help your body stabilize glucose levels overnight.'

In a further example, the system 200 may receive input that the user consumed a chicken wrap and an apple. Additionally, activity sensor data (e.g., from one or more sensors 229) may indicate that the user engaged in 30 minutes of walking shortly after the meal. The wearable device 102 may detect a mild glucose elevation to approximately 98 mg/dL with a quick return to baseline levels. The lifestyle AI coach 108 may correlate the physical activity with the favorable glucose trend and provide feedback such as 'Excellent response! Light activity after meals can improve your body's glucose handling. Your walk after lunch helped minimize your blood sugar increase. Consider making this a regular habit.'

The process 1600 may also include generating feedback that may suggest timing for a next meal and/or educational content. The educational content may include a meal plan for a user to follow as a way to minimize glucose spikes over a second time period. The second time period may be determined and/or otherwise selected by system 200 based at least in part on the blood glucose estimations determined for the user.

In some embodiments, the process 1600 may further include monitoring a behavior or input responsive to the presentation of the one or more nudges. For example, food input, exercise input, and/or detected blood glucose levels may be monitored over time. The process 1600 may iteratively repeat the monitoring of additional images of the body site, for example to determine updated blood glucose levels for the user. The process 1600 may then update the personalized content and nudges based on any detected additional inputs, behavioral events, and images. In some embodiments, the process 1600 may also include adapting the personalized content based on contextual information associated with the subject, such as current location, time of day, upcoming events, or recent activities. For example, if the system 200 nudged the user to take a walk after a meal and the user complied (according to the monitoring) and the walk resulted in improved glucose levels, the system 200 may reinforce this behavior in future recommendations.

In some embodiments, the process 1600 may include determining a nudge mode from a plurality of nudge modes based on the plurality of behavioral events and the monitoring of the plurality of images, and generating the one or more nudges according to the determined nudge mode. In some embodiments, the nudge mode may represent an indication of how many nudges may be provided to a user over a time period. In some embodiments, the nudge mode may represent which words to use in the nudges where a light mode may provide suggestions or general guidelines, a heavy mode may provide rules to abide by and/or explicit meal plans, exercises, and/or timing of both. The nudge mode may be determined by the AI coach 108, the wearable device 102, or may be user selected at device 102 (or a companion device coupled to device 102). In some embodiments, nudge modes may also be defined by a tone and/or approach of the lifestyle AI coach 108. The tone and/or approach may be defined for each nudge mode and may be dynamically adjusted based on user feedback. For example, the system 200 may implement a quick poll using emojis to gauge a current emotional state of the user, which may trigger the AI coach 108 to generate empathetic or assertive approaches, accordingly.

In a non-limiting example, if a user links a support family member or friend (e.g., buddy device 110) and notes messages between the two individuals, the electronic nudge may be skipped in favor of the personal interaction between the two individuals. The nudge mode may then adapt to suggest this personal interaction at regular intervals in the future.

In some embodiments, the process 1600 may further include determining a glucose time in range for a user based on the blood glucose estimations determined for the user over time. The process 1600 may then generate a time to trigger the presentation of the one or more nudges based on the glucose time in range. For example, if the determined glucose blood levels are consistently within range, the system 200 may reduce the frequency of nudges to weekly check-ins. Similarly, if the detected blood glucose levels frequently fall out of range in the evenings, the system 200 may increase the frequency of evening nudges to encourage healthier choices.

In some embodiments, the process 1600 may include generating a grocery shopping list curated according to the blood glucose estimations, and may automatically place items from the list in an online shopping cart and/or may place an order for the items. For example, if the glucose levels for a user indicate a lack of or a reduced amount of fiber as compared to a predefined fiber goal, the system 200 may generate a shopping list of high-fiber foods and may also place an order for delivery or pickup of the proposed items.

The systems and methods described herein and variations thereof can be embodied and/or implemented at least in part as a machine configured to receive a computer-readable medium storing computer-readable instructions. The instructions may be executed by computer-executable components integrated with the system and one or more portions of the processor on the assemblies described herein and/or computing devices 102, 108, 110, etc. The computer-readable medium can be stored on any suitable computer-readable media such as RAMs, ROMs, flash memory, EEPROMs, optical devices (e.g., CD or DVD), hard drives, floppy drives, or any suitable device. The computer-executable component may include any suitable dedicated hardware or hardware/firmware combination that can alternatively or additionally execute the instructions.

FIGS. 17A-17B illustrate an example user interface 1700 of a conversational exchange depicting an interaction sequence between a user and an AI-driven user interface. FIG. 17A illustrates a user interface 1700 that depicts content and prompts that function to guide a user to a personalized set of healthy grocery recommendations at stores proximate to the user. The recommendations may be provided through an adaptive prompt-response framework, such as system 200 (e.g., agent 109 or lifestyle AI coach 108). Each AI output is informed by structured logic layers, including intent classification, context acquisition, location-based filtering, and affordability heuristics. The system 200 may improve user experience in real-time grocery planning scenario and may be extended to restaurant recommendations, nutrition analysis, and/or digital couponing applications.

A user of wearable device 102, for example, may initiate a session by transmitting a general query, such as "hello." In response, the system 200 analyzes the user input and generates a context-relevant follow-up query, aimed at refining the scope of assistance. The system, 200 may prompt the user with a disambiguating question 1702, such as 'Are you looking for healthy items in a nearby grocery store or healthy options on the menu of a specific restaurant?' This step initiates the intent detection module (not shown) of the system 200, which classifies the query under a grocery-focused information retrieval context when the user responds with the keyword grocery. The system 200 may then proceed to refine the inquiry by soliciting additional contextual information, including geographic and economic constraints 1704. This stage engages the context enrichment engine (not shown), which may collect geospatial and budgetary parameters to support localized and personalized recommendations.

Upon the user providing a zip code and a budget, the system 200 may generate personalized grocery store recommendations. In this example, the user provides two inputs: a zip code (94027) and a budget ($97). These inputs are parsed and tokenized by the system 200. Subsequently, the system 200 accesses a database of grocery stores mapped to the provided zip code. Based on criteria including distance, customer ratings, price level, and product availability, the system 200 returns a structured list of top grocery options. This output is presented in a ranked and enumerated format (e.g., 1 to 3) to facilitate user comprehension and decision-making. The formatting and prioritization logic is driven by a multi-criteria scoring algorithm, which weighs the importance of review ratings, affordability, and physical proximity to the zip code centroid. In some embodiments, the system 200 may further refine or filter store recommendations based on the provided budget (e.g., $97). While the illustrated response does not explicitly tie pricing to individual product suggestions, in additional embodiments, the system 200 may interface with retailer APIs to assess whether recommended stores offer a sufficient quantity of healthy foods (e.g., fresh produce) within a particular declared budget.

FIG. 17B illustrates a user interface 1710 depicting a continuation of the user interface 1700. User interface 1710 includes further interaction between the user and the AI-driven system 200. For example, after the user selects a grocery store from the provided options, the system 200 proceeds to offer personalized healthy food recommendations 1712.

The user responds to the grocery store recommendations by selecting 'Trader Joe's'. The system 200 acknowledges this choice and initiates the next phase of assistance, focusing on healthy food recommendations. The system 200 may prompt the user with additional questions, such as: 'Great choice! What kind of healthy foods are you interested in? (e.g., fruits, vegetables, lean proteins, whole grains)'. This question serves to narrow down user preferences and dietary interests. Other questions are possible. The system 200 processes any user input responses and may generate a tailored list of healthy fruit and vegetable recommendations, as shown in FIG. 17C and FIG. 17D. The recommendations are presented in a structured, easy-to-read format, with each item accompanied by its potential health benefits. The user interface 1710 in FIG. 17B showcases the ability of system 200 to provide personalized, context-aware recommendations while maintaining an engaging conversation flow. The AI-driven interface adapts to user responses, offering relevant information and anticipating potential next steps in a healthy grocery shopping journey for the user.

FIG. 17C illustrates a user interface 1720, which represents a further continuation of the user interface 1700 and 1710, showing the ongoing interaction between the user and the AI-driven system 200. After the user expresses interest in a week of healthy food items at Trader Joe's, the system 200 provides the list. Each element in the list includes the name of the food, a price, and an educational portion (e.g., portion 1722) to teach the user about the food item and how that item may impact the human body.

FIG. 17D depicts a user interface 1730 illustrating a final part of this conversational exchange of the user interfaces 1700, 1710, and 1720, showcasing a capability to provide additional health-related information and wrap up the interaction with additional food items and educational content (e.g., content 1732) and a total cost 1734. The system 200 may provide a summary of how the food item combination provides nutrition and fits within a predefined budget (e.g., content 1736). In some embodiments, the user interface 1730 may further include prompts to check if the user wishes to add items to an electronic/online shopping cart and/or place an order at Trader Joe's online for the proposed items. If the user requests to fill an online shopping cart, the system 200 may do so and add the items to an electronic shopping cart for the selected store and items indicated in the output of user interfaces 1700, 1710, 1720, and 1730. If the user requests to make the purchase, the system 200 may function to fill the online shopping cart and present payment options to the user. In some embodiments, the system 200 may perform the purchase, for example, if the user preconfigured payment options and automated cart purchases. In some embodiments, the system 200 may add items suggested for purchase to an existing electronic shopping cart. This functionality demonstrates the ability of system 200 to integrate recommendations with practical shopping assistance.

FIGS. 18A-18B illustrate example user interfaces 1800 of a conversational exchange depicting an interaction sequence between a user and an AI-driven user interface for providing personalized restaurant based recommendations. The recommendations may be provided through an adaptive prompt-response framework, such as system 200 (e.g., agent 109 or lifestyle AI coach 108).

FIG. 18A illustrates an example user interface 1800 of a conversation about a restaurant the user wishes to visit. In this example, the system 200 provided at the request of the user, a list of health options at a McDonald's restaurant. Each item lists calories 1802, sugar content 1804, carbohydrate content 1806, and an educational description 1808.

FIG. 18B illustrates an example user interface 1810 of a conversation about another restaurant the user wishes to visit. In this example, the system 200 provided at the request of the user, a list of health options at a Starbucks restaurant. Each item lists calories, sugar content, carbohydrate content, and an educational description 1812. Additional educational help and/or suggestions 1814 may be provided based on user goals and/or blood glucose levels known to system 200.

Figure 19:
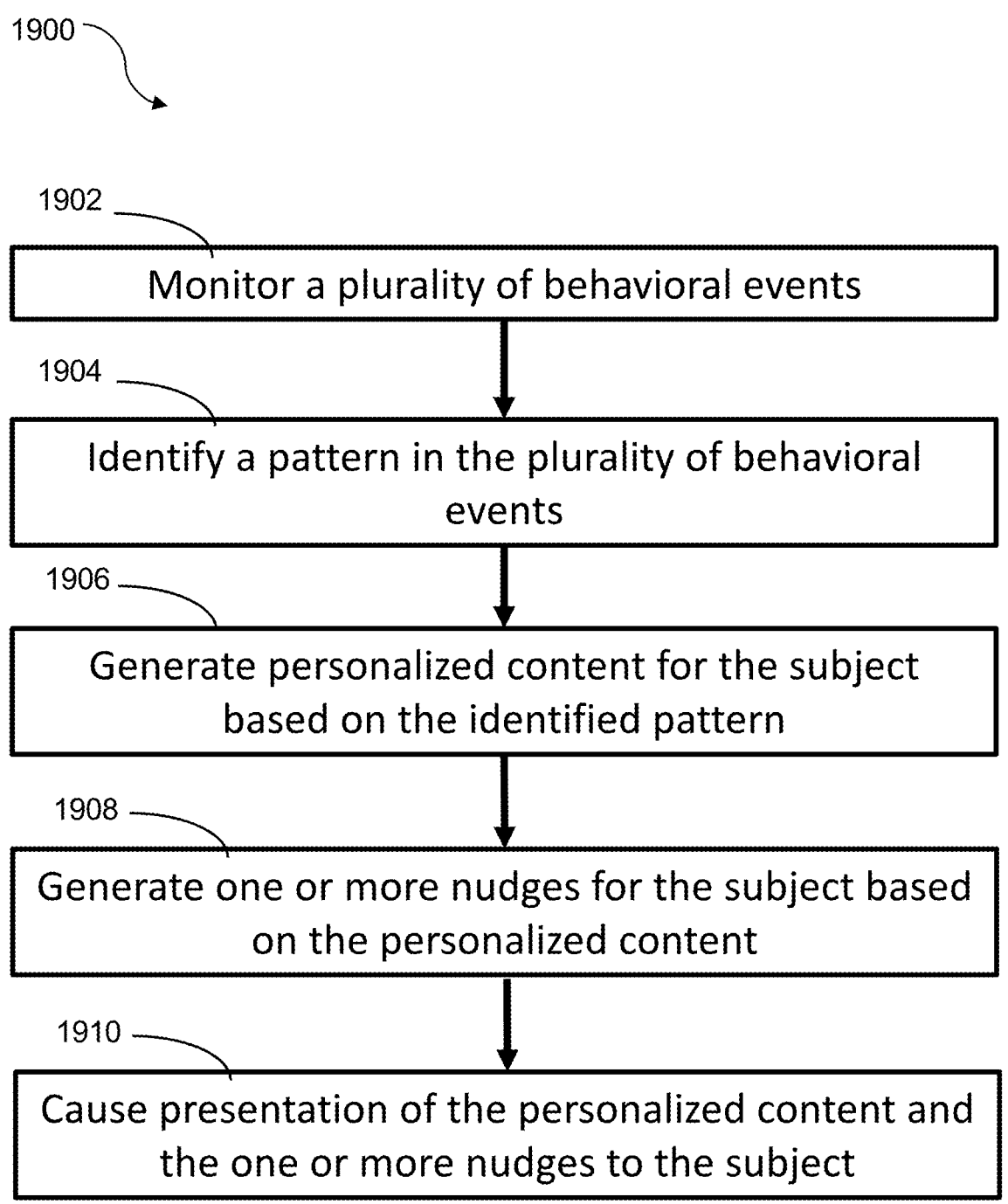
FIG. 19 illustrates a flow diagram of an example process for managing behavior in a subject.

FIG. 19 illustrates a flow diagram of an example process 1900 for managing behavior in a subject (e.g., a user). The process 1900 functions to ensure that a user may be educated, assisted, supported, or otherwise motivated to modify a health condition and/or behavior to impact overall health. In some embodiments, the process 1900 may be executed by or using a lifestyle AI coach that provides personalized health recommendations, with a focus on particular behaviors or patterns of behaviors. In some embodiments, process

1900 may be executed by a processor, such as processor 218. In some embodiments, process 1900 may be executed by a processor and receive additional data from AI coach (e.g., coach 108) and/or other ML model (e.g., ML model 104a, ML model 104b, or the like).

At block 1902, the process 1900 includes monitoring a plurality of behavioral events. Each event may be correlated to a timestamp within a time period. For example, each event may occur at the timestamped time. In some embodiments, each event may be entered or detected by one or more components of the system 200. In some embodiments, the system 200 may monitor particular behaviors using one or more sensors 228 and/or 229 on wearable device 102. In some embodiments, the system 102 may monitor the behaviors using other devices communicatively coupled to device 102 and/or coach 108. In some embodiments, the system 200 may receive behavioral events as data from a third party, a user, a lifestyle coach 108 or the like.

For example, the system 200 may monitor for or receive behavior and/or behavior events corresponding to a user. The behaviors and/or behavior events may include meals consumed, exercise sessions, sleep patterns, stress events, or other behaviors described elsewhere herein. Each behavior or behavior event may be tagged with specific timestamps. For example, the system 200 may track naan and paneer consumed at a specific time, or 3 wheat rolls and 3/4 cup okra eaten at another timestamp.

In some embodiments, the monitoring may include monitoring or receiving blood glucose data for the subject. Identifying the pattern in the plurality of behavioral events may include identifying a glucose time in range for the subject. The system may use such data to select, based on the glucose time in range, one or more times in which to present the one or more nudges to the subject. For example, the system 200 may adjust frequency based on glucose control. If the time in range is consistently high, the system 200 may reduce monitoring frequency to weekly checks. However, if values begin to fall out of a predefined range more often, the AI coach 108, for example, may adapt by deploying more frequent reminders or nudges.

At block 1904, the system identifies a pattern in the plurality of behavioral events. For example, the system 200 may analyze the collected behavioral data and detect recurring trends, correlations, or sequences that may impact the health of the user, such as glucose regulation, food intake, etc., The pattern identification may reveal subtle behavioral rhythms that precede glucose spikes or other health-related events, even when clinical symptoms are not yet apparent to the subject. For example, the system 200 may detect trends such as post-meal spikes or overnight fasting levels based on a particular pattern identified in one or more blood glucose estimation. In some embodiments, the system 200 may identify when consistent nighttime glucose spikes are detected for a user during Ramadan, for example. In response, the AI coach 108 may adjust recommendations and shift to a light mode of nudging until the end of the fasting period. In some embodiments, the system 200 employs ML models 104 to analyze changes over time and assess blood glucose or other past behaviors to infer future behaviors for the user.

In some embodiments, the system 200 may correlate multiple types of behavioral events with physiological measurements. For example, the system 200 may determine temporal correlations by tracking frequency and timing of meals and analyzing glucose spike patterns to identify relationships between eating behaviors and physiological responses. The system 200 may also integrate contextual data. For example, the system 200 may process mobile device-type measurements or wearable device measurements including frequency of phone/app interaction and patterns of use, frequency and pattern of communication via text message, email message, phone call, or voice message, and/or location services accessed during particular time periods (e.g., restaurant, game, work, home, vacation).

In some embodiments, the system 200 may identify complex behavioral patterns by correlating multiple data streams, applying machine learning algorithms, and continuously refining pattern recognition through iterative analysis of user responses and physiological feedback.

At block 1906, the process 1900 includes generating personalized content for the subject based on the identified pattern. The personalized content may include one or more of: dietary recommendations, exercise suggestions, and lifestyle modifications. In some embodiments, at least one of the plurality of behavioral events may include a last consumed meal and the personalized content may include feedback on the last consumed meal. The feedback may include suggested timing for a next meal and educational content. The educational content may include a meal plan for the subject that minimizes glucose spikes over a second time period. For example, if the system 200 determines behavior trending toward increased blood glucose levels, the system 200 may refine guidance or feedback to prompt the user to consume protein-containing foods first at a next meal.

The system 200 may generate and tailor recommendations in the form of personalized content for the subject. The personalized content may provide tailored feedback and recommendations based on meal intake, detected glucose response, and/or contextual behaviors of the user. For example, the system 200 may assess glucose levels for the user following a specific meal and may generate interpretive feedback indicating how the contents of the meal (e.g., such as high glycemic index foods) contributed to a postprandial spike. This feedback may include suggestions for alternative food options, such as substituting white rice with brown rice or *quinoa*, or replacing soda with water or unsweetened beverages, thereby guiding the user toward more stable glucose responses. When the system 200 detects a favorable glucose response, positive reinforcement messages may be generated that commend the user for a well-balanced meal, encouraging continued adherence to healthy dietary habits. In cases where meals perceived as healthy produce unexpected glucose elevations, the system 200 may provide explanatory content highlighting the potential presence of added sugars or refined ingredients, coupled with tips for improved label reading or more nutrient-dense alternatives. The system 200 may also account for behavioral context such as the timing of a meal, and may further offer temporal advice (e.g., avoid late-night eating to improve fasting glucose outcomes). Moreover, when physical activity is detected post-meal and correlates with a favorable glucose trend, the system 200 may reinforce this behavior by informing the user that the performed walk helped minimize a blood sugar increase and nudges may be scheduled to suggest the walk be repeated regularly. Through these dynamic, context-sensitive interactions, the system 200 may deliver personalized coaching that adapts to the unique physiology, habits, and preferences of the user to promote improved glycemic control and long-term health outcomes.

At block 1908, the process 1900 includes one or more nudges for the subject based on the personalized content. The one or more nudges may include prompts or suggestions aimed at encouraging adherence to executing suggested behavior changes provided in the personalized content. For example, one or more nudges may be generated and provided by system 200 to indicate that the user should attempt to decrease refined carbohydrates and increase high fiber and protein in each meal responsive to detecting a pattern indicating that post-prandial glucose is continually highly elevated after meals. The system 200 may continue with another nudge if the first nudge did not motivate the user to modify the meals accordingly. The second nudge may include suggestions about performing post-prandial light exercise with timers and nudges towards 30 minutes of moderate intensity exercise per day.

In another example, the system 200 may generate a prompt that includes a nudge warning against drinking more than two drinks, for example, if the user is at a bar with friends at night, as this can cause a significant glucose spike. In yet another example, the system 200 may generate a prompt that includes a nudge that preemptively suggests foods high in fiber and protein in response to determining prior habits or patterns for the user resulted in over-eating and high glucose when a user is home alone at a particular time.

At block 1910: The system 200 causes presentation of the personalized content and the one or more nudges to the subject. For example, the system 200 may generate content and/or user interfaces and present such content in the user interfaces, browsers, and/or apps 204. In some embodiments, the system 200 may generate and present the personalized content through buddy devices 110, lifestyle AI coach 108, or another interface associated with the user. In general, the system 200 may present the personalized content and/or nudges through various formats including, but not limited to: short games, popups, text messages, emails, summary screens, alerts based on blood glucose levels, prompts for logging diet intake, etc. The presentation may occur on the wearable device 102 or another device communicatively coupled to wearable device 102. In some embodiments, the presentation may occur or be sent as a notification to a paired smartphone, one or more buddy devices 110, and/or an AI coach 108.

In some embodiments, the process 1900 may represent a method of treatment for treating a subject having reduced insulin glycemic control as assessed by behavioral analysis. In some embodiments, the process 1900 may represent a method of treatment for treating a subject having poor insulin glycemic control. In some embodiments, the process 1900 may represent a method of treatment for treating a subject to prevent metabolic disease by modifying behaviors over time. In some embodiments, the process 1900 may represent a method of treatment for a subject when blood sugar symptoms are lacking detection. For example, the system 200 may determine blood glucose fluctuations when symptoms are not present for the subject. The system 200 may capture behavioral data in a noninvasive manner and may assess rhythms of behavior (e.g., using ML models 104, 104a, etc.) and in response, may inform the user even before clinical testing reveals abnormalities. The system 200 may make the user aware of the full implications and down the line consequences of developing prediabetes and/or diabetes.

In some embodiments, the operations of process 1900 may be performed by an artificial intelligence computer agent (e.g., predictive system 210 and/or generative system 209, generative system 209a and/or prediction system 210b, etc.) that may use data generated by monitoring the behavior of the subject and a number of template guides to generate the one or more nudges. Such nudges may be used to coach the subject to modify the behavior over an upcoming time period. In some embodiments, the operations of process 1900 are carried out locally on wearable device 102 by an app 204.

In some embodiments, the process 1900 may further include monitoring a behavior or input responsive to the presentation of the one or more nudges and iteratively repeating the monitoring of behavior exhibited by the subject. In response to detecting additional behavioral events, the system 200 may identify an additional pattern in the additional behavioral events and may update the personalized content according to the additional behavioral events based on the identified additional pattern. The system 200 may generate an updated nudge corresponding to the updated personalized content and may cause presentation of the updated nudge and the updated personalized content to the subject.

For example, the system 200 may track user compliance, such as monitoring the user over time. If the system 200 nudged the user to take a walk after a meal and the user complied (according to the monitoring) and the walk resulted in improved glucose levels, the system 200 may reinforce this behavior in future recommendations. Similarly, the system 200 may adapt based on new data. For example, if the lifestyle AI coach 108 detects systematic elevations in glucose levels over the course of a month for the user, the system 200 may provide nudges reminding the user of healthful meal components and encourage the reintroduction of routine exercise.

The process 1900 may include determining a historical adherence to previous nudges or recommendations generated and/or presented to the user. The historical adherence may be used to select a nudge mode from a plurality of nudge modes. Example nudge modes may include a light mode, a regular mode, and a heavy mode. The light mode may be activated during at least one of: holidays, travel, postpartum periods, short-term illnesses, or user-designated cheat days. The heavy mode may be activated during at least one of: periods following discontinuation of one or more medications (e.g., GLP-1$s$, supplements, insulin, etc.) or when the subject sets aggressive health goals. The regular mode may represent a mode between the light mode and the heavy mode. In general, the one or more nudges may be generated according to a determined (or otherwise configured) nudge mode.

The process 1900 may further include adapting the personalized content based on contextual information associated with the subject. The contextual information may include at least one of: a current location, a time of day, one or more upcoming events, or one or more recent activities. In general, the system 200 may adapt based on circumstances of the user. For example, if a user is attending a conference and unable to adhere to typical recommendations, the lifestyle AI coach 108 may inquire about the conference details and adjust a nudging mode or strategy, accordingly, thereby resuming normal (e.g., regular, standard mode) recommendations after the conference concludes.

In some embodiments, the personalized content described herein may include a grocery shopping list curated according to the identified pattern. The process 1900 may use such information to further perform automatic placement of a plurality of items on the grocery shopping list in an online shopping cart or automatic placement of an order of the plurality of items on the grocery shopping list.

In some embodiments, the personalized content described herein may be presented as one or more venues and a grocery shopping list curated according to the identified pattern, a budget, a location of the subject, and a determination of an availability of a plurality of items on the grocery shopping list. For example, the system 200 may determine, based on user location and budget, which venues (e.g., grocery stores) to present to the user according to the location, the budget, and a determination of availability of health-based food and particular listed grocery items on the shopping list. The process 1900 may further include automatically placing the plurality of items on the grocery shopping list in an online shopping cart or automatically placing an order of the plurality of items on the grocery shopping list, as shown in further detail in FIGS. 17A-18B.

In a non-limiting example, one or more grocery store venues may be selected and suggested by system 200 based on one or more of: a proximity to the user, user budget, and availability of healthy items. In some embodiments, a grocery list may be automated based on the system 200 determining a venue and a day of the week. The system 200 may perform a web-scrape to provide current products, ingredients, and pricing available at a venue of interest. The system 200 can read and interpret product labels. Thus, the shopping list can be curated according to the identified user patterns and also a determined availability of the products on the list specific to the selected one or more venues.

In some embodiments, the personalized content may include a plurality of restaurant menu suggestions and food data corresponding to each of the plurality of restaurant menu suggestions. The food data may indicate one or more of: calorie content, sugar content, carbohydrate content, and at least one reason for selecting the respective restaurant menu suggestions. In some embodiments, selection of the restaurant may be based on one or more of: identified behavior patterns for the user, user location or proximity, user budget, and availability of healthy items on the menu.

In a non-limiting example, one or more restaurant venues may be selected and suggested by system 200 based on one or more of: a proximity to the user, user budget, and availability of healthy items. Menu items may also be suggested. The process 1600 may further include automatically placing the suggested items form the menu in an online shopping cart for purchasing restaurant food. The system 200 may also automatically perform a purchase of the items in the online shopping cart according to user rules and/or requests.

In some embodiments, the process 1900 may be performed by an artificial intelligence health coach (e.g., AI coach 108) that may be configured to share data with a buddy computing device (e.g., device 110) according to permissions associated with the subject. The shared data may include one or more of: a blood glucose estimation, identified behavioral patterns, a status update corresponding to the subject, and a summary corresponding to the subject. Such data may be multi-modal including, but not limited to one or more of: blood glucose graphs, weights, language or nudges, or the like.

The buddy computing device 110 described herein may be used with wearable device 102, a CGM or BGM, or as a standalone computing device enrolled as a trusted member with one or more components of system 200.

The systems and methods described herein may be implemented as a mobile application, wearable-integrated platform, or web-based interface. The LLMs/ML models/AI may be integrated with external application programming interfaces or agents to access nutritional databases, monitor physical activity data, or synthesize custom behavioral strategies tailored to individual users' progress and lifestyle constraints.

The term "about" or "approximately," when used before a numerical designation or range (e.g., to define a length or pressure), indicates approximations which may vary by (+) or (–) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The systems and methods of the embodiments described herein and variations thereof can be embodied and/or implemented at least in part as a machine for receiving a computer-readable medium storing computer-readable instructions. The instructions may be executed by computer-executable components integrated with the system and one or more portions of the processor on the wearable device and/or computing device. In some embodiments, the instructions may be executed by computer-executable components that are in communication with the wearable device. The computer-readable medium can be stored on any suitable computer-readable media such as RAMs, ROMs, flash memory, EEPROMs, optical devices (e.g., an image or DVD), hard drives, floppy drives, or any suitable device. The computer-executable component may be a general or application-specific processor, but any suitable dedicated hardware or hardware/firmware combination can alternatively or additionally execute the instructions.

As used in the description and claims, the singular form "a", "an" and "the" include both singular and plural references unless the context clearly dictates otherwise. For example, the term "sensor" may include, and is contemplated to include, a plurality of sensors. At times, the claims and disclosure may include terms such as "a plurality," "one or more," or "at least one;" however, the absence of such terms is not intended to mean, and should not be interpreted to mean, that a plurality is not conceived.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A computer-implemented method for treating or preventing progression of prediabetes, diabetes, or metabolic syndrome in a subject, the method comprising:

providing a wearable device comprising at least one processor, memory, and one or more sensors configured to monitor physiological parameters of the subject;

receiving data for the subject including a condition or risk factors corresponding to prediabetes, diabetes, or metabolic syndrome and physiological data received from the one or more sensors of the wearable device;

monitoring, using the wearable device, a plurality of behavioral events associated with the subject and physiological parameters of the subject, each event being correlated to a timestamp within a time period;

identifying, using the received data input into generative artificial intelligence comprising one or more machine learning models, a pattern in the plurality of behavioral events that correlate with glucose dysregulation or elevated glycemic levels in the subject;

generating, using the generative artificial intelligence and based on the identified pattern and the received data, personalized content for the subject, wherein the personalized content includes tailored interventions to improve glycemic control of the subject;

generating one or more nudges for the subject based on the personalized content, wherein the one or more nudges comprise prompts or suggestions aimed at encouraging adherence to executing suggested behavior changes provided in the personalized content to improve glycemic control for the subject or improve long-term health outcomes for the subject;

automatically adjusting an operational parameter of the wearable device based on the identified pattern, the automatic adjustment comprising changing a monitoring frequency of the one or more sensors; and causing presentation of an indication of the personalized content and the one or more nudges to the subject.

2. The computer-implemented method of claim 1, wherein:

at least one of the plurality of behavioral events comprises a last consumed meal;

the personalized content comprises feedback on the last consumed meal.

3. The computer-implemented method of claim 2, wherein the feedback comprises suggested timing for a next meal and educational content, the educational content comprising a meal plan for the subject that minimizes glucose spikes over a second time period.

4. The computer-implemented method of claim 1, wherein the personalized content comprises one or more of: dietary recommendations, exercise suggestions, and lifestyle modifications.

5. The computer-implemented method of claim 1, wherein the method further comprises:

monitoring a behavior or input responsive to the presentation of the one or more nudges;

iteratively repeating the monitoring of behavior exhibited by the subject;

in response to detecting additional behavioral events, identifying an additional pattern in the additional behavioral events;

updating the personalized content according to the additional behavioral events based on the identified additional pattern;

generating an updated nudge corresponding to the updated personalized content; and causing presentation of the updated nudge and the updated personalized content to the subject.

6. The computer-implemented method of claim 1, wherein the monitoring of the plurality of behavioral events is performed at least in part by an artificial intelligence computer agent configured to use data generated by the monitoring and a plurality of template guides to generate the one or more nudges.

7. The computer-implemented method of claim 1, wherein the method further comprises:

adapting the personalized content based on contextual information associated with the subject, wherein the contextual information comprises at least one of: a current location, a time of day, one or more upcoming events, or one or more recent activities.

8. The computer-implemented method of claim 1, wherein the plurality of nudges are selected from nudge modes comprising a light mode, a regular mode, and a heavy mode.

9. The computer-implemented method of claim 8, wherein the heavy mode is activated during at least one of: periods following discontinuation of one or more medications or when the subject sets aggressive health goals.

10. The computer-implemented method of claim 1, wherein:

monitoring the plurality of behavioral events comprises monitoring or receiving blood glucose data for the subject;

identifying the pattern in the plurality of behavioral events comprises identifying a glucose time in range for the subject; and selecting, based on the glucose time in range, one or more times in which to present the one or more nudges to the subject.

11. The computer-implemented method of claim 1, wherein the personalized content comprises a grocery shopping list curated according to the identified pattern, and the method further comprises automatically placing a plurality of items on the grocery shopping list in an online shopping cart or automatically placing an order of the plurality of items on the grocery shopping list.

12. The computer-implemented method of claim 1, wherein the personalized content comprises a plurality of restaurant menu suggestions selected according to the identified pattern, and food data corresponding to each of the plurality of restaurant menu suggestions, the food data indicating one or more of: calorie content, sugar content, carbohydrate content, and at least one reason for selecting the respective restaurant menu suggestions.

13. The computer-implemented method of claim 1, wherein the computer-implemented method is performed by an artificial intelligence health coach configured to share data with a buddy computing device according to permissions associated with the subject, the shared data comprising one or more of: a blood glucose estimation, identified behavioral patterns, a status update corresponding to the subject, and a summary corresponding to the subject.

14. The computer-implemented method of claim 1, further comprising:

defining a reward milestone associated with a health goal for the subject;

monitoring progress toward the reward milestone;

enrolling a buddy device associated with a trusted contact of the subject to receive status information according to permission settings provided by the subject;

providing an update to the buddy device, the update comprising updates on behavior, food intake, exercise, or physiological changes corresponding to the subject;

receiving feedback from the buddy device about the subject;

in response to determining achievement of the reward milestone, generating reward content comprising a gamified experience using the generative artificial intelligence, wherein the gamified experience is tailored to the subject based on the identified pattern, the feedback from the buddy device, and personal preferences associated with the subject; and causing presentation of the gamified experience to the subject as a reward for achieving the reward milestone.

15. The computer-implemented method of claim 1, further comprising:

defining a health goal for the subject, wherein the health goal includes a target number of meal events satisfying health criteria over a defined time period;

monitoring meal-related behavioral events including:

events indicating selection of home cooked meals, and events indicating selection of healthy options when dining at restaurant venues;

determining meal-related behavioral events that satisfy the health criteria;

calculating progress toward the health goal based on the monitoring;

generating, using the generative artificial intelligence and based on the calculated progress, adaptive recommendations for improving adherence to the health goal, wherein the adaptive recommendations are personalized based on correlations between the monitored meal-related behavioral events and the calculated progress; and causing presentation of progress information indicating the progress relative to the target number.

16. The computer-implemented method of claim 1, monitoring adherence of the subject to the one or more nudges over a subsequent time period; and analyzing correlations between the monitored adherence and changes in glycemic control for the subject to assess therapeutic effectiveness of the interventions.

17. The computer-implemented method of claim 1, wherein adjusting the operational parameter comprises one or more of:

decreasing the monitoring frequency of the one or more sensors when determining, for the subject, a sustained adherence to the personalized content; and triggering monitoring of one or more physiological parameters by the wearable device for a subsequent time period based on the identified pattern.

18. A system for treating or preventing progression of prediabetes, diabetes, or metabolic syndrome in a user, the system comprising:

a wearable device configured to be worn on a body site of the user, the wearable device comprising:

at least one processor; and one or more sensors configured to monitor physiological parameters of the user;

memory storing instructions that, when executed by the at least one processor, cause the system to execute operations comprising:

receiving data for the user including a condition or risk factors corresponding to prediabetes, diabetes, or metabolic syndrome and receiving blood glucose data from the wearable device;

monitoring, using the one or more sensors, a plurality of behavioral events associated with the user and physiological responses of the user corresponding to the behavioral events, each event being correlated to a timestamp within a time period;

identifying, using the blood glucose data as input to a generative artificial intelligence system comprising one or more machine learning models trained on behavioral and physiological data, a pattern in the plurality of behavioral events, wherein the one or more machine learning models are configured to:

analyze temporal correlations between behavioral events and physiological responses of the user, and detect recurring behavioral sequences that correlate with changes in the blood glucose data;

generating, based on the identified pattern, the received blood glucose data, and the received data for the user, personalized content for the user using the generative artificial intelligence system, wherein the personalized content includes tailored behavioral interventions specific to the user and configured to modify dietary behavior, exercise behavior, or lifestyle behavior to improve glucose regulation and prevent progression of the prediabetes, diabetes, or metabolic syndrome;

generating one or more nudges for the user based on the personalized content, wherein the one or more nudges comprise prompts or suggestions aimed at encouraging adherence to executing suggested behavior changes provided in the personalized content;

automatically adjusting an operational parameter of the wearable device based on the identified pattern or the blood glucose data, wherein adjusting the operational parameter of the wearable device comprises changing a monitoring frequency or changing a frequency of receiving data from the wearable device; and causing presentation of the personalized content and the one or more nudges to the user.

19. The system of claim 18, wherein:

at least one of the plurality of behavioral events comprises a last consumed meal; and the personalized content comprises feedback on the last consumed meal.

20. The system of claim 18, wherein the operations further comprise:

determining a nudge mode selected from a light mode, a regular mode, and a heavy mode, the selection being based on a historical adherence to previously generated nudges or recommendations using a predictive machine learning model; and generating the one or more nudges according to the determined nudge mode.

21. The system of claim 20, wherein the heavy mode is activated during at least one of: periods following discontinuation of one or more medications or when the user sets aggressive health goals.

22. The system of claim 18, wherein the personalized content comprises a plurality of restaurant menu suggestions selected according to the identified pattern, and food data corresponding to each of the plurality of restaurant menu suggestions, the food data indicating one or more of: calorie content, sugar content, carbohydrate content, and at least one reason for selecting the respective restaurant menu suggestions.

23. The system of claim 18, wherein the operations are performed by an artificial intelligence health coach configured to share data with a buddy computing device according to permissions associated with the user, the shared data comprising one or more of: blood glucose estimations, identified patterns, a status update corresponding to the user, and a summary corresponding to the user.

24. The system of claim 18, wherein the personalized content comprises a grocery shopping list curated according to the identified pattern, and the operations further comprise automatically placing a plurality of items on the grocery shopping list in an online shopping cart or automatically placing an order of the plurality of items on the grocery shopping list.

25. A non-transitory computer-readable medium for managing behavior of a subject, the computer-readable medium storing instructions that when executed by at least one processor, cause the at least one processor to perform operations for treating or preventing progression of prediabetes, diabetes, or metabolic syndrome in a subject, the operations comprising:

providing a wearable device comprising at least one processor, memory, and one or more sensors configured to monitor physiological parameters of the subject;

receiving data for the subject including a condition or risk factors corresponding to prediabetes, diabetes, or metabolic syndrome and physiological data received from the one or more sensors of the wearable device;

monitoring, using the wearable device, a plurality of behavioral events associated with the subject and physiological parameters of the subject, each event being correlated to a timestamp within a time period;

identifying, using the received data input being provided to a generative artificial intelligence a pattern in the plurality of behavioral events that correlates with glucose dysregulation or elevated glycemic levels in the subject;

generating, using the generative artificial intelligence and based on the identified pattern and the received data, personalized content for the subject, wherein the personalized content includes tailored interventions to improve glycemic control of the subject;

generating one or more nudges for the subject based on the personalized content, wherein the one or more nudges comprise prompts or suggestions aimed at encouraging adherence to executing suggested behavior changes provided in the personalized content; and causing presentation of the personalized content and the one or more nudges to the subject, wherein the one or more nudges are configured to coach the subject to modify the behavior of the subject over an upcoming time period.

26. The non-transitory computer-readable medium of claim 25, wherein:

at least one of the plurality of behavioral events comprises a last consumed meal; and the personalized content comprises feedback on the last consumed meal.

27. The non-transitory computer-readable medium of claim 25, wherein the operations further comprise:

monitoring a behavior or input responsive to the presentation of the one or more nudges;

iteratively repeating the monitoring of the behavior or input exhibited by the subject;

in response to detecting additional behavioral events, identifying an additional pattern in the additional behavioral events;

updating the personalized content according to the additional behavioral events based on the identified additional pattern;

generating an updated nudge corresponding to the updated personalized content; and causing presentation of the updated nudge and the updated personalized content to the subject.

28. The non-transitory computer-readable medium of claim 25, wherein the personalized content comprises presentation of one or more venues and a grocery shopping list curated according to the identified pattern, a budget, a location of the subject, and a determination of an availability of a plurality of items on the grocery shopping list, and the operations further comprising automatically placing the plurality of items on the grocery shopping list in an online shopping cart or automatically placing an order of the plurality of items on the grocery shopping list.

29. The non-transitory computer-readable medium of claim 25, wherein the personalized content comprises a plurality of restaurant menu suggestions selected according to the identified pattern, and food data corresponding to each of the plurality of restaurant menu suggestions, the food data indicating one or more of: calorie content, sugar content, carbohydrate content, and at least one reason for selecting the respective restaurant menu suggestions.

30. The non-transitory computer-readable medium of claim 25, wherein the operations are performed by an artificial intelligence health coach configured to share data with a buddy computing device according to permissions associated with the subject, the shared data comprising one or more of: blood glucose estimations, identified patterns, a status update corresponding to the subject, and a summary corresponding to the subject.

\* \* \* \* \*